(12) United States Patent
Bard et al.

(10) Patent No.: US 11,981,729 B2
(45) Date of Patent: May 14, 2024

(54) METHOD

(71) Applicant: Agency for Science, Technology and Research, Singapore (SG)

(72) Inventors: Frederic Bard, Singapore (SG); Anh Tuan Nguyen, Singapore (SG); Ros Manon, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 18/449,190

(22) Filed: Aug. 14, 2023

(65) Prior Publication Data

US 2024/0052023 A1 Feb. 15, 2024

Related U.S. Application Data

(63) Continuation-in-part of application No. 17/570,301, filed on Jan. 6, 2022, which is a continuation of application No. 17/369,749, filed on Jul. 7, 2021, now abandoned, which is a continuation-in-part of application No. PCT/SG2020/050044, filed on Jan. 30, 2020.

(51) Int. Cl.
*A61K 39/395* (2006.01)
*C07K 16/18* (2006.01)

(52) U.S. Cl.
CPC .......... *C07K 16/18* (2013.01); *C07K 2317/24* (2013.01); *C07K 2317/54* (2013.01); *C07K 2317/55* (2013.01); *C07K 2317/622* (2013.01)

(58) Field of Classification Search
None
See application file for complete search history.

(56) References Cited

U.S. PATENT DOCUMENTS

2022/0363738 A1 11/2022 Bard et al.

FOREIGN PATENT DOCUMENTS

| CN | 108277275 A | 7/2018 |
|---|---|---|
| CN | 108309988 A | 7/2018 |
| EP | 2 320 235 A1 | 5/2011 |
| WO | WO 2003/060522 A1 | 7/2003 |
| WO | WO 2009/075883 A2 | 6/2009 |
| WO | WO 2013/011153 A2 | 1/2013 |
| WO | WO 2013/043644 A1 | 3/2013 |
| WO | WO 2019/070199 A1 | 4/2019 |
| WO | WO 2024/008960 A1 | 1/2024 |

OTHER PUBLICATIONS

Ryan et al. (J of Transl. Med 2016 14:196). (Year: 2016).*
Boon et al., Glycosylation of matrix metalloproteases and tissue inhibitors: present state, challenges and opportunities. Biochem J. Jun. 1, 2016;473(11):1471-82. doi: 10.1042/BJ20151154. PMID: 27234584; PMCID: PMC4888457.
Burchell et al., O-linked mucin-type glycosylation in breast cancer. Biochem Soc Trans. Aug. 20, 2018;46(4):779-788. doi: 10.1042/BST20170483. Epub Jun. 14, 2018. PMID: 29903935; PMCID: PMC6103458.
Chia et al., The GalNAc-T Activation (GALA) Pathway: Drivers and markers. PLoS One. Mar. 19, 2019;14(3):e0214118. doi: 10.1371/journal.pone.0214118. PMID: 30889231; PMCID: PMC6424425.
Cullina et al., A novel lectin-based enzyme-linked immunosorbent assay for the measurement of IgA1 in serum and secretory IgA1 in secretions. Clin Chim Acta. Jul. 16, 1993;216(1-2):23-38. doi: 10.1016/0009-8981(93)90136-r. PMID: 8222271.
Frasconi et al., Interaction of ERp57 with calreticulin: Analysis of complex formation and effects of vancomycin. Biophys Chem. Jan. 2012;160(1):46-53. doi: 10.1016/j.bpc.2011.09.003. Epub Sep. 17, 2011. PMID: 21996511.
Gilani et al., UM-164: A Potent c-Src/p38 Kinase Inhibitor with In Vivo Activity Against Triple-Negative Breast Cancer. Clin Cancer Res. Oct. 15, 2016;22(20):5087-5096. doi: 10.1158/1078-0432.CCR-15-2158. Epub May 6, 2016. Retraction in: Clin Cancer Res. Apr. 1, 2020;26(7): 1777. PMID: 27154914. PMID: 27154914.
Gill et al., Initiation of GalNAc-type O-glycosylation in the endoplasmic reticulum promotes cancer cell invasiveness. Proc Natl Acad Sci U S A. Aug. 20, 2013;110(34):E3152-61. doi: 10.1073/pnas.1305269110. Epub Aug. 2, 2013. PMID: 23912186; PMCID: PMC3752262.
Lin et al., GALNT6 Stabilizes GRP78 Protein by O-glycosylation and Enhances its Activity to Suppress Apoptosis Under Stress Condition. Neoplasia. Jan. 2017;19(1):43-53. doi: 10.1016/j.neo.2016.11.007. PMID: 28110670; PMCID: PMC6197318.
McDowell, Role of O-glycosylation of Calnexin in Cancer Cell Biology. University of Manchester. 2016. Thesis. 195 pages.
Moore et al., Reactivities of N-acetylgalactosamine-specific Lectins with Human IgA1 Proteins. Mol Immunol. Apr. 2007;44(10):2598-604. doi: 10.1016/j.molimm.2006.12.011. Epub Feb. 2, 2007. PMID: 17275907; PMCID: PMC2788496.
Nguyen et al., Modeling organelle-specific O-glycosylation in driving liver tumor growth, invasion and metastasis. Cancer Research. 2017. Abstract A39.
Nguyen et al., Organelle Specific O-Glycosylation Drives MMP14 Activation, Tumor Growth, and Metastasis. Cancer Cell. Nov. 13, 2017;32(5):639-653.e6. doi: 10.1016/j.ccell.2017.10.001. PMID: 29136507.
Ryan et al., Calnexin, an ER stress-induced protein, is a prognostic marker and potential therapeutic target in colorectal cancer. J Transl Med. Jul. 1, 2016;14(1):196. doi: 10.1186/s12967-016-0948-z. Erratum in: J Transl Med. 2016;14(1):222. PMID: 27369741; PMCID: PMC4930591.
Santana-Codina et al., A transcriptome-proteome integrated network identifies endoplasmic reticulum thiol oxidoreductase (ERp57) as a hub that mediates bone metastasis. Mol Cell Proteomics. Aug. 2013;12(8):2111-25. doi: 10.1074/mcp.M112.022772. Epub Apr. 26, 2013. PMID: 23625662; PMCID: PMC3734573.

(Continued)

*Primary Examiner* — Meera Natarajan

(74) *Attorney, Agent, or Firm* — Wolf, Greenfield & Sacks, P.C.

(57) ABSTRACT

We describe a Cnx/ERp57 inhibitor for use in the treatment or prevention of cancer.

8 Claims, 59 Drawing Sheets

(56) References Cited

OTHER PUBLICATIONS

Song et al., Insights into the role of ERp57 in cancer. Journal of Cancer. Mar. 1, 2021;12(8):2456-64. doi: 10.7150/jca.48707. PMID: 33758622.

Steentoft et al., Precision mapping of the human O-GalNAc glycoproteome through SimpleCell technology. EMBO J. May 15, 2013;32(10):1478-88. doi: 10.1038/emboj.2013.79. Epub Apr. 12, 2013. PMID: 23584533; PMCID: PMC3655468.

International Search Report and Written Opinion for Application No. PCT/EP2022/051297, mailed May 25, 2022.

Chen et al., Calnexin Impairs the Antitumor Immunity of CD4 and CD8ρ T Cells. Cancer Immunol Research. Jan. 2019;7(1):123-35.

Chen et al., Extraction and identification of synovial tissue-derived exosomes by different separation techniques. J Orthop Surg Res. Mar. 9, 2020;15(1):97. doi: 10.1186/s13018-020-01604-x.

Goel et al., Plasticity within the antigen-combining site may manifest as molecular mimicry in the humoral immune response. J Immunol. Dec. 15, 2004;173(12):7358-67. doi: 10.4049/jimmunol.173.12.7358.

Ishino et al., Expression of Tn and sialyl Tn antigens in synovial tissues in rheumatoid arthritis. Clin Exp Rheumatol. Mar.-Apr. 2010;28(2):246-9. Epub May 13, 2010.

Kaneko et al., Selective Inhibition of Membrane Type 1 Matrix Metalloproteinase Abrogates Progression of Experimental Inflammatory Arthritis: Synergy With Tumor Necrosis Factor Blockade. Arthritis Rheumatol. Feb. 2016;68(2):521-31. doi: 10.1002/art.39414.

Lloyd et al., Modelling the human immune response: performance of a 1011 human antibody repertoire against a broad panel of therapeutically relevant antigens. Protein Eng Des Sel. Mar. 2009;22(3):159-68. doi: 10.1093/protein/gzn058. Epub Oct. 29, 2008.

Ros et al., ER-resident oxidoreductases are glycosylated and trafficked to the cell surface to promote matrix degradation by tumour cells. Nat Cell Biol. Nov. 2020;22(11):1371-1381. doi: 10.1038/s41556-020-00590-w. Epub Oct. 19, 2020.

Weber et al., Antibodies to the endoplasmic reticulum-resident chaperones calnexin, BiP and Grp94 in patients with rheumatoid arthritis and systemic lupus erythematosus. Rheumatology (Oxford). Dec. 2010;49(12):2255-63. doi: 10.1093/rheumatology/keq272. Epub Aug. 17, 2010.

Zhang, Advances in the study of the endoplasmic reticulum molecular chaperone Calnexin. Bulletin of Biology. Jul. 10, 2008;43(8):7-10.

* cited by examiner

NRas/shp53

NRas/shp53 + Control IgG

NRas/shp53 + α-Calnexin IgG

WT + α-Calnexin IgG

NRas/shp53

NRas/shp53 + Control IgG

NRas/shp53 + α-Calnexin IgG

FIGURE 8C

Cell seeding ~ 70 000 cells per
gelatin/collagen coverslips
> Overnight incubation ⟶

Open image with ImageJ

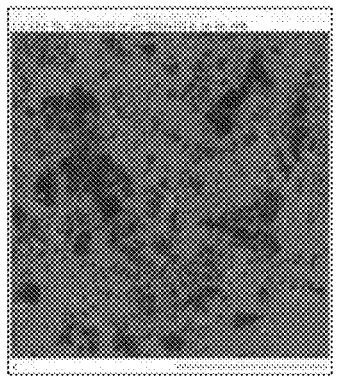

Image > Adjust > Threshold :

Adjust the threshold to have degradation
area totally filled (but no background)

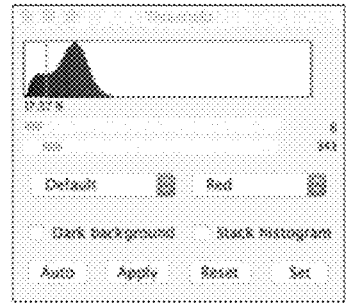

Analyze > Measure :
Quantify the area of
degraded gelatin

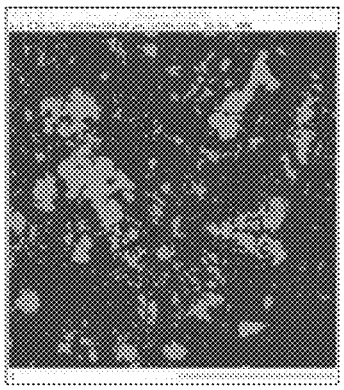

Divide the degraded area by the
number of nuclei in the same field

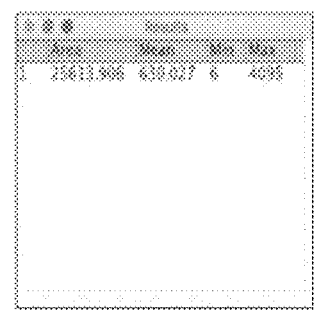

Normalized to control conditions :
Area degraded in sample / area
degraded in control

METHOD

RELATED APPLICATIONS

This application is a continuation in-part of U.S. patent application Ser. No. 17/570,301, filed Jan. 6, 2022, which is a continuation of U.S. patent application Ser. No. 17/369,749, filed Jul. 7, 2021, which is a continuation in-part of International Application No. PCT/SG2020/050044, filed Jan. 30, 2020, which is an international application that claims priority under 35 U.S.C. § 119(a)-(d) or 35 U.S.C. § 365(b) from Singaporean Application Number 1020190094X, filed Jan. 31, 2019.

FIELD

This invention relates to the fields of medicine, cell biology, molecular biology and genetics.

BACKGROUND

Cancer is a diverse set of more than a hundred diseases, but virtually all tumors share the ability to degrade the extracellular matrix (ECM). ECM degradative ability is a key feature of malignancy and while typically associated with metastasis, is also required for tumor growth[1-3].

The ECM is the structuring element of solid tissues and is normally relatively stable with for instance collagen fibers having a half-life of 60-70 days[4]. Collagen fibers and other ECM proteins form a meshwork that retains healthy cells and prevents tumor expansion[5]. Thus, cancer cells need to activate the ability to degrade ECM[6,7].

A family of specialized proteases, the matrix metalloproteases (MMPs), catalyzes the hydrolysis of peptide bonds in collagen and other matrix proteins. MMP14/MT1-MMP is a membrane-bound MMP that is essential for tumor cells[8]. This protease is typically enriched in podosomes and invadopodia, closely related structures that are found in macrophages/osteoclasts and tumor cells respectively[9,10].

Invadopodia are dynamic structures mediating ECM degradation that appear as dots on the ventral side of cells and can organize in ring-like structures called rosettes in cells with very high ECM degradation activity, such as osteoclasts or v-Src-transformed cells[11]. The tyrosine kinase Src is an important regulator of invadosome formation[9].

Src also drives the polypeptide N-Acetylgalactosaminyl-transferases (GALNTs) Activation (GALA) pathway[12]. GALA controls the abundance of GalNAc type glycans on various proteins with a lumenal or extracellular domain[3,12-15]. GALA is regulated by the relocation of O-glycosylation initiation enzymes GALNTs from the Golgi to the ER. GALNTs catalyse the formation of the Tn glycan, which consist of a single GalNac residue. Tn can be detected with lectins such as *Vicia Villosa* Lectin (VVL). GALNTs ER relocation dramatically increases the total cellular staining levels of Tn, with a cytoplasmic instead of perinuclear appearance[13]. Why the relocation of GALNTs to the ER leads to an increase of O-glycosylation in various proteins is not entirely clear 14.

High levels of Tn have long been associated with most solid tumors from a wide range of tissues[16-19]. We have shown that in a majority of breast, lung and liver cancers, Tn levels are controlled by GALA[3,13,20]. In breast and liver cancer cells, GALA promotes invasiveness. This increase is mediated in part by the glycosylation and activation of MMP14. MMP14 proteolytic activity is strictly dependent on its GalNac glycosylation[3]. However GALA affects a range of substrates in addition to MMP14, including both cell surface and ER-resident proteins[3]. Other substrates involved in ECM degradation could thus be activated by GALA.

ECM typically contains a complex mixture of over a thousand proteins, including multiple types of collagen, fibronectin, elastin and others[21]. The organization of the ECM is controlled partly by the formation of covalent bonds. For instance, lysyl-oxidases cross-link collagens as well as elastin fibers[22]. This cross-linking increases significantly resistance to collagenases[23]. Another type of cross-linking is accomplished by disulfide bridges, forming cysteine knots in some collagens[24,25]. Collagen type III, IV, V and VI as well as fibronectin contain disulfide bonds[26-28]. However, it remains unknown whether cells need to enzymatically cleave these disulfide bonds to degrade ECM. Disulfide bridges in secreted proteins can be formed in the ER or in the extracellular space[29]. In the ER, some disulfide bonds can alter protein folding and require isomerization[30,31]. The ER is thus endowed with numerous Protein Disulfide Isomerases (PDI), that mediate isomerization by reducing illegitimate disulfide bonds[32]. The membrane-bound Calnexin (Cnx) and the PDI ERp57 (aka PDIA3), form an oxidoreductase complex[33,34]. This complex functions in glutathione-dependent fashion[35].

SUMMARY

We demonstrate that native collagen preparations and ECM in liver tissue are heavily cross-linked by disulfide bonds and that reduction of these bonds is required for efficient degradation by cells.

We demonstrate that bond reduction is mediated by a cell-surface pool of Cnx/ERp57 complex. Cell surface exposure of the complex is mediated by GALA and the glycosylation of Cnx on a cluster of glycans on its N-terminal segment.

The Cnx/ERp57 complex is enriched in cell surface invadosomes where it reduces ECM disulfide bonds in a glutathione-dependent manner. This activity is essential in vivo for tumor growth and metastasis formation.

According to a 1$^{st}$ aspect of the present invention, we provide a Cnx/ERp57 inhibitor for use in the treatment or prevention of cancer.

The cancer may comprise invasive or metastatic cancer. The method or use may treat or prevent tumour growth or metastasis.

The cancer may be characterised by elevated levels of O-glycosylation. The cancer may be characterised by elevated levels of ER O-glycosylation. The cancer may be characterised by elevated levels of O-glycosylation of Cnx. The cancer may be selected from the group consisting of: liver, breast, sarcoma, lung, prostate, bladder, kidney, melanoma, pancreatic, endometrial, colorectal and thyroid cancer.

The Cnx/ERp57 inhibitor may be capable of inhibiting an ECM degradation activity of Cnx/ERp57. The Cnx/ERp57 inhibitor may be capable of inhibiting oxireductase activity of Cnx/ERp57. The Cnx/ERp57 inhibitor may be capable of inhibiting a disulphide bond reductase activity of Cnx/ERp57.

The Cnx/ERp57 inhibitor may comprise an antibody against Cnx or an antibody against ERp57.

The Cnx/ERp57 inhibitor may be capable of down-regulating any combination of the expression, amount or activity of a Cnx or ERp57, such as by RNA interference.

The Cnx/ERp57 inhibitor may comprises an antisense RNA, an siRNA or an shRNA against Cnx or ERp57.

The Cnx/ERp57 inhibitor may be capable of preventing GALA mediated 0-glycosylation of Cnx.

There is provided, according to a $2^{nd}$ aspect of the present invention, a kit for detecting cancer in an individual or susceptibility of the individual to cancer. The kit may comprise means for detection of Cnx/ERp57 in the individual or a sample taken from him or her. The kit may comprise a therapeutic drug for treatment, prophylaxis or alleviation of cancer.

We provide, according to a $3^{rd}$ aspect of the present invention, a method of detecting a cancer cell. We also provide for a method of determining the likelihood that a cell will become invasive or aggressive. We also provide for a method of predicting a decreased survival rate of an individual with cancer. The method may comprise detecting increased expression, amount or activity of Cnx/ERp57 in the cell, or a cell of the individual. The level may be increased as compared to Cnx/ERp57 activity in a control cell known to be non-cancerous.

As a $4^{th}$ aspect of the present invention, there is provided a method of choosing a therapy for an individual with cancer. The method may comprise detecting modulation of expression of Cnx/ERp57 in a cell of the individual. The method may comprise choosing an appropriate therapy, such as an anti-Cnx/ERp57 agent, based on the aggressiveness of the cancer.

We provide, according to a $5^{th}$ aspect of the present invention, a method of determining the likelihood of success of a particular therapy in an individual with a cancer. The method may comprise comparing the therapy with a therapy determined by a method set out above.

The present invention, in a $6^{th}$ aspect, provides a method of manipulating a cancer cell, such as an invasive or metastatic cancer cell. The method may comprise down-regulating the expression, amount or activity of Cnx/ERp57 in the cell. The down-regulation may be such that the cancer cell becomes non-cancerous or the invasive or metastatic cancer cell becomes non-invasive or non-metastatic as a result of the manipulation.

In a $7^{th}$ aspect of the present invention, there is provided a method of manipulating a cell. The method may comprise detecting increased Cnx/ERp57 expression, amount or activity in a cell. The method may comprise reducing the level of Cnx/ERp57 in the cell.

According to an $8^{th}$ aspect of the present invention, we provide a method of identifying a molecule capable of binding to Cnx/ERp57, the method comprising contacting Cnx/ERp57 with a candidate molecule and determining whether the candidate molecule binds to the Cnx/ERp57. We also provide a method of identifying a modulator of Cnx/ERp57, the method comprising contacting a cell with a candidate molecule and detecting elevated or reduced expression, amount or activity of Cnx/ERp57 in or of the cell. We also provide a method of identifying a molecule suitable for the treatment, prophylaxis or alleviation of cancer, the method comprising determining if a candidate molecule is an agonist or antagonist of Cnx/ERp57, preferably by exposing a candidate molecule to Cnx/ERp57 or a cell expressing Cnx/ERp57 in order to determine if the candidate molecule is an agonist or antagonist thereof. We also provide a method of identifying an agonist or antagonist of a Cnx/ERp57, the method comprising administering a candidate molecule to an animal and determining whether the animal exhibits increased or decreased expression, amount or activity of Cnx/ERp57; optionally isolating or synthesising the molecule, modulator, agonist or antagonist; in which the molecule, modulator, agonist or antagonist so identified comprises an Cnx/ERp57 inhibitor set out above.

We provide, according to a $9^{th}$ aspect of the invention, a method of determining whether a tumour in an individual is, or is likely to be, an invasive or metastatic tumour. The method may comprise detecting modulation of expression, amount or activity of Cnx/ERp57 in a tumour cell of the individual, preferably further comprising assessing the size of the tumour, or the lymph node stage, or both.

There is provided, in accordance with a $10^{th}$ aspect of the present invention, Cnx/ERp57 for use in a method of treatment or prevention of cancer in an individual.

The practice of this invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; D. M. J. Lilley and J. E. Dahlberg, 1992, *Methods of Enzymology: DNA Structure Part A: Synthesis and Physical Analysis of DNA Methods in Enzymology*, Academic Press; *Using Antibodies: A Laboratory Manual: Portable Protocol NO. I* by Edward Harlow, David Lane, Ed Harlow (1999, Cold Spring Harbor Laboratory Press, ISBN 0-87969-544-7); *Antibodies: A Laboratory Manual* by Ed Harlow (Editor), David Lane (Editor) (1988, Cold Spring Harbor Laboratory Press, ISBN 0-87969-314-2), 1855. *Handbook of Drug Screening*, edited by Ramakrishna Seethala, Prabhavathi B. Fernandes (2001, New York, NY, Marcel Dekker, ISBN 0-8247-0562-9); and *Lab Ref: A Handbook of Recipes, Reagents, and Other Reference Tools for Use at the Bench*, Edited Jane Roskams and Linda Rodgers, 2002, Cold Spring Harbor Laboratory, ISBN 0-87969-630-3. Each of these general texts is herein incorporated by reference.

BRIEF DESCRIPTION OF THE FIGURES

FIG. 1A is a drawing showing an immunoblot analysis of the level of Tn-modified cnx in 7 pairs of human HCC (T) versus adjacent normal liver tissues (NT). Quantification can be found on the right.

FIG. 1B is a drawing showing an immunoblot analysis of VVL IP of multiple Nras-G12V/shp53-injected mouse liver tumors as well as normal liver samples. Quantifications are represented below (gray bars).

FIG. 1C is a drawing showing an immunoblot analysis of Tn-modified cnx in THLE2, Huh6 and Huh7 cell lines. Quantifications can be found on the right (green bars).

FIG. 1D is a drawing showing an immunoblot analysis of Tn-modified cnx in MDA WT, Golgi-G2 and ER-G2 stable cell lines. Quantifications are represented on the right (red bars used for MDA cell lines).

FIG. 1E is a drawing showing an immunoblot analysis of Tn-modified cnx in NIH3T3 and NIH3T3vSrc cell lines. Quantifications are represented in the right (blue bars used for 3T3 cell lines).

FIG. 1F is a drawing showing immunofluorescence of NIH3T3vSrc cells stained with calnexin (Cnx) and the invadosome marker cortactin. Scale bar, 20 µm.

FIG. 1G is a drawing showing immunofluorescence of Huh7 cells stained with calnexin and cortactin. Scale bar, 10 µm.

FIG. 1H is a drawing showing cell surface immunofluorescence of calnexin in MDA WT and ER-G2 cells. Live cells were incubated with anti-calnexin antibody for 15 min at 37 C before fixation. Scale bar, 5 µm. Quantification of calnexin staining are represented on the right.

FIG. 1I is a drawing showing an immunoblot analysis of MDA Golgi-GG2 and ER-G2 after biotinylation and streptavidin pull down.

FIG. 2A is a drawing showing quantification of matrix degradation assay of Huh7 cells incubated with control antibody (IgG control) or anti-Cnx antibody.

FIG. 2B is a drawing showing representative images of matrix degradation assay in FIG. 2A. Scale bar, 50 µm.

FIG. 2C is a drawing showing quantification of matrix degradation assay of MDA ER-G2 cells transfected with control antibody (IgG control) or 2 different anti-calnexin antibodies. Values indicate the mean±SEM of normalized fold changes for 3 replicates. p<0.05 compared to IgG control.

FIG. 2D is a drawing showing quantification of matrix degradation assay of MDA ER-G2 cells transfected with control siRNA (siNT5) or siRNA against calnexin (siCnx). Values indicate the mean±SEM of normalized fold changes for 3 replicates. p<0.01 compared to siNT5.

FIG. 2E is a drawing showing quantification of rosette formation (number of rosettes per cell and percentage of cells making rosettes) in NIH3T3vSrc transfected with control siRNA (siNT5) or siRNA against Cnx (siCnx). ns, non significant.

FIG. 2F is a drawing showing immunofluorescence of NIH3T3vSrc cells stained with ERp57 and the invadosome marker cortactin. Scale bar, 20 µm.

FIG. 2G is a drawing showing immunofluorescence of proximity ligation assay in MDA WT and MDA ER-G2 cells. PLA probes for Cnx and ERp57. Scale bar, 10 µm. Quantification of PLA results can be found in the right. Values indicate the mean±SEM for 3 replicates. *p<0.05 compared to MDA WT.

FIG. 2H is a drawing showing quantification of matrix degradation assay of MDA ER-G2 cells transfected with control siRNA (siNT5) or 2 different siRNA against ERp57. Values indicate the mean±SEM of normalized fold changes for 2 replicates. p<0.01 compared to IgG control.

FIG. 2I is a drawing showing quantification of matrix degradation assay of MDA ER-G2 cells incubated with control antibody (IgG control) or 2 different anti-ERp57 antibodies. Values indicate the mean±SEM of normalized fold changes for 3 replicates. p<0.05 compared to IgG control.

FIG. 3A is a drawing showing a schematic representation of O-glycosylation sites on cnx. GalNAc sugar residues are represented by the yellow boxes.

FIG. 3B is a drawing showing mass spectrometry analysis of peptide with T66 glycosite in excised Cnx gel band from untransfected ER-G2 cells.

FIG. 3C is a drawing showing quantification of the relative abundance of peptide glycosylated at T66.

FIG. 3D is a drawing showing an immunoblot blot analysis of Cnx levels in MDA ER-G2 Cnx−/− cell line compared to MDA ER-G2 parental cell line.

FIG. 3E is a drawing showing quantification of matrix degradation assay of MDA ER-G2 and MDA ER-G2 cnx−/− not transfected or transfected with WT Cnx (cnx WT) or mutant Cnx (6mutCnx). Values indicate the mean±SEM of normalized fold changes for 3 replicates.

FIG. 3F is a drawing showing an immunoblot analysis of VVL IP of MDA WT, ER-G2 and ER-G2 cnx−/− cells transiently transfected with Cnx WT or Cnx mutant plasmid (6mutCnx). Quantifications are represented below. Values indicate the mean±SEM for 5 replicates and were normalized as fold change compared to cnx WT samples in each experiment. ****p<0.0001 compared to cnx WT transfected cells.

FIG. 4A is a drawing showing representation of chemical ECM disulfide bond reduction protocol using TCEP, NEM and OX133 staining.

FIG. 4B is a drawing showing immunofluorescence of ECM components and OX133 on decellularized liver, untreated or treated with TCEP. TCEP-treated slices were incubated with NEM before staining (or no NEM for control). Scale bar, 50 µm.

FIG. 4C is a drawing showing immunofluorescence of NIH3T3vSrc cells seeded on red ECM and stained with OX133 antibody. ECM was incubated with cells but ECM only was imaged in this field (representation of the used protocol can be found above). Scale bar, 10 µm.

FIG. 4D is a drawing showing quantification of relative OX133 staining in FIG. 3D.

FIG. 4E is a drawing showing quantification of matrix degradation assay of MDA ER-G2 cells incubated with GSH (+GSH, left panel) or with GPx and $H_2O_2$ (+GPx, right panel). Values indicate the mean±SEM of normalized fold changes for 3 replicates. *p<0.05 compared to control untreated cells.

FIG. 4F is a drawing showing quantification of matrix degradation assay of MDA ER-G2 transfected with control siRNA or calnexin siRNA. ECM disulfide bonds were chemically reduced using TCEP (+TCEP) or left untreated (−TCEP) before cell seeding. Values indicate the mean±SEM of normalized fold changes for 3 replicates. *p<0.05, ***p<0.001.

FIG. 5A is a drawing showing a schematic of mouse model of breast cancer metastasis to the lung by tail-vein injection of human breast cancer cell line MDA-MB-231 (on top). The graph representing the number of nodules in each condition can be found below.

FIG. 5B is a drawing showing histopathological (H&E) and immunohistochemistry analysis of lung samples in FIG. 5A. Scale bars, 1 mm (left column) and 100 µm (other columns).

FIG. 5C is a drawing showing a schematic of mouse model of breast cancer metastasis to the lung by tail-vein injection of human breast cancer cell line MDA-MB-231, supplemented by anti-cnx antibody or control antibody (IgG control) injection (on top). The graph representing the number of nodules in each condition can be found below.

FIG. 5D is a drawing showing quantification of percent of lung out of total body weight in MDA ER-G2-injected mice treated with calnexin antibody as compared to no-treatment of IgG control groups.

FIG. 5E is a drawing showing immunohistochemistry for VVL staining of lung samples in FIG. 5C and FIG. 5D. Scale bars, 1 mm (left column) and 100 µm (right column).

FIG. 5F is a drawing showing a schematic of the workflow of calnexin antibody injection in a mouse model for liver cancer and its lung metastasis (on top). Quantification of the percentage of mice showing metastasis can be found below. Mice with lung metastasis are represented by red bars, free-metastasis mice are represented by green bars.

FIG. 5G is a drawing showing VVL immunohistochemistry of lung mice in FIG. 5F. mCherry-NRas staining is used to detect lung metastasis. Scale bars, 1 mm (left column) and 100 µm (other columns).

FIG. 6A is a drawing showing a workflow of hydrodynamic injection of Nras/shp53 plasmids into mice followed by control or anti-calnexin antibodies.

FIG. 6B is a drawing showing immunofluorescence of mouse liver expressing NRas/shp53 and injected with Cnx antibody (top) or injected with control IgG antibody (bottom). WT mouse liver injected with Cnx antibody. Scale bar, 100 µm.

FIG. 6C is a drawing showing the average area of mCherry expressing cells in mouse livers after injection of Nras/shp53 plasmid alone or in combination with control or anti-Cnx antibodies.

FIG. 6D is a drawing showing an immunohistochemistry analysis of mouse livers after injection of Nras/shp53 plasmid alone or in combination with control or anti-Cnx antibodies. Scale bars, 1 mm (top row) and 100 µm (middle and bottom rows).

FIG. 8C is a drawing showing a workflow on ImageJ software to quantify degradation per nuclei.

DETAILED DESCRIPTION

Figure 1A:
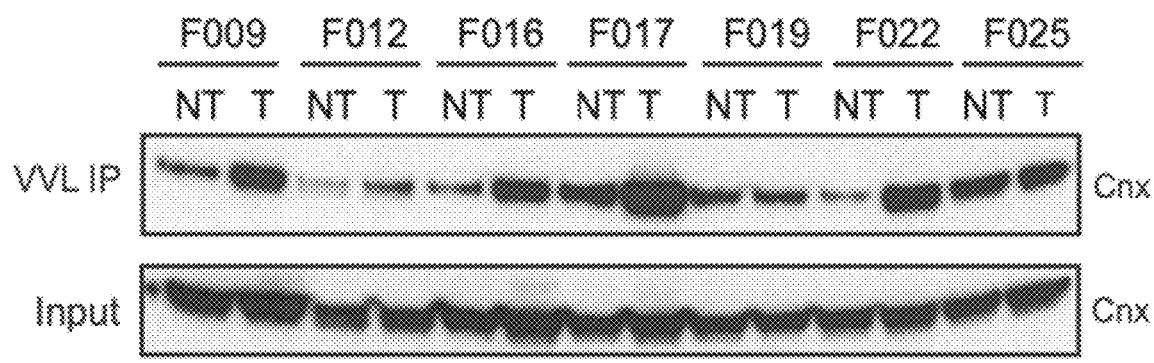
FIGS. 1A to 1I are drawings showing that GALA induces calnexin glycosylation and calnexin expression in invadosomes.
Figure 1A:
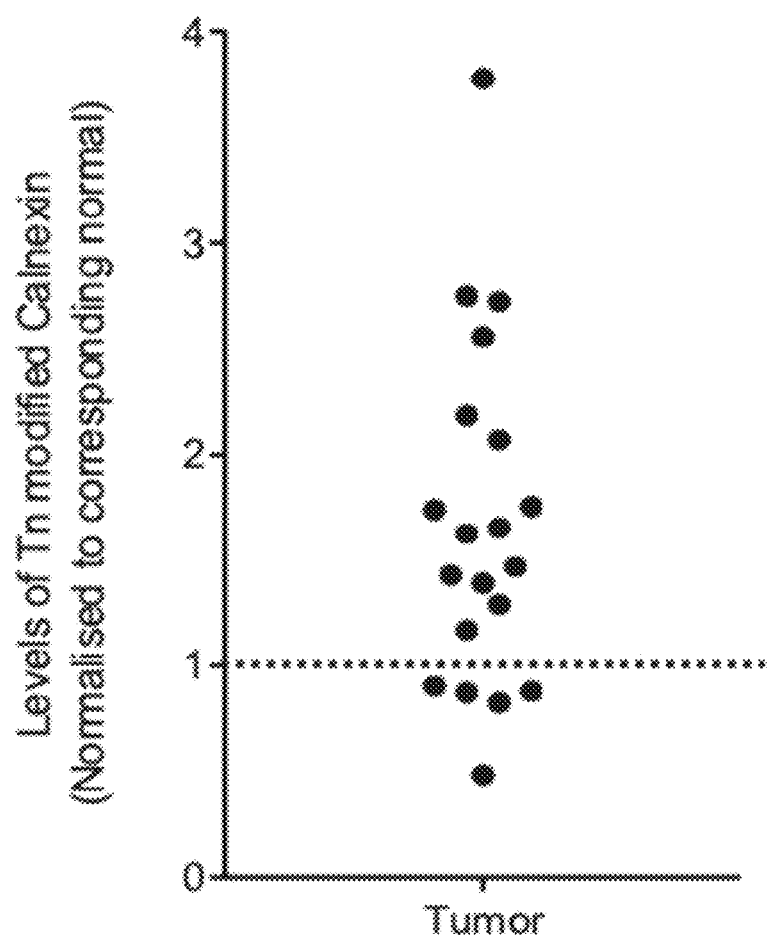

Tumor growth and invasiveness require extracellular matrix (ECM) degradation and are stimulated by the GALA pathway, which drives protein O-glycosylation in the ER. ECM degradation requires cleavage of peptidic bonds by metalloproteases but whether other enzymatic processing is required is unclear.

We demonstrate in the Examples that GALA induces the glycosylation of the ER-resident chaperone Calnexin (Cnx) in breast and liver cancer.

The Examples show that glycosylated Cnx and its partner ERp57 are trafficked to cell surface invadosomes, sites of ECM degradation. The Cnx/ERp57 complex is known to isomerize disulfide bridges in the ER.

We show in the Examples that disulfide bridges are abundant in connective and liver ECM. The cell surface Cnx/ERp57 complex is able to reduce extracellular disulfide bonds and is required for ECM degradation, while dispensable after the chemical reduction of ECM. In vivo, liver cancer cells but not healthy hepatocytes display cell surface Cnx.

The Examples demonstrate that liver tumor growth and lung metastasis of breast and liver cancer cells are inhibited by anti-Cnx antibodies.

These findings uncover a moonlighting function of Cnx/ERp57 at the cell surface essential for ECM breakdown and tumor development.

Cnx/ERp57 in the Treatment and Diagnosis of Cancer

The disclosure is based on the demonstration, for the first time, that Cnx/ERp57 plays a role in cancer.

Specifically, we show that Cnx/ERp57 plays a critical role in extracellular matrix (ECM) degradation, leading to invasion and tumorigenesis of cancer cells. We show in the Examples that Cnx/ERp57 is expressed in liver cancer cells but not healthy cells.

Accordingly, Cnx/ERp57 may be used as a marker for detection of cancer, including breast and liver cancer. The level of Cnx/ERp57 expression may be used as an indicator of cancer, in particular breast cancer or liver cancer. The level of Cnx/ERp57 expression may also be used as an indicator of likelihood of such a cancer.

We therefore provide for methods of diagnosis or detection of a cancer, particularly breast and liver cancer. We further provide methods of diagnosis and detection of the aggressiveness or invasiveness or the metastatic state, or any combination of these, of such a cancer. The methods may comprise analysis of protein levels (e.g., immunohistochemistry) or RNA levels (e.g., by in situ hybridisation). Such diagnostic and detection methods are described in further detail below.

We show that liver tumour growth and lung metastasis of breast and liver cancer cells are inhibited by anti-Cnx antibodies.

Accordingly, we provide for methods of treatment or prophylaxis of an individual suffering from cancer. Restoration of Cnx/ERp57 levels to those in normal tissue may also be used as a means of restoring normal function of breast cells. We therefore provide for the use of Cnx/ERp57 nucleic acids and polypeptides for the treatment of cancers, including breast and liver cancer. Our methods may be used for treatment or prophylaxis of breast or liver cancer or invasive cancer such as invasive breast cancer or liver cancer.

We further provide for the use of Cnx/ERp57 screening for drugs against cancer, including breast and liver cancer such as invasive breast or liver cancer. Such screens may involve detecting the modulation of binding between Cnx and ERp57 by the presence of a candidate molecule.

We provide for a method of identifying a molecule for the treatment or prophylaxis of cancer, including breast and liver cancer such as invasive breast or liver cancer, the method comprising identifying a modulator of an activity or expression of Cnx/ERp57.

We show in the Examples that cell surface Cnx/ERp57 complex is able to reduce extracellular disulfide bonds and is required for ECM degradation, and that this interaction is essential for oncogenesis.

Accordingly, we provide for a method of identifying a molecule for the treatment or prophylaxis of cancer, including breast and liver cancer such as invasive breast or liver cancer, the method comprising detecting an effect of a candidate molecule on the binding between Cnx7 and ERp5. A screen for small molecule inhibitors of Cnx/ERp57 binding may be conducted on a library for example.

Alternatively, or in addition, rational design may be employed to produce candidate inhibitors of a Cnx/ERp57 interaction. Thus, for example, a peptide from a Cnx binding region of a ERp57 may be designed. Similarly, a peptide from a ERp57 binding region of a Cnx may be designed.

Putative inhibitors (or candidate inhibitors identified in a screen) may be tested using a number of assays.

We further provide for the treatment or prophylaxis of cancer by interfering with or disrupting a Cnx/ERp57 interaction. This may be achieved by various means, for example, by introducing a modulator of Cnx, such as a molecule identified from a screen or design described above, to a patient in need thereof.

Cells over- and under-expressing Cnx/ERp57, as well as tissues, organs and organisms comprising these may be used as models for cancer or in screens for anti-cancer agents.

Cnx/ERp57

Where the term "Cnx/ERp57" is employed, this should be taken to mean reference to the complex of Cnx and ERp57, or any of its components, as the context dictates.

Calnexin has Gene ID: 821. ERp57, also known as PDIA3 has Gene ID: 2923. Further detail on calnexin and ERp57/PDIA3 is set out in the text below.

Cnx/ERp57 Inhibitor

As used in this document, a Cnx/ERp57 inhibitor is anything that is capable of inhibiting a Cnx/ERp57 complex, or any of its components.

The Cnx/ERp57 inhibitor may inhibit the activity of the Cnx/ERp57 complex or any of its components. It may do so by lowering the level of the Cnx/ERp57 complex in a cell, tissue, organ or organism.

A Cnx/ERp57 inhibitor may inhibit the formation of the complex or the activity of any of its components, such as Cnx or ERp57.

A Cnx/ERp57 inhibitor may therefore comprise a Cnx inhibitor or a ERp57 inhibitor.

Extracellular Matrix (ECM) As the term is used in this document, extracellular matrix (ECM) refers to an ensemble of proteins including collagens, fibronectin, elastin, laminin, proteoglycans, fibrillins and other glycoproteins such as Lama1-5 5 Laminin alpha subunits Lamb1-4 3 Laminin beta subunits Lamc1-3 3 Laminin gamma subunits Nid1/2 2 Nidogens Colq Collagen-like tail subunit of asymmetric acetylcholinesterase Major known ECM glycoproteins Eln Elastin Emilin1-3 3 Emilins, elastin microfibril interfacers Emid1/2 2 EMI domain-containing proteins Fbln1/2/5/7 4 Fibulins Efemp 1/2 Fibulins 3 and 4 Fbn1/2 2 Fibrillins Fn1 Fibronectin Fras1 Fraser syndrome 1 homolog Gldn Gliomedin Hmcn1/2 Hemicentins 1 and 2 Ibsp Integrin-binding sialoprotein, BSP Matn1-4 4 Matrilin proteins Mfap1a/b-5 6 Microfibrillar-associated proteins Mmrn1 and 2 2 Multimerins Npnt Nephronectin Papin Papilin, proteoglycan-like sulfated glycoprotein Postn Periostin, osteoblast-specific factor Sparc/Sparcl1 Secreted acidic cysteine-rich glycoproteins SPARC and SPARC-like Spp1/Srpx 2 Secreted phosphoprotein 1, osteopontin Tnc/n/r/x 4-5 Tenascins Thbs1-4 4 Thrombospondins—see also COMP/TSPS Comp/TSPS Cartilage oligomeric matrix protein (thrombospondin 5) Nervous system-enriched ECM proteins Agrn Agrin Coch Cochlin Ntn1-5 4 Netrins Ntng1/g2 Netrins G1/G2 Reln Reelin Slit1-3 3 Slit homologs Sspo SCO-spondin Tecta/b Tectorins a and b Vascular ECM proteins Fga/b/g Fibrinogen a/b/g chains Vtn Vitronectin Vwf von Willebrand factor ECM proteins of bones, cartilage, and teeth Ambn Ameloblastin Amelx Amelogenin X chromosome Bglap2 Bone g-carboxyglutamate protein 2 Bglap-rs1 Bone g-carboxyglutamate protein-related sequence 1 Cilp Cartilage intermediate-layer protein, nucleotide pyrophosphohydrolase Cilp2 Cartilage intermediate-layer protein 2 Dmp1 Dentin matrix protein 1 Dpt Dermatopontin Dspp Dentin sialophosphoprotein Mgp Matrix Gla protein CCN family proteins Cyr61 Cysteine rich protein 61, CCN1 Ctgf Connective tissue growth factor, CCN2 Nov Nephroblastoma overexpressed gene, CCN3 Wisp1-3 3 WNT1 inducible signaling pathway proteins, CCN4-6.

Where reference is made to anything done to ECM, this should be taken to include reference done to any of its components, for example, as set out above.

Cnx/ERp57 Polypeptides

The methods and compositions described here make use of Cnx/ERp57 polypeptides, which are described in detail below.

As used here, the term "Cnx/ERp57" is intended to refer to a complex comprising Cnx having Gene ID: 821 and ERp57 having Gene ID: 2923.

Where reference is made to a Cnx polypeptide, this should be taken as a reference to any member of the Cnx family of polypeptides. Of particular interest are Cnx polypeptides derived from the genes in the group consisting of: Mouse Gene ID: 12330, Rat Gene ID: 29144, Dog Gene ID: 403908, Cat Gene ID: 101085686 and Horse Gene ID: 100067402.

For example, the Cnx polypeptide may comprise a human Cnx sequence having GenBank Accession Number NP_001350929.1, NP_001350926.1, NP_001350923.1, NP_001350922.1, NP_001350924.1, NP_001350928.1, NP_001350927.1 or NP_001019820.1.

Where reference is made to a ERp57 polypeptide, this should be taken as a reference to any member of the ERp57 family of polypeptides. Of particular interest are ERp57 polypeptides derived from the genes in the group consisting of: *Homo sapiens* GeneID: 2923, *Mus musculus* GeneID: 14827, *Rattus norvegicus* GeneID: 29468, *Bos taurus* GeneID: 281803, *Equus caballus* GeneID: 100056198, *Felis catus* GeneID: 101097245 and *Canis lupus familiaris* GeneID: 478279.

For example, the ERp57 polypeptide may comprise a human ERp57 sequence having GenBank Accession Number NP_005304.3.

Homologues variants and derivatives thereof of any, some or all of these polypeptides are also included.

Cnx/ERp57 polypeptides may be used for a variety of means. They may also be used for production or screening of Cnx/ERp57 inhibitors, in particular, anti-Cnx/ERp57 antibodies. These are described in further detail below. The expression of Cnx/ERp57 polypeptides may be detected for diagnosis or detection of cancer, in particular breast or liver cancer. Cnx/ERp57 polypeptides may be used to treat or prevent such cancers.

A "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids.

"Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications.

Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-inking, cyclization, disulfide bond formation, demethylation, formation of covalent cross-inks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, *Proteins—Structure and Molecular Properties,* 2nd Ed., T. E. Creighton, W. H. Freeman and Company, New York, 1993 and Wold, F., *Posttranslational Protein Modifications: Perspectives and Prospects,* pgs. 1-12 in *Posttranslational Covalent Modification of Proteins,* B. C. Johnson, Ed., Academic Press, New York, 1983; Seifter et al., "Analysis for protein modifications and non-protein cofactors", *Meth Enzymol* (1990) 182:626-646 and Rattan et aL, "Protein Synthesis: Posttranslational Modifications and Aging", *Ann NY Acad Sci* (1992) 663:48-62.

The term "polypeptide" includes the various synthetic peptide variations known in the art, such as a retroinverso D peptides. The peptide may be an antigenic determinant and/or a T-cell epitope. The peptide may be immunogenic in vivo. The peptide may be capable of inducing neutralising antibodies in vivo.

As applied to Cnx/ERp57, the resultant amino acid sequence may have one or more activities, such as biological activities in common with a Cnx or ERp57 polypeptide, for example a human Cnx or ERp57 polypeptide. For example, a Cnx or ERp57 homologue may have a increased expression level in breast or liver cancer cells compared to normal breast or liver cells.

In particular, the term "homologue" covers identity with respect to structure and/or function providing the resultant amino acid sequence has Cnx or ERp57 activity. With respect to sequence identity (i.e. similarity), there may be at least 70%, such as at least 75%, such as at least 85%, such as at least 90% sequence identity. There may be at least 95%, such as at least 98%, sequence identity. These terms also encompass polypeptides derived from amino acids which are allelic variations of the Cnx or ERp57 nucleic acid sequence.

Where reference is made to the "activity" or "biological activity" of a polypeptide such as Cnx and ERp57, these terms are intended to refer to the metabolic or physiological function of Cnx and ERp57, including similar activities or improved activities or these activities with decreased undesirable side effects. Also included are antigenic and immunogenic activities of Cnx and ERp57. Examples of such activities, and methods of assaying and quantifying these activities, are known in the art, and are described in detail elsewhere in this document.

For example, such activities may include ECM degradation activity. Such an activity may be assayed using the methods described in the Examples.

Other Cnx and ERp57 Polypeptides

Cnx and ERp57 variants, homologues, derivatives and fragments are also of use in the methods and compositions described here.

The terms "variant", "homologue", "derivative" or "fragment" in relation to Cnx and ERp57 include any substitution of, variation of, modification of, replacement of, deletion of or addition of one (or more) amino acid from or to a sequence. Unless the context admits otherwise, references to "Cnx" and "ERp57" includes references to such variants, homologues, derivatives and fragments of Cnx and ERp57.

As used herein a "deletion" is defined as a change in either nucleotide or amino acid sequence in which one or more nucleotides or amino acid residues, respectively, are absent. As used herein an "insertion" or "addition" is that change in a nucleotide or amino acid sequence which has resulted in the addition of one or more nucleotides or amino acid residues, respectively, as compared to the naturally occurring substance. As used herein "substitution" results from the replacement of one or more nucleotides or amino acids by different nucleotides or amino acids, respectively.

Cnx and ERp57 polypeptides as described here may also have deletions, insertions or substitutions of amino acid residues which produce a silent change and result in a functionally equivalent amino acid sequence. Deliberate amino acid substitutions may be made on the basis of similarity in polarity, charge, solubility, hydrophobicity, hydrophilicity, and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the table below. Amino acids in the same block in the second column and in the same line in the third column may be substituted for each other:

| ALIPHATIC | Non-polar | G A P |
| | | I L V |
| | Polar—uncharged | C S T M |
| | | N Q |
| | Polar—charged | D E |
| | | K R |
| AROMATIC | | H F W Y |

Cnx and ERp57 polypeptides may further comprise heterologous amino acid sequences, typically at the N-terminus or C-terminus, such as the N-terminus. Heterologous sequences may include sequences that affect intra or extracellular protein targeting (such as leader sequences). Heterologous sequences may also include sequences that increase the immunogenicity of the Cnx and ERp57 polypeptide and/or which facilitate identification, extraction and/or purification of the polypeptides. Another heterologous sequence that may be used is a polyamino acid sequence such as polyhistidine which may be N-terminal. A polyhistidine sequence of at least 10 amino acids, such as at least 17 amino acids but fewer than 50 amino acids may be employed.

The Cnx and ERp57 polypeptides may be in the form of the "mature" protein or may be a part of a larger protein such as a fusion protein. It is often advantageous to include an additional amino acid sequence which contains secretory or leader sequences, pro-sequences, sequences which aid in purification such as multiple histidine residues, or an additional sequence for stability during recombinant production.

Cnx and ERp57 polypeptides as described here are advantageously made by recombinant means, using known techniques. However they may also be made by synthetic means using techniques well known to skilled persons such as solid phase synthesis. Such polypeptides may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences, such as a thrombin cleavage site. The fusion protein may be one which does not hinder the function of the protein of interest sequence.

The Cnx and ERp57 polypeptides may be in a substantially isolated form. This term is intended to refer to alteration by the hand of man from the natural state. If an "isolated" composition or substance occurs in nature, it has been changed or removed from its original environment, or both. For example, a polynucleotide, nucleic acid or a polypeptide naturally present in a living animal is not "isolated," but the same polynucleotide, nucleic acid or polypeptide separated from the coexisting materials of its natural state is "isolated", as the term is employed herein.

It will however be understood that the Cnx or ERp57 protein may be mixed with carriers or diluents which will not interfere with the intended purpose of the protein and still be regarded as substantially isolated. A Cnx and ERp57 polypeptide may also be in a substantially purified form, in which case it will generally comprise the protein in a preparation in which more than 90%, for example, 95%, 98% or 99% of the protein in the preparation is a Cnx and ERp57 polypeptide.

By aligning Cnx and ERp57 sequences from different species, it is possible to determine which regions of the amino acid sequence are conserved between different species ("homologous regions"), and which regions vary between the different species ("heterologous regions").

The Cnx and ERp57 polypeptides may therefore comprise a sequence which corresponds to at least part of a homologous region. A homologous region shows a high degree of homology between at least two species. For example, the homologous region may show at least 70%, at least 80%, at least 90% or at least 95% identity at the amino acid level using the tests described above. Peptides which comprise a sequence which corresponds to a homologous region may be used in therapeutic strategies as explained in further detail below. Alternatively, the Cnx and ERp57 peptide may comprise a sequence which corresponds to at least part of a heterologous region. A heterologous region shows a low degree of homology between at least two species.

Cnx and ERp57 Homologues

The Cnx or ERp57 polypeptides disclosed for use include homologous sequences obtained from any source, for example related viral/bacterial proteins, cellular homologues and synthetic peptides, as well as variants or derivatives thereof. Thus polypeptides also include those encoding homologues of Cnx or ERp57 from other species including animals such as mammals (e.g. mice, rats or rabbits), especially primates, more especially humans. More specifically, homologues include human homologues.

In the context of this document, a homologous sequence is taken to include an amino acid sequence which is at least 15, 20, 25, 30, 40, 50, 60, 70, 80 or 90% identical, such as at least 95 or 98% identical at the amino acid level, for example over at least 50 or 100, 200, 300, 400 or 500 amino acids with the sequence of a relevant Cnx or ERp57 sequence.

In particular, homology should typically be considered with respect to those regions of the sequence known to be essential for protein function rather than non-essential neighbouring sequences. This is especially important when considering homologous sequences from distantly related organisms.

Although homology can also be considered in terms of similarity (i.e. amino acid residues having similar chemical properties/functions), in the context of the present document homology may be expressed in terms of sequence identity.

Homology comparisons can be conducted by eye, or more usually, with the aid of readily available sequence comparison programs. These publicly and commercially available computer programs can calculate % identity between two or more sequences.

% identity may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local identity or similarity.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, the default values may be used when using such software for sequence comparisons. For example when using the GCG Wisconsin Bestfit package (see below) the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Altschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). The GCG Bestfit program may be used.

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). The public default values for the GCG package may be used, or in the case of other software, the default matrix, such as BLOSUM62.

Once the software has produced an optimal alignment, it is possible to calculate % homology, such as % sequence identity. The software typically does this as part of the sequence comparison and generates a numerical result.

The terms "variant" or "derivative" in relation to amino acid sequences includes any substitution of, variation of, modification of, replacement of, deletion of or addition of one (or more) amino acids from or to the sequence providing the resultant amino acid sequence retains substantially the same activity as the unmodified sequence, such as having at least the same activity as the Cnx or ERp57 polypeptides.

Polypeptides having the Cnx or ERp57 amino acid sequence disclosed here, or fragments or homologues thereof may be modified for use in the methods and compositions described here. Typically, modifications are made that maintain the biological activity of the sequence. Amino acid substitutions may be made, for example from 1, 2 or 3 to 10, 20 or 30 substitutions provided that the modified sequence retains the biological activity of the unmodified sequence. Alternatively, modifications may be made to deliberately inactivate one or more functional domains of the polypeptides described here. Amino acid substitutions may include the use of non-naturally occurring analogues, for example to increase blood plasma half-life of a therapeutically administered polypeptide.

Cnx and ERp57 Fragments

Polypeptides for use in the methods and compositions described here also include fragments of the full length sequence of any of the Cnx or ERp57 polypeptides identified above. Fragments may comprise at least one epitope. Methods of identifying epitopes are well known in the art. Fragments will typically comprise at least 6 amino acids, such as at least 10, 20, 30, 50 or 100 amino acids.

Included are fragments comprising or consisting of, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315 or more residues from a relevant Cnx or ERp57 amino acid sequence.

We further describe peptides comprising a portion of a Cnx or ERp57 polypeptide as described here. Thus, fragments of Cnx or ERp57 and their homologues, variants or derivatives are included. The peptides may be between 2 and 200 amino acids, such as between 4 and 40 amino acids in length. The peptide may be derived from a Cnx or ERp57 polypeptide as disclosed here, for example by digestion with a suitable enzyme, such as trypsin. Alternatively the peptide, fragment, etc may be made by recombinant means, or synthesised synthetically.

Such fragments of Cnx or ERp57 may suitably be provided in the form of peptides, which may be used as anti-Cnx or anti-ERp57 peptides. Accordingly, we disclose peptides comprising sequences of Cnx and ERp57 which flank either or both of these positions. The peptides may be of any suitable length, such as between 5 to 40 (or more) residues of Cnx or ERp57 sequence. The peptides may comprise, for example, a 5, 10, 15, 20, 25, etc residue long sequence.

The peptides may be introduced into a cell, tissue, organ or individual through various means, such as by use of membrane translocation sequences, including for example, the whole sequence or subsequences of the HIV-1-transactivating protein (Tat), *Drosophila* Antennapedia homeodomain protein (Antp-HD), Herpes Simplex-1 virus VP22 protein (HSV-VP22), signal-sequence-based peptides, Transportan and Amphiphilic model peptide, among others. These are described in detail in WO 2002/007752.

Cnx or ERp57 and their fragments, homologues, variants and derivatives, may be made by recombinant means. However they may also be made by synthetic means using techniques well known to skilled persons such as solid phase synthesis. The proteins may also be produced as fusion proteins, for example to aid in extraction and purification. Examples of fusion protein partners include glutathione-S-transferase (GST), 6×His, GAL4 (DNA binding and/or transcriptional activation domains) and β-galactosidase. It may also be convenient to include a proteolytic cleavage site between the fusion protein partner and the protein sequence of interest to allow removal of fusion protein sequences. The fusion protein may be one which will not hinder the function of the protein of interest sequence. Proteins may also be obtained by purification of cell extracts from animal cells.

The Cnx or ERp57 polypeptides, variants, homologues, fragments and derivatives disclosed here may be in a substantially isolated form. It will be understood that such polypeptides may be mixed with carriers or diluents which will not interfere with the intended purpose of the protein and still be regarded as substantially isolated. A Cnx or ERp57 variant, homologue, fragment or derivative may also be in a substantially purified form, in which case it will generally comprise the protein in a preparation in which more than 90%, e.g. 95%, 98% or 99% of the protein in the preparation is a protein.

The Cnx or ERp57 polypeptides, variants, homologues, fragments and derivatives disclosed here may be labelled with a revealing label. The revealing label may be any suitable label which allows the polypeptide, etc to be detected. Suitable labels include radioisotopes, e.g. $^{125}$I, enzymes, antibodies, polynucleotides and linkers such as biotin. Labelled polypeptides may be used in diagnostic procedures such as immunoassays to determine the amount of a polypeptide in a sample. Polypeptides or labelled polypeptides may also be used in serological or cell-mediated immune assays for the detection of immune reactivity to said polypeptides in animals and humans using standard protocols.

A Cnx or ERp57 polypeptides, variants, homologues, fragments and derivatives disclosed here, optionally labelled, may also be fixed to a solid phase, for example the surface of an immunoassay well or dipstick. Such labelled and/or immobilised polypeptides may be packaged into kits in a suitable container along with suitable reagents, controls, instructions and the like. Such polypeptides and kits may be used in methods of detection of antibodies to the polypeptides or their allelic or species variants by immunoassay.

Immunoassay methods are well known in the art and will generally comprise: (a) providing a polypeptide comprising an epitope bindable by an antibody against said protein; (b) incubating a biological sample with said polypeptide under conditions which allow for the formation of an antibody-antigen complex; and (c) determining whether antibody-antigen complex comprising said polypeptide is formed.

The Cnx or ERp57 polypeptides, variants, homologues, fragments and derivatives disclosed here may be used in in vitro or in vivo cell culture systems to study the role of their corresponding genes and homologues thereof in cell function, including their function in disease. For example, truncated or modified polypeptides may be introduced into a cell to disrupt the normal functions which occur in the cell. The polypeptides may be introduced into the cell by in situ expression of the polypeptide from a recombinant expression vector (see below). The expression vector optionally carries an inducible promoter to control the expression of the polypeptide.

The use of appropriate host cells, such as insect cells or mammalian cells, is expected to provide for such post-translational modifications (e.g. myristolation, glycosylation, truncation, lapidation and tyrosine, serine or threonine phosphorylation) as may be needed to confer optimal biological activity on recombinant expression products. Such cell culture systems in which the Cnx or ERp57 polypeptides, variants, homologues, fragments and derivatives disclosed here are expressed may be used in assay systems to identify candidate substances which interfere with or enhance the functions of the polypeptides in the cell.

Cnx and ERp57 Nucleic Acids

The methods and compositions described here may employ, as a means for detecting expression levels of Cnx or ERp57, Cnx or ERp57 polynucleotides, Cnx or ERp57 nucleotides and Cnx or ERp57 nucleic acids, as well as variants, homologues, derivatives and fragments of any of these.

In addition, we disclose particular Cnx or ERp57 fragments useful for the methods of diagnosis described here. The Cnx or ERp57 nucleic acids may also be used for the methods of treatment or prophylaxis described.

The terms "Cnx polynucleotide", "Cnx nucleotide" and "Cnx nucleic acid" (and "ERp57 polynucleotide", "ERp57 nucleotide" and "ERp57 nucleic acid") may be used interchangeably, and should be understood to specifically include both cDNA and genomic Cnx or ERp57 sequences. These terms are also intended to include a nucleic acid sequence capable of encoding a Cnx or ERp57 polypeptide and/or a fragment, derivative, homologue or variant of this.

Where reference is made to a Cnx nucleic acid, this should be taken as a reference to any member of the Cnx family of nucleic acids.

Of particular interest are Cnx nucleic acids derived from the genes in the group consisting of: Mouse Gene ID: 12330, Rat Gene ID: 29144, Dog Gene ID: 403908, Cat Gene ID: 101085686 and Horse Gene ID: 100067402.

For example, the Cnx nucleic acid may comprise a human Cnx sequence.

Where reference is made to a ERp57 nucleic acid, this should be taken as a reference to any member of the ERp57 family of nucleic acids.

Of particular interest are ERp57 nucleic acids derived from the genes in the group consisting of: *Homo sapiens* GeneID: 2923, *Mus musculus* GeneID: 14827, *Rattus nor-*

*vegicus* GeneID: 29468, *Bos taurus* GeneID: 281803, *Equus caballus* GeneID: 100056198, *Felis catus* GeneID: 101097245 and *Canis lupus familiaris* GeneID: 478279.

Cnx or ERp57 nucleic acids may be used for a variety of means. The expression of Cnx or ERp57 nucleic acids may be detected for diagnosis or detection of cancer, in particular breast or liver cancer. Cnx and ERp57 nucleic acids may also be used for the expression or production of Cnx and ERp57 polypeptides.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

It will be understood by the skilled person that numerous nucleotide sequences can encode the same polypeptide as a result of the degeneracy of the genetic code.

As used herein, the term "nucleotide sequence" refers to nucleotide sequences, oligonucleotide sequences, polynucleotide sequences and variants, homologues, fragments and derivatives thereof (such as portions thereof). The nucleotide sequence may be DNA or RNA of genomic or synthetic or recombinant origin which may be double-stranded or single-stranded whether representing the sense or antisense strand or combinations thereof. The term nucleotide sequence may be prepared by use of recombinant DNA techniques (for example, recombinant DNA).

The term "nucleotide sequence" may means DNA.

Other Nucleic Acids

We also provide nucleic acids which are fragments, homologues, variants or derivatives of Cnx or ERp57 nucleic acids.

The terms "variant", "homologue", "derivative" or "fragment" in relation to Cnx and ERp57 nucleic acid include any substitution of, variation of, modification of, replacement of, deletion of or addition of one (or more) nucleic acids from or to the sequence of a Cnx or ERp57 nucleotide sequence. Unless the context admits otherwise, references to "Cnx" and "ERp57" include references to such variants, homologues, derivatives and fragments of Cnx or ERp57, as the case may be.

The resultant nucleotide sequence may encode a polypeptide having any one or more Cnx or ERp57 activity. The term "homologue" may be intended to cover identity with respect to structure and/or function such that the resultant nucleotide sequence encodes a polypeptide which has Cnx or ERp57 activity. For example, a homologue etc of Cnx or ERp57 may have a increased expression level in breast or liver cancer cells compared to normal breast or liver cells.

With respect to sequence identity (i.e. similarity), there may be at least 70%, at least 75%, at least 85% or at least 90% sequence identity. There may be at least 95%, such as at least 98%, sequence identity to a relevant sequence. These terms also encompass allelic variations of the sequences.

Variants, Derivatives and Homologues

Cnx or ERp57 nucleic acid variants, fragments, derivatives and homologues may comprise DNA or RNA. They may be single-stranded or double-stranded. They may also be polynucleotides which include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of this document, it is to be understood that the polynucleotides may be modified by any method available in the art. Such modifications may be carried out in order to enhance the in vivo activity or life span of polynucleotides of interest.

Where the polynucleotide is double-stranded, both strands of the duplex, either individually or in combination, are encompassed by the methods and compositions described here. Where the polynucleotide is single-stranded, it is to be understood that the complementary sequence of that polynucleotide is also included.

The terms "variant", "homologue" or "derivative" in relation to a nucleotide sequence include any substitution of, variation of, modification of, replacement of, deletion of or addition of one (or more) nucleic acid from or to the sequence. Said variant, homologues or derivatives may code for a polypeptide having biological activity. Such fragments, homologues, variants and derivatives of Cnx or ERp57 may comprise modulated activity, as set out above.

As indicated above, with respect to sequence identity, a "homologue" may have at least 5% identity, at least 10% identity, at least 15% identity, at least 20% identity, at least 25% identity, at least 30% identity, at least 35% identity, at least 40% identity, at least 45% identity, at least 50% identity, at least 55% identity, at least 60% identity, at least 65% identity, at least 70% identity, at least 75% identity, at least 80% identity, at least 85% identity, at least 90% identity, or at least 95% identity to the relevant sequence.

There may be at least 95% identity, at least 96% identity, at least 97% identity, at least 98% identity or at least 99% identity. Nucleotide identity comparisons may be conducted as described above. A sequence comparison program which may be used is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

Hybridisation

We further describe nucleotide sequences that are capable of hybridising selectively to any of the sequences presented herein, or any variant, fragment or derivative thereof, or to the complement of any of the above. Nucleotide sequences may be at least 15 nucleotides in length, such as at least 20, 30, 40 or 50 nucleotides in length.

The term "hybridization" as used herein shall include "the process by which a strand of nucleic acid joins with a complementary strand through base pairing" as well as the process of amplification as carried out in polymerase chain reaction technologies.

Polynucleotides capable of selectively hybridising to the nucleotide sequences presented herein, or to their complement, may be at least 40% homologous, at least 45% homologous, at least 50% homologous, at least 55% homologous, at least 60% homologous, at least 65% homologous, at least 70% homologous, at least 75% homologous, at least 80% homologous, at least 85% homologous, at least 90% homologous, or at least 95% homologous to the corresponding nucleotide sequences presented herein. Such polynucleotides may be generally at least 70%, at least 80 or 90% or at least 95% or 98% homologous to the corresponding nucleotide sequences over a region of at least 20, such as at least 25 or 30, for instance at least 40, 60 or 100 or more contiguous nucleotides.

The term "selectively hybridizable" means that the polynucleotide used as a probe is used under conditions where a target polynucleotide is found to hybridize to the probe at a level significantly above background. The background hybridization may occur because of other polynucleotides present, for example, in the cDNA or genomic DNA library being screening. In this event, background implies a level of signal generated by interaction between the probe and a non-specific DNA member of the library which is less than 10 fold, such as less than 100 fold as intense as the specific interaction observed with the target DNA. The intensity of interaction may be measured, for example, by radiolabelling the probe, e.g. with $^{32}P$ or $^{33}P$ or with non-radioactive probes (e.g., fluorescent dyes, biotin or digoxigenin).

Hybridization conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego CA), and confer a defined "stringency" as explained below.

Maximum stringency typically occurs at about Tm-5° C. (5° C. below the Tm of the probe); high stringency at about 5° C. to 10° C. below Tm; intermediate stringency at about 10° C. to 20° C. below Tm; and low stringency at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

We provide nucleotide sequences that may be able to hybridise to the Cnx or ERp57 nucleic acids, fragments, variants, homologues or derivatives under stringent conditions (e.g. 65° C. and 0.1×SSC (1×SSC=0.15 M NaCl, 0.015 M $Na_3$ Citrate pH 7.0)).

Generation of Homologues, Variants and Derivatives

Polynucleotides which are not 100% identical to the relevant sequences but which are also included, as well as homologues, variants and derivatives of Cnx or ERp57 can be obtained in a number of ways.

Other variants of the sequences may be obtained for example by probing DNA libraries made from a range of individuals, for example individuals from different populations. For example, Cnx or ERp57 homologues may be identified from other individuals, or other species. Further recombinant Cnx or ERp57 nucleic acids and polypeptides may be produced by identifying corresponding positions in the homologues, and synthesising or producing the molecule as described elsewhere in this document.

In addition, other viral/bacterial, or cellular homologues of Cnx or ERp57, particularly cellular homologues found in mammalian cells (e.g. rat, mouse, bovine and primate cells), may be obtained and such homologues and fragments thereof in general will be capable of selectively hybridising to human Cnx or ERp57. Such homologues may be used to design non-human Cnx or ERp57 nucleic acids, fragments, variants and homologues. Mutagenesis may be carried out by means known in the art to produce further variety.

Sequences of Cnx or ERp57 homologues may be obtained by probing cDNA libraries made from or genomic DNA libraries from other animal species, and probing such libraries with probes comprising all or part of any of the Cnx or ERp57 nucleic acids, fragments, variants and homologues, or other fragments of Cnx or ERp57 under conditions of medium to high stringency.

Similar considerations apply to obtaining species homologues and allelic variants of the polypeptide or nucleotide sequences disclosed here.

Variants and strain/species homologues may also be obtained using degenerate PCR which will use primers designed to target sequences within the variants and homologues encoding conserved amino acid sequences within the sequences of the Cnx or ERp57 nucleic acids. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences. It will be appreciated by the skilled person that overall nucleotide homology between sequences from distantly related organisms is likely to be very low and thus in these situations degenerate PCR may be the method of choice rather than screening libraries with labelled fragments the Cnx or ERp57 sequences.

In addition, homologous sequences may be identified by searching nucleotide and/or protein databases using search algorithms such as the BLAST suite of programs.

Alternatively, such polynucleotides may be obtained by site directed mutagenesis of characterised sequences, for example, Cnx or ERp57 nucleic acids, or variants, homologues, derivatives or fragments thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

The polynucleotides described here may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 8, 9, 10, or 15, such as at least 20, for example at least 25, 30 or 40 nucleotides in length, and are also encompassed by the term "polynucleotides" as used herein.

Polynucleotides such as a DNA polynucleotides and probes may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Primers comprising fragments of Cnx or ERp57 are particularly useful in the methods of detection of Cnx or ERp57 expression, such as up-regulation of Cnx or ERp57 expression, for example, as associated with breast or liver cancer. Suitable primers for amplification of Cnx or ERp57 may be generated from any suitable stretch of Cnx or ERp57. Primers which may be used include those capable of amplifying a sequence of Cnx or ERp57 which is specific, i.e., does not have significant homology to YAP for example.

Although Cnx or ERp57 may be provided on their own, they are most usefully provided as primer pairs, comprising a forward primer and a reverse primer.

Longer polynucleotides will generally be produced using recombinant means, for example using a PCR (polymerase chain reaction) cloning techniques. This will involve making a pair of primers (e.g. of about 15 to 30 nucleotides), bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector Polynucleotides or primers may carry a revealing label. Suitable labels include radioisotopes such as $^{32}P$ or $^{35}S$, digoxigenin, fluorescent dyes, enzyme labels, or other protein labels such as biotin. Such labels may be added to polynucleotides or primers and may be detected using by techniques known per se. Polynucleotides or primers or fragments thereof labelled or unlabeled may be used by a person skilled in the art in nucleic acid-based tests for detecting or sequencing polynucleotides in the human or animal body.

Such tests for detecting generally comprise bringing a biological sample containing DNA or RNA into contact with a probe comprising a polynucleotide or primer under hybridising conditions and detecting any duplex formed between the probe and nucleic acid in the sample. Such detection may be achieved using techniques such as PCR or by immobilising the probe on a solid support, removing nucleic acid in the sample which is not hybridised to the probe, and then detecting nucleic acid which has hybridised to the probe. Alternatively, the sample nucleic acid may be immobilised on a solid support, and the amount of probe bound to such a support can be detected. Suitable assay methods of this and other formats can be found in for example WO89/03891 and WO90/13667.

Tests for sequencing nucleotides, for example, the Cnx or ERp57 nucleic acids, involve bringing a biological sample containing target DNA or RNA into contact with a probe comprising a polynucleotide or primer under hybridising conditions and determining the sequence by, for example the Sanger dideoxy chain termination method (see Sambrook et al.).

Such a method generally comprises elongating, in the presence of suitable reagents, the primer by synthesis of a strand complementary to the target DNA or RNA and selectively terminating the elongation reaction at one or more of an A, C, G or T/U residue; allowing strand elongation and termination reaction to occur; separating out according to size the elongated products to determine the sequence of the nucleotides at which selective termination has occurred. Suitable reagents include a DNA polymerase enzyme, the deoxynucleotides dATP, dCTP, dGTP and dTTP, a buffer and ATP. Dideoxynucleotides are used for selective termination.

Detection and Diagnostic Methods
Detection of Expression of Cnx or ERp57

We show in the Examples that the expression of Cnx/ERp57 in breast and liver cancer tissue is up-regulated when compared to normal breast and liver tissue.

Accordingly, we provide for a method of diagnosis of cancer, including breast and liver cancer such as metastatic, aggressive or invasive breast and liver cancer, comprising detecting modulation of expression of Cnx or ERp57, such as up-regulation of expression of Cnx or ERp57 in a cell or tissue of an individual.

Detection of Cnx or ERp57 expression, activity or amount may be used to provide a method of determining the proliferative state of a cell. Thus, a proliferative cell is one with high levels of Cnx or ERp57 expression, activity or amount compared to a normal cell. Similarly, a non-proliferative cell may be one with low levels Cnx or ERp57 expression, activity or amount compared to a normal cell.

Such detection may also be used to determine whether a cell will become invasive or aggressive. Thus, detection of a high level of Cnx or ERp57 expression, amount or activity of Cnx or ERp57 in the cell may indicate that the cell is likely to be or become aggressive, metastatic or invasive. Similarly, if a cell has a low level of Cnx or ERp57 expression, amount or activity, the cell is not or is not likely to be aggressive, metastatic or invasive.

It will be appreciated that as the level of Cnx or ERp57 varies with the aggressiveness of a tumour, that detection of Cnx or ERp57 expression, amount or activity may also be used to predict a survival rate of an individual with cancer, i.e., high levels of Cnx or ERp57 indicating a lower survival rate or probability and low levels of Cnx or ERp57 indicating a higher survival rate or probability, both as compared to individuals or cognate populations with normal levels of Cnx or ERp57. Detection of expression, amount or activity of Cnx or ERp57 may therefore be used as a method of prognosis of an individual with cancer.

Detection of Cnx or ERp57 expression, amount or level may be used to determine the likelihood of success of a particular therapy in an individual with a cancer. It may be used in a method of determining whether a tumour in an individual is, or is likely to be, an invasive or metastatic tumour.

The diagnostic methods described in this document may be combined with the therapeutic methods described. Thus, we provide for a method of treatment, prophylaxis or alleviation of cancer in an individual, the method comprising detecting modulation of expression, amount or activity of Cnx or ERp57 in a cell of the individual and administering an appropriate therapy to the individual based on the aggressiveness of the tumour.

Typically, physical examination of the breast or liver is used for the detection of breast or liver cancer. A biopsy of the tumour is typically taken for histopathological examination for the diagnosis of breast or liver cancer. Detection of Cnx or ERp57 expression, amount or activity can be used to diagnose, or further confirm the diagnosis of, breast or liver cancer, along with the standard histopathological procedures. This may be especially useful when the histopathological analysis does not yield a clear result.

The presence and quantity of Cnx or ERp57 polypeptides and nucleic acids may be detected in a sample as described in further detail below. Thus, the Cnx or ERp57 associated diseases, including breast and liver cancer, can be diagnosed by methods comprising determining from a sample derived from a subject an abnormally decreased or increased expression, amount or activity, such as a increased expression, amount or activity, of the Cnx or ERp57 polypeptide or Cnx or ERp57 mRNA.

The sample may comprise a cell or tissue sample from an organism or individual suffering or suspected to be suffering from a disease associated with increased, reduced or otherwise abnormal Cnx or ERp57 expression, amount or activity, including spatial or temporal changes in level or pattern of expression, amount or activity. The level or pattern of expression, amount or activity of Cnx or ERp57 in an organism suffering from or suspected to be suffering from such a disease may be usefully compared with the level or pattern of expression, amount or activity in a normal organism as a means of diagnosis of disease.

The sample may comprise a cell or tissue sample from an individual suffering or suspected to be suffering from breast or liver cancer, such as a breast or liver tissue or cell sample.

In some embodiments, an increased level of expression, amount or activity of Cnx or ERp57 is detected in the sample. The level of Cnx or ERp57 may be increased to a significant extent when compared to normal cells, or cells known not to be cancerous. Such cells may be obtained from the individual being tested, or another individual, such as those matched to the tested individual by age, weight, lifestyle, etc.

In some embodiments, the level of expression, amount or activity of Cnx or ERp57 is increased by 10%, 20%, 30% or 40% or more. In some embodiments, the level of expression, amount or activity of Cnx or ERp57 is increased by 45% or more, such as 50% or more, as judged by cDNA hybridisation.

The expression, amount or activity of Cnx or ERp57 may be detected in a number of ways, as known in the art, and as described in further detail below. Typically, the amount of Cnx or ERp57 in a sample of tissue from an individual is measured, and compared with a sample from an unaffected individual. Both Cnx or ERp57 nucleic acid, as well as Cnx or ERp57 polypeptide levels may be measured.

Detection of the amount, activity or expression of Cnx or ERp57 may be used to grade breast or liver cancer. For example, a high level of amount, activity or expression of Cnx or ERp57 may indicate an aggressive, invasive or metastatic cancer. Similarly, a low level of amount, activity or expression of Cnx or ERp57 may indicate a non-aggressive, non-invasive or non-metastatic cancer. Such a grading system may be used in conjunction with established grading systems Measuring Expression of Cnx or ERp57 at the RNA Level Levels of Cnx or ERp57 gene expression may be determined using a number of different techniques.

Cnx or ERp57 gene expression can be detected at the RNA level.

In one embodiment therefore, we disclose a method of detecting the presence of a nucleic acid comprising a Cnx or ERp57 nucleic acid in a sample, by contacting the sample with at least one nucleic acid probe which is specific for the Cnx or ERp57 nucleic acid and monitoring said sample for the presence of the Cnx or ERp57 nucleic acid. For example, the nucleic acid probe may specifically bind to the Cnx or ERp57 nucleic acid, or a portion of it, and binding between the two detected; the presence of the complex itself may also be detected.

Thus, in one embodiment, the amount of Cnx or ERp57 nucleic acid in the form of Cnx or ERp57 mRNA may be measured in a sample. Cnx or ERp57 mRNA may be assayed by in situ hybridization, Northern blotting and reverse transcriptase-polymerase chain reaction. Nucleic acid sequences may be identified by in situ hybridization, Southern blotting, single strand conformational polymorphism, PCR amplification and DNA-chip analysis using specific primers. (Kawasaki, 1990; Sambrook, 1992; Lichter et al, 1990; Orita et al, 1989; Fodor et al., 1993; Pease et al., 1994).

Cnx or ERp57 RNA may be extracted from cells using RNA extraction techniques including, for example, using acid phenol/guanidine isothiocyanate extraction (RNAzol B; Biogenesis), or RNeasy RNA preparation kits (Qiagen). Typical assay formats utilising ribonucleic acid hybridisation include nuclear run-on assays, RT-PCR and RNase protection assays (Melton et al., *Nuc. Acids Res.* 12:7035. Methods for detection which can be employed include radioactive labels, enzyme labels, chemiluminescent labels, fluorescent labels and other suitable labels.

Each of these methods allows quantitative determinations to be made, and are well known in the art. Decreased or increased Cnx or ERp57 expression, amount or activity can therefore be measured at the RNA level using any of the methods well known in the art for the quantitation of polynucleotides. Any suitable probe from a Cnx or ERp57 sequence, for example, any portion of a suitable human Cnx or ERp57 sequence may be used as a probe.

Typically, RT-PCR is used to amplify RNA targets. In this process, the reverse transcriptase enzyme is used to convert RNA to complementary DNA (cDNA) which can then be amplified to facilitate detection.

Many DNA amplification methods are known, most of which rely on an enzymatic chain reaction (such as a polymerase chain reaction, a ligase chain reaction, or a self-sustained sequence replication) or from the replication of all or part of the vector into which it has been cloned.

Many target and signal amplification methods have been described in the literature, for example, general reviews of these methods in Landegren, U. et al., *Science* 242:229-237 (1988) and Lewis, R., *Genetic Engineering News* 10:1, 54-55 (1990).

For example, the polymerase chain reaction may be employed to detect Cnx or ERp57 mRNA.

The "polymerase chain reaction" or "PCR" is a nucleic acid amplification method described inter alia in U.S. Pat. Nos. 4,683,195 and 4,683,202. PCR can be used to amplify any known nucleic acid in a diagnostic context (Mok et al., 1994, *Gynaecologic Oncology* 52:247-252). Self-sustained sequence replication (3SR) is a variation of TAS, which involves the isothermal amplification of a nucleic acid template via sequential rounds of reverse transcriptase (RT), polymerase and nuclease activities that are mediated by an enzyme cocktail and appropriate oligonucleotide primers (Guatelli et al., 1990, *Proc. Natl. Acad. Sci. USA* 87:1874). Ligation amplification reaction or ligation amplification system uses DNA ligase and four oligonucleotides, two per target strand. This technique is described by Wu, D. Y. and Wallace, R. B., 1989, *Genomics* 4:560. In the QI3 Replicase technique, RNA replicase for the bacteriophage Q3, which replicates single-stranded RNA, is used to amplify the target DNA, as described by Lizardi et al., 1988, *Bio/Technology* 6:1197.

A PCR procedure basically involves: (1) treating extracted DNA to form single-stranded complementary strands; (2) adding a pair of oligonucleotide primers, wherein one primer of the pair is substantially complementary to part of the sequence in the sense strand and the other primer of each pair is substantially complementary to a different part of the same sequence in the complementary antisense strand; (3) annealing the paired primers to the complementary sequence; (4) simultaneously extending the annealed primers from a 3' terminus of each primer to synthesize an extension product complementary to the strands annealed to each primer wherein said extension products after separation from the complement serve as templates for the synthesis of an extension product for the other primer of each pair; (5) separating said extension products from said templates to produce single-stranded molecules; and (6) amplifying said single-stranded molecules by repeating at least once said annealing, extending and separating steps.

Reverse transcription-polymerase chain reaction (RT-PCR) may be employed. Quantitative RT-PCR may also be used. Such PCR techniques are well known in the art, and may employ any suitable primer from a Cnx or ERp57 sequence.

Alternative amplification technology can also be exploited. For example, rolling circle amplification (Lizardi et al., 1998, *Nat Genet* 19:225) is an amplification technology available commercially (RCAT™) which is driven by DNA polymerase and can replicate circular oligonucleotide probes with either linear or geometric kinetics under isothermal conditions. A further technique, strand displacement amplification (SDA; Walker et al., 1992, *Proc. Natl. Acad. Sci. USA* 80:392) begins with a specifically defined sequence unique to a specific target.

Measuring Expression of Cnx or ERp57 at the Polypeptide Level

Cnx or ERp57 expression can be detected at the polypeptide level.

In a further embodiment, therefore, Cnx or ERp57 expression, amount or activity may be detected by detecting the presence or amount of Cnx or ERp57 polypeptide in a sample. This may be achieved by using molecules which bind to Cnx or ERp57 polypeptide. Suitable molecules/agents which bind either directly or indirectly to the Cnx or ERp57 polypeptide in order to detect its presence include naturally occurring molecules such as peptides and proteins, for example antibodies, or they may be synthetic molecules.

Thus, we disclose a method of detecting the presence of a TA Cnx or ERp57 Z polypeptide by contacting a cell sample with an antibody capable of binding the polypeptide and monitoring said sample for the presence of the polypeptide.

For example, the Cnx or ERp57 polypeptide may be detected using an anti-Cnx or anti-ERp57 antibody. Such antibodies may be made by means known in the art.

This may conveniently be achieved by monitoring the presence of a complex formed between the antibody and the polypeptide, or monitoring the binding between the polypeptide and the antibody. Methods of detecting binding between two entities are known in the art, and include FRET (fluorescence resonance energy transfer), surface plasmon resonance, etc.

Standard laboratory techniques such as immunoblotting as described above can be used to detect altered levels of Cnx or ERp57 protein, as compared with untreated cells in the same cell population.

Gene expression may also be determined by detecting changes in post-translational processing of Cnx or ERp57 polypeptides or post-transcriptional modification of Cnx or ERp57 nucleic acids. For example, differential phosphorylation of Cnx or ERp57 polypeptides, the cleavage of Cnx or ERp57 polypeptides or alternative splicing of Cnx or ERp57 RNA, and the like may be measured. Levels of expression of gene products such as Cnx or ERp57 polypeptides, as well as their post-translational modification, may be detected using proprietary protein assays or techniques such as 2D polyacrylamide gel electrophoresis.

Assay techniques that can be used to determine levels of Cnx or ERp57 protein in a sample derived from a host are well-known to those of skill in the art. Antibodies can be assayed for immunospecific binding by any method known in the art.

The immunoassays which can be used include but are not limited to competitive and non-competitive assay systems using techniques such as western blots, radioimmunoassays, ELISA, sandwich immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays. Such assays are routine in the art (see, for example, Ausubel et al., eds, 1994, *Current Protocols in Molecular Biology*, Vol. 1, John Wiley & Sons, Inc., New York, which is incorporated by reference herein in its entirety).

The specimen may be assayed for polypeptides/proteins by immunohistochemical and immunocytochemical staining (see generally Stites and Ten, Basic and Clinical Immunology, Appleton and Lange, 1994), ELISA, RIA, immunoblots, Western blotting, immunoprecipitation, functional assays and protein truncation test. Other assay methods include radioimmunoassays, competitive-binding assays, Western Blot analysis and ELISA assays.

ELISA assays are well known to those skilled in the art. Both polyclonal and monoclonal antibodies may be used in the assays. Where appropriate other immunoassays, such as radioimmunoassays (RIA) may be used as are known to those in the art. Available immunoassays are extensively described in the patent and scientific literature. See, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521 as well as Sambrook et al, 1992.

Diagnostic Kits

We also provide diagnostic kits for detecting breast or liver cancer in an individual, or susceptibility to breast or liver cancer in an individual.

The diagnostic kit may comprise means for detecting expression, amount or activity of Cnx or ERp57 in the individual, by any means as described in this document. The diagnostic kit may therefore comprise any one or more of the following: a Cnx or ERp57 polynucleotide or a fragment thereof; a complementary nucleotide sequence to Cnx or ERp57 nucleic acid or a fragment thereof; a Cnx or ERp57 polypeptide or a fragment thereof, or an antibody to a Cnx or ERp57.

The diagnostic kit may comprise instructions for use, or other indicia. The diagnostic kit may further comprise means for treatment or prophylaxis of breast or liver cancer, such as any of the compositions described in this document, or any means known in the art for treating breast or liver cancer. In particular, the diagnostic kit may comprise an Cnx/ERp57 inhibitor as described, for example obtained by screening. The diagnostic kit may comprise a therapeutic drug such as Tamoxifen (Nolvadex) or its variants such as tamoxifen, tamoxifen citrate or any other antiestrogen or estrogen blocker. The therapeutic drug may also comprise an anti-Cnx or anti-ERp57 antibody.

Prophylactic and Therapeutic Methods

We disclose methods of treating an abnormal conditions, such as breast or liver cancer, related to excessive amounts of Cnx or ERp57 expression or activity. Methods of preventing breast or liver cancer (i.e., prophylaxis) also suitably employ the same or similar approaches.

In general terms, our methods involve manipulation of cancer cells, by modulating (such as down-regulating) the expression, amount or activity of Cnx or ERp57 in the cell. A step of detecting modulated Cnx or ERp57 expression, amount or activity in a cell may be conducted before or after the manipulation step. The detection step may detect up-regulated or down-regulated Cnx or ERp57 expression, amount or activity. Any of the methods of modulating or down-regulating Cnx or ERp57, as described in detail elsewhere in this document, may be used.

The method may comprise exposing the cell to an siRNA or shRNA or an anti-Cnx or anti-ERp57 antibody capable of specifically binding to Cnx or ERp57.

According to our methods, the cancer cell becomes non-cancerous or the invasive or metastatic cancer cell becomes non-invasive or non-metastatic as a result of the manipulation. The cancer may in particular comprise breast or liver cancer. It may comprise invasive or metastatic cancer such as Invasive Ductal Carcinoma (IDC).

As Cnx and ERp57 is associated with aggressiveness and invasiveness of cancer, the level of Cnx or ERp57 may be detected in a cell of an individual with cancer, in a cancer or non-cancer cell, and the aggressiveness of the cancer assessed. A high level of Cnx or ERp57 amount, expression or activity compared with a normal cell indicates an aggressive or invasive cancer, and a stronger or harsher therapy may therefore be required and chosen. Similarly, a lower level may indicate a less aggressive or invasive therapy.

The approaches described here may be used for therapy of any Cnx or ERp57 related disease in general. Cnx or ERp57 related diseases include proliferative diseases and in particular include cancer. For example, a Cnx or ERp57 related disease may include breast or liver cancer, such as metastatic, invasive or aggressive breast or liver cancer.

A Cnx or ERp57 related disease is defined as being "treated" if a condition associated with the disease is significantly inhibited (i.e., by 50% or more) relative to controls. The inhibition may be by at least 75% relative to controls, such as by 90%, by 95% or 100% relative to controls. The condition may comprise cell proliferation, or it may comprise cell cycle time, cell number, cell migration, cell invasiveness, etc. By the term "treatment" we mean to also include prophylaxis or alleviation of cancer.

Cnx and ERp57 polypeptides represent a target for inhibition of its function for therapy, particularly in tumour cells and other proliferative cells.

The term proliferative disorder is used herein in a broad sense to include any disorder that requires control of the cell cycle. In particular, a proliferative disorder includes malignant and pre-neoplastic disorders. The methods and compositions described here are especially useful in relation to treatment or diagnosis of adenocarcinomas such as: small cell lung cancer, and cancer of the kidney, uterus, prostrate, bladder, ovary, colon and breast. For example, malignancies which may be treatable include acute and chronic leukemias, lymphomas, myelomas, sarcomas such as Fibrosarcoma, myxosarcoma, liposarcoma, lymphangioendotheliosarcoma, angiosarcoma, endotheliosarcoma, chondrosarcoma, osteogenic sarcoma, chordoma, lymphangiosarcoma, synovioma, mesothelioma, leimyosarcoma, rhabdomyosarcoma, colon carcinoma, ovarian cancer, glioma, prostate cancer, pancreatic cancer, breast cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, choriocarcinoma, renal cell carcinoma, hepatoma, bile duct carcinoma seminoma, embryonal carcinoma, cervical cancer, testicular tumour, lung carcinoma, small cell lung carcinoma, bladder carcinoma, epithelial carcinoma, glioma, astrocytoma, ependymoma, pinealoma, hemangioblastoma, acoustic neuoma, medulloblastoma, craniopharyngioma, oligodendroglioma, menangioma, melanoma, neutroblastoma and retinoblastoma.

One possible approach for therapy of such disorders is to express anti-sense constructs directed against Cnx or ERp57 polynucleotides as described here, and administering them to tumour cells, to inhibit gene function and prevent the tumour cell from growing or progressing.

Anti-sense constructs may be used to inhibit gene function to prevent growth or progression in a proliferative cell. Antisense constructs, i.e., nucleic acid, such as RNA, constructs complementary to the sense nucleic acid or mRNA, are described in detail in U.S. Pat. No. 6,100,090 (Monia et al.), and Neckers et al., 1992, *Crit Rev Oncog* 3(1-2):175-231, the teachings of which document are specifically incorporated by reference.

In a particular example, breast and liver cancer may be treated or prevented by reducing the amount, expression or activity of Cnx or ERp57 in whole or in part, for example by siRNAs capable of binding to and destroying Cnx or ERp57 mRNA. We specifically provide for an Cnx/ERp57 inhibitor which downregulates Cnx or ERp57 by RNA interference. The Cnx/ERp57 inhibitor may comprise a Small Interfering RNA (siRNA) or Short Hairpin RNA (shRNA).

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., Nature 391:806-811 (1998). Other methods of PTGS are known and include, for example, introduction of a transgene or virus. Generally, in PTGS, the transcript of the silenced gene is synthesised but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the Cnx or ERp57 nucleic acid sequence.

Alternatively, double-stranded (ds) RNA is a powerful way of interfering with gene expression in a range of organisms that has recently been shown to be successful in mammals (Wianny and Zernicka-Goetz, 2000, *Nat Cell Biol* 2:70-75). Double stranded RNA corresponding to the sequence of a Cnx or ERp57 polynucleotide can be introduced into or expressed in oocytes and cells of a candidate organism to interfere with Cnx/ERp57 activity.

Other methods of modulating Cnx or ERp57 gene expression are known to those skilled in the art and include dominant negative approaches. Thus, another approach is to use non-functional variants of Cnx or ERp57 polypeptide in this document that compete with the endogenous gene product resulting in inhibition of function.

Cnx or ERp57 gene expression may also be modulated by as introducing peptides or small molecules which inhibit gene expression or functional activity. Thus, compounds identified by the assays described here as binding to or modulating, such as down-regulating, the amount, activity or expression of Cnx or ERp57 polypeptide may be administered to tumour or proliferative cells to prevent the function of Cnx or ERp57 polypeptide. Such a compound may be administered along with a pharmaceutically acceptable carrier in an amount effective to down-regulate expression or activity of Cnx or ERp57, or by activating or down-regulating a second signal which controls Cnx or ERp57 expression, activity or amount, and thereby alleviating the abnormal condition.

Suitable antibodies against Cnx or ERp57 polypeptide as described herein may also be used as therapeutic agents.

Alternatively, gene therapy may be employed to control the endogenous production of Cnx or ERp57 by the relevant cells such as breast cells in the subject. For example, a polynucleotide encoding a Cnx or ERp57 siRNA or a portion of this may be engineered for expression in a replication defective retroviral vector, as discussed below. The retroviral expression construct may then be isolated and introduced into a packaging cell transduced with a retroviral plasmid vector containing RNA encoding an anti-Cnx or anti-ERp57 siRNA such that the packaging cell now produces infectious viral particles containing the sequence of interest. These producer cells may be administered to a subject for engineering cells in vivo and regulating expression of the Cnx or ERp57 polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

Breast cell specific reduction of Cnx or ERp57 levels may be achieved by targeted administration, i.e., applying the treatment only to the breast cells and not other cells. However, in other embodiments, down-regulation of Cnx or ERp57 expression in breast cells (and not substantially in other cell or tissue types) is employed. Such methods may advantageously make use of breast specific expression vectors, for breast specific expression of for example siRNAs, as described in further detail below.

Breast Cancer

According to the methods and compositions described here, Cnx or ERp57 is useful for diagnosing or treating breast cancer. Where this document refers to "cancer", this should be taken to include metastatic, aggressive or invasive cancer.

There are several types of breast cancer. The most common is ductal carcinoma, which begins in the lining of the milk ducts of the breast. Another type, lobular carcinoma, begins in the lobules where breast milk is produced. If a malignant tumour invades nearby tissue, it is known as infiltrating or invasive cancer. When breast cancer spreads outside the breast, cancer cells often are found in the lymph nodes under the arm. Breast cancer cells may spread beyond the breast such as to other lymph nodes, the bones, liver, or lungs.

The recognised stages of breast cancer comprise:

Stage 0: Very early breast cancer. This type of cancer has not spread within or outside the breast. It is sometimes called DCIS, LCIS, or breast cancer in situ or non-invasive cancer.

Stage I: The cancer is no larger than about 1 inch in size and has not spread outside the breast. (also described as early breast cancer.)

Stage II: The presence of any of the following: the cancer is no larger than 1 inch, but has spread to the lymph nodes under the arm; the cancer is between 1 and 2 inches. It may or may not have spread to the lymph nodes under the arm; the cancer is larger than 2 inches, but has not spread to the lymph nodes under the arm.

Stage III and Stage IIIA: The presence of any of the following: the cancer is smaller than 2 inches and has spread to the lymph nodes under the arm, the cancer also is spreading further to other lymph nodes; the cancer is larger than 2 inches and has spread to the lymph nodes under the arm.

Stage IIIB: The presence of any of the following: the cancer has spread to tissues near the breast (skin, chest wall, including the ribs and the muscles in the chest); the cancer has spread to lymph nodes inside the chest wall along the breast bone.

Stage IV: The cancer has spread to other parts of the body, most often the bones, lungs, liver, or brain. Or, the tumour has spread locally to the skin and lymph nodes inside the neck, near the collarbone.

Inflammatory Breast Cancer: Inflammatory breast cancer is a rare, but very serious, aggressive type of breast cancer. The breast may look red and feel warm. There may be ridges, welts, or hives on the breast; or the skin may look wrinkled. It is sometimes misdiagnosed as a simple infection.

Recurrent Breast Cancer: Recurrent disease means that the cancer has come back (recurred) after it has been treated. It may come back in the breast, in the soft tissues of the chest (the chest wall), or in another part of the body.

Breast Cancer In Situ—DCIS and LCIS

Many breast cancers being found are very early cancers known as breast cancer in situ or noninvasive cancer. Most of these cancers are found by mammography. These very early cell changes may become invasive breast cancer. Two types of breast cancer in situ include the following:

DCIS (ductal carcinoma in situ), which means that abnormal cells are found only in the lining of a milk duct of the breast. The abnormal cells have not spread outside the duct. They have not spread within the breast, beyond the breast, to the lymph nodes under the arm, or to other parts of the body. There are several types of DCIS. If not removed, some types may change over time and become invasive cancers. Some may never become invasive cancers. (DCIS is sometimes called intraductal carcinoma.)

LCIS (lobular carcinoma in situ), which means that abnormal cells are found in the lining of a milk lobule. Although LCIS is not considered to be actual breast cancer at this noninvasive stage, it is a warning sign of increased risk of developing invasive cancer. LCIS is sometimes found when a biopsy is done for another lump or unusual change that is found on a mammogram. Patients with LCIS have a 25 percent chance of developing breast cancer in either breast during the next 25 years.

Microcalcifications are very small specks of calcium that can't be felt, but can be seen on a mammogram. They are formed by rapidly dividing cells. When they are clustered in one area of the breast, this could be an early sign of breast cancer in situ. About half of the breast cancers found by mammography appear as clusters of microcalcifications. The other half appear as lumps.

Diagnosis

Our diagnostic methods may be used in conjunction with any known method of diagnosis of breast cancer, including detecting of mutations in either or both of the known breast cancer genes BRCA1 and BRCA2. Alternatively, or in addition, the diagnosis may be carried out by detection of Her2 expression, for example by use of anti-Her2 antibody.

Treatment

Known treatments for breast cancer may consist of any one or more of the following: Surgery, radiation therapy, chemotherapy, high-dose chemotherapy, hormonal therapy and immunotherapy. Accordingly, any of the treatment methods described here may be combined with any one or more of the preceding known therapies. In addition, any one or more of the following general therapies known to be effective for treatment or alleviation of cancer may be used.

Nonspecific Immunomodulating Agents

Nonspecific immunomodulating agents are substances that stimulate or indirectly augment the immune system. Often, these agents target key immune system cells and cause secondary responses such as increased production of cytokines and immunoglobulins. Two nonspecific immunomodulating agents used in cancer treatment are *Bacillus* Calmette-Guerin (BCG) and levamisole. The Cnx/ERp57 inhibitors described here may be used in conjunction with any of such nonspecific immunomodulating agents.

Biological Response Modifiers

Some antibodies, cytokines, and other immune system substances can be produced in the laboratory for use in cancer treatment. These substances are often called biological response modifiers (BRMs). They alter the interaction between the body's immune defenses and cancer cells to boost, direct, or restore the body's ability to fight the disease. BRMs include interferons, interleukins, colony-stimulating factors, monoclonal antibodies, and vaccines. The Cnx/ERp57 inhibitors described here may be used in conjunction with any of such biological response modifiers.

Interferons (IFN)

There are three major types of interferons—interferon alpha, interferon beta, and interferon gamma; interferon alpha is the type most widely used in cancer treatment.

Interferons can improve the way a cancer patient's immune system acts against cancer cells. In addition, interferons may act directly on cancer cells by slowing their growth or promoting their development into cells with more normal behavior. Some interferons may also stimulate NK cells, T cells, and macrophages, boosting the immune system's anticancer function.

The Cnx/ERp57 inhibitors described here may be used in conjunction with any of such interferons.

Interleukins (IL)

Like interferons, interleukins are cytokines that occur naturally in the body. Many interleukins have been identified; interleukin-2 (IL-2 or aldesleukin) has been the most widely studied in cancer treatment. IL-2 stimulates the growth and activity of many immune cells, such as lymphocytes, that can destroy cancer cells.

The Cnx/ERp57 inhibitors described here may be used in conjunction with any of such interleukins.

Colony-Stimulating Factors (CSFs)

Colony-stimulating factors (CSFs) (sometimes called hematopoietic growth factors) usually do not directly affect tumour cells; rather, they encourage bone marrow stem cells to divide and develop into white blood cells, platelets, and red blood cells. Bone marrow is critical to the body's immune system because it is the source of all blood cells.

G-CSF (filgrastim) and GM-CSF (sargramostim) can increase the number of white blood cells, thereby reducing the risk of infection in patients receiving chemotherapy. G-CSF and GM-CSF can also stimulate the production of stem cells in preparation for stem cell or bone marrow transplants; Erythropoietin can increase the number of red blood cells and reduce the need for red blood cell transfusions in patients receiving chemotherapy; and Oprelvekin can reduce the need for platelet transfusions in patients receiving chemotherapy.

The Cnx/ERp57 inhibitors described here may be used in conjunction with any of such colony-stimulating factors.

Monoclonal Antibodies (MOABs)

Herceptin is used to treat metastatic breast cancer in patients with tumours that produce excess amounts of a protein called HER-2. (Approximately 25 percent of breast cancer tumours produce excess amounts of HER-2). In particular embodiments, the methods of treatment described here may be used in combination with administration of anti-Her2 antibody, for example, Herceptin, to the individual concerned.

The Cnx/ERp57 inhibitors described here may be used in conjunction with any of such monoclonal antibodies.

HER2/Neu

The HER-2/neu (erbB-2) gene product is a 185-kDA transmembrane receptor tyrosine kinase that belongs to the family of receptors for epidermal growth factor. It is described in some detail in Reese, D. M., et al., Stem Cells, 15, 1-8 (1997) which is incorporated herein by reference.

Recently, enormous attention has been given to the importance of HER-2/neu in breast cancer. HER-2/neu is overexpressed in 20-30% of human breast cancers and the increased expression has been associated with poor prognosis. The discovery of this has led to the development of HERCEPTIN, an antibody to HER-2/neu, which in tests has been found to lengthen remission time in metastatic breast cancer. HER-2/neu is a cell-surface receptor that transmits growth signals to the cell nucleus. HERCEPTIN appears to block these signals thereby apparently inhibiting proliferation of cells mediated by HER-2/neu in HER-2/neu positive breast cancer.

Overexpression of HER-2/neu has also been found in a portion of ovarian cancers, gastric cancers, endometrial cancers, salivary cancers, pancreatic cancers, prostate cancers, colorectal cancers, and non-small-cell lung cancers. The other cancers associated with overexpression of HER-2-neu are potentially treatable with HERCEPTIN.

Accordingly, our methods of diagnosis may be combined with detection of overexpression of Her2 in an individual. Likewise, the methods of treatment described here may include administration of Herceptin to an individual, in addition to decreasing activity, amount or expression of Cnx or ERp57. We therefore provide a combination of an Cnx/ERp57 inhibitor, together with an anti-Her2 antibody. We also provide a combination of an anti-Cnx or anti-ERp57 antibody together with an anti-Her2 antibody. In some embodiments, the anti-Her2 antibody comprises Herceptin.

Screening for Cnx/ERp57 Inhibitors

Identifying Cnx or ERp57 Modulators, Agonists and Antagonists

Antagonists, in particular, small molecules may be used to specifically inhibit Cnx or ERp57 for use as Cnx/ERp57 inhibitors.

We therefore disclose Cnx or ERp57 antagonists and small molecule Cnx or ERp57 inhibitors, as well as assays for screening for these. Antagonists of Cnx or ERp57 may be screened by detecting modulation, such as down regulation, of binding or other Cnx or ERp57 activity. Antagonists of Cnx or ERp57 may also be screened by detecting modulation of binding between Cnx and ERp57.

We therefore provide a compound capable of down-regulating the expression, amount or activity of a Cnx or ERp57 polypeptide. Such a compound may be used in the methods and compositions described here for treating or preventing cancer, particularly breast or liver cancer.

Cnx and ERp57 may therefore be used to assess the binding of small molecule substrates and ligands in, for example, cells, cell-free preparations, chemical libraries, and natural product mixtures. These substrates and ligands may be natural substrates and ligands or may be structural or functional mimetics. See Coligan et al., *Current Protocols in Immunology* 1(2):Chapter 5 (1991). Furthermore, screens may be conducted to identify factors which influence the expression of Cnx or ERp57, in particular in breast cells.

In general, the assays for agonists and antagonists rely on determining the effect of candidate molecules on one or more activities of Cnx or ERp57. An assay may involve assaying Cnx or ERp57 activity in the presence of a candidate molecule, and optionally in the absence of the candidate molecule, or in the presence of a molecule known to inhibit or activate a Cnx or ERp57 activity. Assays or modulators of activity of Cnx or ERp57 may be detected by detecting binding of Cnx with another entity, such as a ERp57.

Accordingly, a screen for a modulator of Cnx or ERp57 activity such as a Cnx or ERp57 antagonist may be conducted by providing Cnx and ERp57 polypeptide and detecting the binding between them, in the presence and absence of a candidate molecule. Molecules of interest are those that interrupt, diminish, abolish, disrupt or in any way modulate the binding between Cnx and ERp57.

We have demonstrated that expression of Cnx and ERp57 is increased in breast and liver cancer cells; accordingly, control of Cnx or ERp57 expression may be employed to treat breast or liver cancer and other cancers. Therefore, it is desirous to find compounds and drugs which stimulate the expression and/or activity of Cnx or ERp57, or which can inhibit the function of this protein. In general, agonists and antagonists are employed for therapeutic and prophylactic purposes for any known cancer, in particular, breast or liver cancer.

By "down-regulation" we include any negative effect on the behaviour being studied; this may be total or partial. Thus, where binding is being detected, candidate antagonists are capable of reducing, ameliorating, or abolishing the binding between two entities. The down-regulation of binding (or any other activity) achieved by the candidate molecule may be at least 10%, such as at least 20%, at least 30%, at least 40%, at least 50%, at least 60%, at least 70%, at least 80%, at least 90% or more compared to binding (or which ever activity) in the absence of the candidate molecule. Thus, a candidate molecule suitable for use as an antagonist is one which is capable of reducing by 10% more the binding or other activity.

The term "compound" refers to a chemical compound (naturally occurring or synthesised), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. The compound may be an antibody.

Examples of potential antagonists of Cnx or ERp57 include antibodies, small molecules, nucleotides and their analogues, including purines and purine analogues, oligonucleotides or proteins which are closely related to a binding partner of Cnx or ERp57, e.g., a fragment of the binding partner, or small molecules which bind to the Cnx or ERp57 polypeptide but do not elicit a response, so that the activity of the polypeptide is prevented, etc.

Screening Kits

The materials necessary for such screening to be conducted may be packaged into a screening kit.

Such a screening kit is useful for identifying agonists, antagonists, ligands, receptors, substrates, enzymes, etc. for Cnx or ERp57 polypeptides or compounds which decrease or enhance the production of Cnx or ERp57. The screening kit may comprise: (a) a Cnx or ERp57 polypeptide; (b) a recombinant cell expressing a Cnx or ERp57 polypeptide; or (c) an antibody to Cnx or ERp57 polypeptide. The screening kit may comprise a library. The screening kit may comprise any one or more of the components needed for screening, as described below. The screening kit may optionally comprise instructions for use.

Screening kits may also be provided which are capable of detecting Cnx or ERp57 expression at the nucleic acid level. Such kits may comprise a primer for amplification of Cnx or ERp57, or a pair of primers for amplification. The primer or primers may be chosen from any suitable sequence, for example a portion of the Cnx or ERp57 sequence. Methods of identifying primer sequences are well known in the art, and the skilled person will be able to design such primers with ease. The kits may comprise a nucleic acid probe for Cnx or ERp57 expression, as described in this document. The kits may also optionally comprise instructions for use.

Rational Design

Rational design of candidate compounds likely to be able to interact with Cnx or ERp57 may be based upon structural studies of the molecular shapes of a Cnx or ERp57 polypeptide.

A further means for determining which sites interact with specific other proteins is a physical structure determination, e.g., X-ray crystallography or two-dimensional NMR techniques.

These will provide guidance as to which amino acid residues form molecular contact regions. For a detailed description of protein structural determination, see, e.g., Blundell and Johnson (1976) *Protein Crystallography*, Academic Press, New York.

Polypeptide Binding Assays

Modulators and antagonists of Cnx or ERp57 activity or expression may be identified by any means known in the art.

In their simplest form, the assays may simply comprise the steps of mixing a candidate compound with a solution containing a Cnx or ERp57 polypeptide to form a mixture, measuring activity of Cnx or ERp57 polypeptide in the mixture, and comparing the activity of the mixture to a standard.

Furthermore, molecules may be identified by their binding to Cnx or ERp57, in an assay which detects binding between Cnx or ERp57 and the putative molecule.

One type of assay for identifying substances that bind to a Cnx or ERp57 polypeptide described here involves contacting the Cnx or ERp57 polypeptide, which is immobilised on a solid support, with a non-immobilised candidate substance determining whether and/or to what extent the Cnx or ERp57 polypeptide of interest and candidate substance bind to each other. Alternatively, the candidate substance may be immobilised and the Cnx or ERp57 polypeptide as set out in this document non-immobilised.

The binding of the substance to the Cnx or ERp57 polypeptide can be transient, reversible or permanent. The substance may bind to the polypeptide with a Kd value which is lower than the Kd value for binding to control polypeptides (e.g., polypeptides known to not be involved in cancer growth or progression). The Kd value of the substance may be 2 fold less than the Kd value for binding to control polypeptides, such as a Kd value 100 fold less or a Kd 1000 fold less than that for binding to the control polypeptide.

In an example assay method, the Cnx or ERp57 polypeptide may be immobilised on beads such as agarose beads. Typically this may be achieved by expressing the Cnx or ERp57 polypeptide as a GST-fusion protein in bacteria, yeast or higher eukaryotic cell lines and purifying the GST-Cnx or GST-ERp57 fusion protein from crude cell extracts using glutathione-agarose beads (Smith and Johnson, 1988; Gene 67(10):31-40). As a control, binding of the candidate substance, which is not a GST-fusion protein, to an immobilised polypeptide may be determined in the absence of the Cnx or ERp57 polypeptide. The binding of the candidate substance to the immobilised Cnx or ERp57 polypeptide may then be determined. This type of assay is known in the art as a GST pulldown assay. Again, the candidate substance may be immobilised and the Cnx or ERp57 polypeptide non-immobilised.

It is also possible to perform this type of assay using different affinity purification systems for immobilising one of the components, for example Ni-NTA agarose and histidine-tagged components.

Binding of the polypeptide to the candidate substance may be determined by a variety of methods well-known in the art. For example, the non-immobilised component may be labeled (with for example, a radioactive label, an epitope tag or an enzyme-antibody conjugate). Alternatively, binding may be determined by immunological detection techniques. For example, the reaction mixture can be Western blotted and the blot probed with an antibody that detects the non-immobilised component. ELISA techniques may also be used.

Candidate substances are typically added to a final concentration of from 1 to 1000 nmol/ml, such as from 1 to 100 nmol/ml. In the case of antibodies, the final concentration used is typically from 100 to 500 µg/ml, such as from 200 to 300 µg/ml.

Modulators and antagonists of Cnx or ERp57 may also be identified by detecting modulation of binding between Cnx or ERp57 and any molecule to which this polypeptide binds, or modulation of any activity consequential on such binding or release.

Cell Based Assays

A cell based assay may simply test binding of a candidate compound wherein adherence to the cells bearing the Cnx or ERp57 polypeptide is detected by means of a label directly or indirectly associated with the candidate compound or in an assay involving competition with a labeled competitor.

Further, these assays may test whether the candidate compound results in a signal generated by binding to the Cnx or ERp57 polypeptide, using detection systems appropriate to the cells bearing the polypeptides at their surfaces. Inhibitors of activation are generally assayed in the presence of a known agonist and the effect on activation by the agonist by the presence of the candidate compound is observed. Such a signal could include nuclear localisation, which may be assayed as described in the Examples. Another signal which may be detected is oncogenic activity, which may be assayed by a soft agar assay, as described in the Examples.

Another method of screening compounds utilises eukaryotic or prokaryotic host cells which are stably transformed with recombinant DNA molecules expressing a library of compounds. Such cells, either in viable or fixed form, can be used for standard binding-partner assays. See also Parce et al. (1989) Science 246:243-247; and Owicki et al. (1990) Proc. Nat'l Acad. Sci. USA 87; 4007-4011, which describe sensitive methods to detect cellular responses.

Competitive assays are particularly useful, where the cells expressing the library of compounds are contacted or incubated with a labelled antibody known to bind to a Cnx or ERp57 polypeptide, such as 125 I-antibody, and a test sample such as a candidate compound whose binding affinity to the binding composition is being measured. The bound and free labelled binding partners for the Cnx or ERp57 polypeptide are then separated to assess the degree of binding. The amount of test sample bound is inversely proportional to the amount of labelled antibody binding to the Cnx or ERp57 polypeptide.

Any one of numerous techniques can be used to separate bound from free binding partners to assess the degree of binding. This separation step could typically involve a procedure such as adhesion to filters followed by washing, adhesion to plastic following by washing, or centrifugation of the cell membranes.

The assays may involve exposing a candidate molecule to a cell, such as a breast cell, and assaying expression of Cnx or ERp57 by any suitable means. Molecules which down-regulate the expression of Cnx or ERp57 in such assays may be optionally chosen for further study, and used as drugs to down-regulate Cnx or ERp57 expression. Such drugs may be usefully employed to treat or prevent breast or liver cancer.

cDNA encoding Cnx or ERp57 protein and antibodies to the proteins may also be used to configure assays for detecting the effect of added compounds on the production of Cnx or ERp57 mRNA and protein in cells. For example, an ELISA may be constructed for measuring secreted or cell associated levels of Cnx or ERp57 polypeptide using monoclonal and polyclonal antibodies by standard methods known in the art, and this can be used to discover agents which may inhibit or enhance the production of Cnx or ERp57 protein (also called antagonist or agonist, respectively) from suitably manipulated cells or tissues. Standard methods for conducting screening assays are well understood in the art.

Activity Assays

Assays to detect modulators or antagonists typically involve detecting modulation of any activity of Cnx or ERp57, in the presence, optionally together with detection of modulation of activity in the absence, of a candidate molecule.

Assays which detect specific biological activities of Cnx or ERp57 may also be used. The assays typically involve contacting a candidate molecule (e.g., in the form of a library) with Cnx or ERp57 whether in the form of a polypeptide, a nucleic acid encoding the polypeptide, or a cell, organelle, extract, or other material comprising such, with a candidate modulator. The relevant activity of Cnx or ERp57 (as described below) may be detected, to establish whether the presence of the candidate modulator has any effect.

Promoter binding assays to detect candidate modulators which bind to and/or affect the transcription or expression of Cnx or ERp57 may also be used. Candidate modulators may then be chosen for further study, or isolated for use. Details of such screening procedures are well known in the art, and are for example described in, *Handbook of Drug Screening*, edited by Ramakrishna Seethala, Prabhavathi B. Fernandes (2001, New York, NY, Marcel Dekker, ISBN 0-8247-0562-9).

The screening methods described here may employ in vivo assays, although they may be configured for in vitro use. In vivo assays generally involve exposing a cell comprising Cnx or ERp57 to the candidate molecule. In in vitro assays, Cnx or ERp57 is exposed to the candidate molecule, optionally in the presence of other components, such as crude or semi-purified cell extract, or purified proteins. Where in vitro assays are conducted, these may employ arrays of candidate molecules (for example, an arrayed library). In vivo assays may be employed. Therefore, the Cnx or ERp57 polypeptide may be comprised in a cell, such as heterologously. Such a cell may be a transgenic cell, which has been engineered to express Cnx or ERp57 as described above.

Where an extract is employed, it may comprise a cytoplasmic extract or a nuclear extract, methods of preparation of which are well known in the art.

It will be appreciated that any component of a cell comprising Cnx or ERp57 may be employed, such as an organelle. One embodiment utilises a cytoplasmic or nuclear preparation, e.g., comprising a cell nucleus which comprises Cnx or ERp57 as described. The nuclear preparation may comprise one or more nuclei, which may be permeabilised or semi-permeabilised, by detergent treatment, for example.

Thus, in a specific embodiment, an assay format may include the following: a multiwell microtitre plate is set up to include one or more cells expressing Cnx or ERp57 polypeptide in each well; individual candidate molecules, or pools of candidate molecules, derived for example from a library, may be added to individual wells and modulation of Cnx or ERp57 activity measured. Where pools are used, these may be subdivided in to further pools and tested in the same manner. Cnx or ERp57 activity, for example binding activity or transcriptional co-activation activity, as described elsewhere in this document may then be assayed.

Alternatively or in addition to the assay methods described above, "subtractive" procedures may also be used to identify modulators or antagonists of Cnx or ERp57. Under such "subtractive" procedures, a plurality of molecules is provided, which comprises one or more candidate molecules capable of functioning as a modulator (e.g., cell extract, nuclear extract, library of molecules, etc), and one or more components is removed, depleted or subtracted from the plurality of molecules. The "subtracted" extract, etc, is then assayed for activity, by exposure to a cell comprising Cnx or ERp57 (or a component thereof) as described.

Thus, for example, an 'immunodepletion' assay may be conducted to identify such modulators as follows. A cytoplasmic or nuclear extract may be prepared from a cell. The extract may be depleted or fractionated to remove putative modulators, such as by use of immunodepletion with appropriate antibodies. If the extract is depleted of a modulator, it will lose the ability to affect Cnx or ERp57 function or activity or expression. A series of subtractions and/or depletions may be required to identify the modulators or antagonists.

It will also be appreciated that the above "depletion" or "subtraction" assay may be used as a preliminary step to identify putative modulatory factors for further screening. Furthermore, or alternatively, the "depletion" or "subtraction" assay may be used to confirm the modulatory activity of a molecule identified by other means (for example, a "positive" screen as described elsewhere in this document) as a putative modulator.

Candidate molecules subjected to the assay and which are found to be of interest may be isolated and further studied. Methods of isolation of molecules of interest will depend on the type of molecule employed, whether it is in the form of a library, how many candidate molecules are being tested at any one time, whether a batch procedure is being followed, etc.

The candidate molecules may be provided in the form of a library. In one embodiment, more than one candidate molecule may be screened simultaneously. A library of candidate molecules may be generated, for example, a small molecule library, a polypeptide library, a nucleic acid library, a library of compounds (such as a combinatorial library), a library of antisense molecules such as antisense DNA or antisense RNA, an antibody library etc, by means known in the art. Such libraries are suitable for high-throughput screening. Different cells comprising Cnx or ERp57 may be exposed to individual members of the library, and effect on the Cnx or ERp57 activity determined. Array technology may be employed for this purpose. The cells may be spatially separated, for example, in wells of a microtitre plate.

In an embodiment, a small molecule library is employed. By a "small molecule", we refer to a molecule whose molecular weight may be less than about 50 kDa. In particular embodiments, a small molecule may have a molecular weight which is less than about 30 kDa, such as less than about 15 kDa or less than 10 kDa or so. Libraries of such small molecules, here referred to as "small molecule libraries" may contain polypeptides, small peptides, for example, peptides of 20 amino acids or fewer, for example, 15, 10 or 5 amino acids, simple compounds, etc.

Alternatively or in addition, a combinatorial library, as described in further detail below, may be screened for modulators or antagonists of Cnx or ERp57. Assays for Cnx or ERp57 activity are described above.

Libraries

Libraries of candidate molecules, such as libraries of polypeptides or nucleic acids, may be employed in the screens for Cnx or ERp57 antagonists and inhibitors described here. Such libraries are exposed to Cnx or ERp57 protein, and their effect, if any, on the activity of the protein determined.

Selection protocols for isolating desired members of large libraries are known in the art, as typified by phage display techniques. Such systems, in which diverse peptide sequences are displayed on the surface of filamentous bacteriophage (Scott and Smith (1990 supra), have proven useful for creating libraries of antibody fragments (and the nucleotide sequences that encoding them) for the in vitro selection and amplification of specific antibody fragments that bind a target antigen. The nucleotide sequences encoding the V H and V L regions are linked to gene fragments which encode leader signals that direct them to the periplasmic space of *E. coli* and as a result the resultant antibody fragments are displayed on the surface of the bacteriophage, typically as fusions to bacteriophage coat proteins (e.g., pIII or pVIII). Alternatively, antibody fragments are displayed externally on lambda phage capsids (phagebodies). An advantage of phage-based display systems is that, because they are biological systems, selected library members can be amplified simply by growing the phage containing the selected library member in bacterial cells. Furthermore, since the nucleotide sequence that encodes the polypeptide library member is contained on a phage or phagemid vector, sequencing, expression and subsequent genetic manipulation is relatively straightforward.

Methods for the construction of bacteriophage antibody display libraries and lambda phage expression libraries are well known in the art (McCafferty et al. (1990) supra; Kang et al. (1991) *Proc. Natl. Acad. Sci. U.S.A.*, 88: 4363;

Clackson et al. (1991) Nature, 352: 624; Lowman et al. (1991) Biochemistry, 30: 10832; Burton et al. (1991) Proc. Natl. Acad. Sci U.S.A., 88: 10134; Hoogenboom et al. (1991) Nucleic Acids Res., 19: 4133; Chang et al. (1991) J. Immunol., 147: 3610; Breitling et al. (1991) Gene, 104: 147; Marks et al. (1991) supra; Barbas et al. (1992) supra; Hawkins and Winter (1992) J. Immunol., 22: 867; Marks et al., 1992, J. Biol. Chem., 267: 16007; Lerner et al. (1992) Science, 258: 1313, incorporated herein by reference). Such techniques may be modified if necessary for the expression generally of polypeptide libraries.

One particularly advantageous approach has been the use of scFv phage-libraries (Bird, R. E., et al. (1988) Science 242: 423-6, Huston et al., 1988, Proc. Natl. Acad. Sci U.S.A., 85: 5879-5883; Chaudhary et al. (1990) Proc. Natl. Acad. Sci U.S.A., 87: 1066-1070; McCafferty et al. (1990) supra; Clackson et al. (1991) supra; Marks et al. (1991) supra; Chiswell et al. (1992) Trends Biotech., 10: 80; Marks et al. (1992) supra). Various embodiments of scFv libraries displayed on bacteriophage coat proteins have been described. Refinements of phage display approaches are also known, for example as described in WO96/06213 and WO92/01047 (Medical Research Council et al.) and WO97/08320 (Morphosys, supra), which are incorporated herein by reference.

Alternative library selection technologies include bacteriophage lambda expression systems, which may be screened directly as bacteriophage plaques or as colonies of lysogens, both as previously described (Huse et al. (1989) Science, 246: 1275; Caton and Koprowski (1990) Proc. Natl. Acad. Sci. U.S.A., 87; Mullinax et al. (1990) Proc. Natl. Acad. Sci. U.S.A., 87: 8095; Persson et al. (1991) Proc. Natl. Acad. Sci. U.S.A., 88: 2432) and are of use in the methods and compositions described here. These expression systems may be used to screen a large number of different members of a library, in the order of about $10^6$ or even more. Other screening systems rely, for example, on direct chemical synthesis of library members. One early method involves the synthesis of peptides on a set of pins or rods, such as described in WO84/03564. A similar method involving peptide synthesis on beads, which forms a peptide library in which each bead is an individual library member, is described in U.S. Pat. No. 4,631,211 and a related method is described in WO92/00091. A significant improvement of the bead-based methods involves tagging each bead with a unique identifier tag, such as an oligonucleotide, so as to facilitate identification of the amino acid sequence of each library member. These improved bead-based methods are described in WO93/06121.

Another chemical synthesis method involves the synthesis of arrays of peptides (or peptidomimetics) on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a receptor) and reactive library members occur is determined, thereby identifying the sequences of the reactive library members on the basis of spatial location. These methods are described in U.S. Pat. No. 5,143,854; WO90/15070 and WO92/10092; Fodor et al. (1991) Science, 251: 767; Dower and Fodor (1991) Ann. Rep. Med. Chem., 26: 271.

Other systems for generating libraries of polypeptides or nucleotides involve the use of cell-free enzymatic machinery for the in vitro synthesis of the library members. In one method, RNA molecules are selected by alternate rounds of selection against a target ligand and PCR amplification (Tuerk and Gold (1990) Science, 249: 505; Ellington and Szostak (1990) Nature, 346: 818). A similar technique may be used to identify DNA sequences which bind a predetermined human transcription factor (Thiesen and Bach (1990) Nucleic Acids Res., 18: 3203; Beaudry and Joyce (1992) Science, 257: 635; WO92/05258 and WO92/14843). In a similar way, in vitro translation can be used to synthesise polypeptides as a method for generating large libraries. These methods which generally comprise stabilised polysome complexes, are described further in WO88/08453, WO90/05785, WO90/07003, WO91/02076, WO91/05058, and WO92/02536. Alternative display systems which are not phage-based, such as those disclosed in WO95/22625 and WO95/11922 (Affymax) use the polysomes to display polypeptides for selection. These and all the foregoing documents also are incorporated herein by reference.

The library may in particular comprise a library of zinc fingers; zinc fingers are known in the art and act as transcription factors. Suitable zinc finger libraries are disclosed in, for example, WO 96/06166 and WO 98/53057. Construction of zinc finger libraries may utilise rules for determining interaction with specific DNA sequences, as disclosed in for example WO 98/53058 and WO 98/53060. Zinc fingers capable of interacting specifically with methylated DNA are disclosed in WO 99/47656. The above zinc finger libraries may be immobilised in the form of an array, for example as disclosed in WO 01/25417.

Combinatorial Libraries

Libraries, in particular, libraries of candidate molecules, may suitably be in the form of combinatorial libraries (also known as combinatorial chemical libraries).

A "combinatorial library", as the term is used in this document, is a collection of multiple species of chemical compounds that consist of randomly selected subunits. Combinatorial libraries may be screened for molecules which are capable of inhibiting Cnx or ERp57.

Various combinatorial libraries of chemical compounds are currently available, including libraries active against proteolytic and non-proteolytic enzymes, libraries of agonists and antagonists of G-protein coupled receptors (GPCRs), libraries active against non-GPCR targets (e.g., integrins, ion channels, domain interactions, nuclear receptors, and transcription factors) and libraries of whole-cell oncology and anti-infective targets, among others. A comprehensive review of combinatorial libraries, in particular their construction and uses is provided in Dolle and Nelson (1999), Journal of Combinatorial Chemistry, Vol 1 No 4, 235-282. Reference is also made to Combinatorial peptide library protocols (edited by Shmuel Cabilly, Totowa, N.J.: Humana Press, c1998. Methods in Molecular Biology v. 87). Specific combinatorial libraries and methods for their construction are disclosed in U.S. Pat. No. 6,168,914 (Campbell, et al), as well as in Baldwin et al. (1995), "Synthesis of a Small Molecule Library Encoded with Molecular Tags," J. Am. Chem. Soc. 117:5588-5589, and in the references mentioned in those documents.

In one embodiment, the combinatorial library which is screened is one which is designed to potentially include molecules which interact with a component of the cell to influence gene expression. For example, combinatorial libraries against chromatin structural proteins may be screened. Other libraries which are useful for this embodiment include combinatorial libraries against histone modification enzymes (e.g., histone acetylation or histone methylation enzymes), or DNA modification, for example, DNA methylation or demethylation.

Further references describing chemical combinatorial libraries, their production and use include those available from the URL http://www.netsci.org/Science/Combichem/, including The Chemical Generation of Molecular Diversity. Michael R. Pavia, Sphinx Pharmaceuticals, A Division of Eli Lilly (Published July, 1995); Combinatorial Chemistry: A Strategy for the Future—MDL Information Systems discusses the role its Project Library plays in managing diversity libraries (Published July, 1995); Solid Support Combinatorial Chemistry in Lead Discovery and SAR Optimization, Adnan M. M. Mjalli and Barry E. Toyonaga, Ontogen Corporation (Published July, 1995); Non-Peptidic Bradykinin Receptor Antagonists From a Structurally Directed Non-Peptide Library. Sarvajit Chakravarty, Babu J. Mavunkel, Robin Andy, Donald J. Kyle*, Scios Nova Inc. (Published July, 1995); Combinatorial Chemistry Library Design using Pharmacophore Diversity Keith Davies and Clive Briant, Chemical Design Ltd. (Published July, 1995); A Database System for Combinatorial Synthesis Experiments—Craig James and David Weininger, Daylight Chemical Information Systems, Inc. (Published July, 1995); An Information Management Architecture for Combinatorial Chemistry, Keith Davies and Catherine White, Chemical Design Ltd. (Published July, 1995); Novel Software Tools for Addressing Chemical Diversity, R. S. Pearlman, Laboratory for Molecular Graphics and Theoretical Modeling, College of Pharmacy, University of Texas (Published June/July, 1996); Opportunities for Computational Chemists Afforded by the New Strategies in Drug Discovery: An Opinion, Yvonne Connolly Martin, Computer Assisted Molecular Design Project, Abbott Laboratories (Published June/July, 1996); Combinatorial Chemistry and Molecular Diversity Course at the University of Louisville: A Description, Arno F. Spatola, Department of Chemistry, University of Louisville (Published June/July, 1996); Chemically Generated Screening Libraries: Present and Future. Michael R. Pavia, Sphinx Pharmaceuticals, A Division of Eli Lilly (Published June/July, 1996); Chemical Strategies For Introducing Carbohydrate Molecular Diversity Into The Drug Discovery Process. Michael J. Sofia, Transcell Technologies Inc. (Published June/July, 1996); Data Management for Combinatorial Chemistry. Maryjo Zaborowski, Chiron Corporation and Sheila H. DeWitt, Parke-Davis Pharmaceutical Research, Division of Warner-Lambert Company (Published November, 1995); and The Impact of High Throughput Organic Synthesis on R&D in Bio-Based Industries, John P. Devlin (Published March, 1996).

Techniques in combinatorial chemistry are gaining wide acceptance among modern methods for the generation of new pharmaceutical leads (Gallop, M. A. et al., 1994, J. Med. Chem. 37:1233-1251; Gordon, E. M. et al., 1994, J. Med. Chem. 37:1385-1401.). One combinatorial approach in use is based on a strategy involving the synthesis of libraries containing a different structure on each particle of the solid phase support, interaction of the library with a soluble receptor, identification of the 'bead' which interacts with the macromolecular target, and determination of the structure carried by the identified 'bead' (Lam, K. S. et al., 1991, Nature 354:82-84). An alternative to this approach is the sequential release of defined aliquots of the compounds from the solid support, with subsequent determination of activity in solution, identification of the particle from which the active compound was released, and elucidation of its structure by direct sequencing (Salmon, S. E. et al., 1993, Proc. Natl. Acad. Sci. USA 90:11708-11712), or by reading its code (Kerr, J. M. et al., 1993, J. Am. Chem. Soc. 115:2529-2531; Nikolaiev, V. et al., 1993, Pept. Res. 6:161-170; Ohlmeyer, M. H. J. et al., 1993, Proc. Natl. Acad. Sci. USA 90:10922-10926).

Soluble random combinatorial libraries may be synthesized using a simple principle for the generation of equimolar mixtures of peptides which was first described by Furka (Furka, A. et al., 1988, Xth International Symposium on Medicinal Chemistry, Budapest 1988; Furka, A. et al., 1988, 14th International Congress of Biochemistry, Prague 1988; Furka, A. et al., 1991, Int. J. Peptide Protein Res. 37:487-493). The construction of soluble libraries for iterative screening has also been described (Houghten, R. A. et al. 1991, Nature 354:84-86). K. S. Lam disclosed the novel and unexpectedly powerful technique of using insoluble random combinatorial libraries. Lam synthesized random combinatorial libraries on solid phase supports, so that each support had a test compound of uniform molecular structure, and screened the libraries without prior removal of the test compounds from the support by solid phase binding protocols (Lam, K. S. et al., 1991, Nature 354:82-84).

Thus, a library of candidate molecules may be a synthetic combinatorial library (e.g., a combinatorial chemical library), a cellular extract, a bodily fluid (e.g., urine, blood, tears, sweat, or saliva), or other mixture of synthetic or natural products (e.g., a library of small molecules or a fermentation mixture).

A library of molecules may include, for example, amino acids, oligopeptides, polypeptides, proteins, or fragments of peptides or proteins; nucleic acids (e.g., antisense; DNA; RNA; or peptide nucleic acids, PNA); aptamers; or carbohydrates or polysaccharides. Each member of the library can be singular or can be a part of a mixture (e.g., a compressed library). The library may contain purified compounds or can be "dirty" (i.e., containing a significant quantity of impurities).

Commercially available libraries (e.g., from Affymetrix, ArQule, Neose Technologies, Sarco, Ciddco, Oxford Asymmetry, Maybridge, Aldrich, Panlabs, Pharmacopoeia, Sigma, or Tripose) may also be used with the methods described here.

In addition to libraries as described above, special libraries called diversity files can be used to assess the specificity, reliability, or reproducibility of the new methods. Diversity files contain a large number of compounds (e.g., 1000 or more small molecules) representative of many classes of compounds that could potentially result in nonspecific detection in an assay. Diversity files are commercially available or can also be assembled from individual compounds commercially available from the vendors listed above.

Anti-Cnx and Anti-ERp57 Antibodies

Cnx/ERp57 inhibitors, including antagonists or modulators of Cnx or ERp57, which may be used to regulate the activity of this protein (for example, for methods of treating or preventing diseases such as cancer as described in this document) may include antibodies against the Cnx or ERp57 protein.

We therefore provide for antibodies which bind to a Cnx or ERp57 polypeptide, fragment, homologue, variant or derivative thereof. Such antibodies are useful in detecting Cnx or ERp57 expression, and in particular in diagnosing a Cnx or ERp57 associated disease such as breast or liver cancer. Other antibodies include those which have therapeutic activity, i.e., which are may be used in a therapeutic manner to treat, manage or prevent any Cnx or ERp57 associated disease, including breast and liver cancer.

Antibodies which are specific for Cnx or ERp57 may be generated against any suitable epitope, for example, an epitope derived from the Cnx or ERp57 protein.

For the purposes of this document, the term "antibody" refers to complete antibodies or antibody fragments capable of binding to a selected target. Unless specified to the contrary, the term includes but is not limited to, polyclonal, monoclonal, natural or engineered antibodies including chimeric, CDR-grafted and humanised antibodies, and artificially selected antibodies produced using phage display or alternative techniques. The term also includes single chain, Fab fragments and fragments produced by a Fab expression library. Such fragments include fragments of whole antibodies which retain their binding activity for a target substance, Fv, F(ab') and F(ab')$_2$ fragments, as well as single chain antibodies (scFv), fusion proteins and other synthetic proteins which comprise the antigen-binding site of the antibody. Small fragments, such as Fv and ScFv, possess advantageous properties for diagnostic and therapeutic applications on account of their small size and consequent superior tissue distribution.

The antibodies and fragments thereof may be humanised antibodies, for example as described in EP-A-239400. Furthermore, antibodies with fully human variable regions (or their fragments), for example, as described in U.S. Pat. Nos. 5,545,807 and 6,075,181 may also be used. Neutralizing antibodies, i.e., those which inhibit any biological activity of Cnx or ERp57, may be used for diagnostics and therapeutics.

The antibodies described here may be altered antibodies comprising an effector protein such as a label. Labels which allow the imaging of the distribution of the antibody in vivo or in vitro may be used. Such labels may be radioactive labels or radioopaque labels, such as metal particles, which are readily visualisable within an embryo or a cell mass. Moreover, they may be fluorescent labels or other labels which are visualisable on tissue samples.

Antibodies may be produced by standard techniques, such as by immunisation or by using a phage display library. Such an antibody may be capable of binding specifically to the Cnx or ERp57 protein or homologue, fragment, etc.

Polyclonal Antibodies

If polyclonal antibodies are desired, a selected mammal (e.g., mouse, rabbit, goat, horse, etc.) may be immunised with an immunogenic composition comprising a Cnx or ERp57 polypeptide or peptide. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guerin) and *Corynebacterium parvum* are potentially useful human adjuvants which may be employed if purified the substance amino acid sequence is administered to immunologically compromised individuals for the purpose of stimulating systemic defence.

Serum from the immunised animal is collected and treated according to known procedures. If serum containing polyclonal antibodies to an epitope obtainable from a Cnx or ERp57 polypeptide contains antibodies to other antigens, the polyclonal antibodies can be purified by immunoaffinity chromatography. Techniques for producing and processing polyclonal antisera are known in the art. In order that such antibodies may be made, we also provide Cnx or ERp57 amino acid sequences or fragments thereof haptenised to another amino acid sequence for use as immunogens in animals or humans.

Monoclonal Antibodies

Monoclonal antibodies directed against epitopes obtainable from a Cnx or ERp57 polypeptide or peptide can also be readily produced by one skilled in the art. The general methodology for making monoclonal antibodies by hybridomas is well known. Immortal antibody-producing cell lines can be created by cell fusion, and also by other techniques such as direct transformation of B lymphocytes with oncogenic DNA, or transfection with Epstein-Barr virus. Panels of monoclonal antibodies produced against orbit epitopes can be screened for various properties; i.e., for isotype and epitope affinity.

Monoclonal antibodies may be prepared using any technique which provides for the production of antibody molecules by continuous cell lines in culture. These include, but are not limited to, the hybridoma technique originally described by Koehler and Milstein (1975 Nature 256:495-497), the trioma technique, the human B-cell hybridoma technique (Kosbor et al (1983) Immunol Today 4:72; Cote et al (1983) Proc Natl Acad Sci 80:2026-2030) and the EBV-hybridoma technique (Cole et al., *Monoclonal Antibodies and Cancer Therapy*, pp. 77-96, Alan R. Liss, Inc., 1985).

Recombinant DNA technology may be used to improve the antibodies as described here. Thus, chimeric antibodies may be constructed in order to decrease the immunogenicity thereof in diagnostic or therapeutic applications. Such techniques comprise splicing of mouse antibody genes to human antibody genes to obtain a molecule with appropriate antigen specificity and biological activity (Morrison et al (1984) Proc Natl Acad Sci 81:6851-6855; Neuberger et al (1984) Nature 312:604-608; Takeda et al (1985) Nature 314:452-454). Moreover, immunogenicity may be minimised by humanising the antibodies by CDR grafting [see European Patent Application 0 239 400 (Winter)] and, optionally, framework modification [EP 0 239 400].

Alternatively, techniques described for the production of single chain antibodies (U.S. Pat. No. 4,946,779) can be adapted to produce the substance specific single chain antibodies.

Antibodies, both monoclonal and polyclonal, which are directed against epitopes obtainable from a Cnx or ERp57 polypeptide or peptide are particularly useful in diagnosis. Monoclonal antibodies, in particular, may be used to raise anti-idiotype antibodies. Anti-idiotype antibodies are immunoglobulins which carry an "internal image" of the substance and/or agent against which protection is desired. Techniques for raising anti-idiotype antibodies are known in the art. These anti-idiotype antibodies may also be useful in therapy.

Antibodies may also be produced by inducing in vivo production in the lymphocyte population or by screening recombinant immunoglobulin libraries or panels of highly specific binding reagents as disclosed in Orlandi et al (1989, Proc Natl Acad Sci 86: 3833-3837), and Winter G and Milstein C (1991; Nature 349:293-299).

Antibody fragments which contain specific binding sites for the polypeptide or peptide may also be generated. For example, such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse W D et al (1989) Science 256:1275-128 1).

Techniques for the production of single chain antibodies (U.S. Pat. No. 4,946,778) can also be adapted to produce single chain antibodies to Cnx or ERp57 polypeptides. Also, transgenic mice, or other organisms including other mammals, may be used to express humanized antibodies.

The above-described antibodies may be employed to isolate or to identify clones expressing the polypeptide or to purify the polypeptides by affinity chromatography.

Recombinant Techniques of Antibody Production

Recombinant DNA technology may be used to produce the antibodies according to established procedure, in bacterial or mammalian cell culture. The selected cell culture system may secrete the antibody product.

Therefore, we disclose a process for the production of an antibody comprising culturing a host, e.g. *E. coli* or a mammalian cell, which has been transformed with a hybrid vector comprising an expression cassette comprising a promoter operably linked to a first DNA sequence encoding a signal peptide linked in the proper reading frame to a second DNA sequence encoding said antibody protein, and isolating said protein.

Multiplication of hybridoma cells or mammalian host cells in vitro is carried out in suitable culture media, which are the customary standard culture media, for example Dulbecco's Modified Eagle Medium (DMEM) or RPMI 1640 medium, optionally replenished by a mammalian serum, e.g. foetal calf serum, or trace elements and growth sustaining supplements, e.g. feeder cells such as normal mouse peritoneal exudate cells, spleen cells, bone marrow macrophages, 2-aminoethanol, insulin, transferrin, low density lipoprotein, oleic acid, or the like. Multiplication of host cells which are bacterial cells or yeast cells is likewise carried out in suitable culture media known in the art, for example for bacteria in medium LB, NZCYM, NZYM, NZM, Terrific Broth, SOB, SOC, 2×YT, or M9 Minimal Medium, and for yeast in medium YPD, YEPD, Minimal Medium, or Complete Minimal Dropout Medium.

In vitro production provides relatively pure antibody preparations and allows scale-up to give large amounts of the desired antibodies. Techniques for bacterial cell, yeast or mammalian cell cultivation are known in the art and include homogeneous suspension culture, e.g. in an airlift reactor or in a continuous stirrer reactor, or immobilised or entrapped cell culture, e.g. in hollow fibres, microcapsules, on agarose microbeads or ceramic cartridges.

Large quantities of the desired antibodies can also be obtained by multiplying mammalian cells in vivo. For this purpose, hybridoma cells producing the desired antibodies are injected into histocompatible mammals to cause growth of antibody-producing tumours. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane, and, after one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, incorporated herein by reference. Techniques for the preparation of recombinant antibody molecules are described in the above references and also in, for example, EP 0623679; EP 0368684 and EP 0436597, which are incorporated herein by reference.

The cell culture supernatants are screened for the desired antibodies, preferentially by immunofluorescent staining of PGCs or other pluripotent cells, such as ES or EG cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulphate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with the antigen, or fragments thereof, or with Protein-A.

Hybridoma cells secreting the monoclonal antibodies are also provided. Hybridoma cells may be genetically stable, secrete monoclonal antibodies of the desired specificity and can be activated from deep-frozen cultures by thawing and recloning.

Also included is a process for the preparation of a hybridoma cell line secreting monoclonal antibodies directed to the Cnx or ERp57 polypeptide, characterised in that a suitable mammal, for example a Balb/c mouse, is immunised with a one or more Cnx or ERp57 polypeptides, or antigenic fragments thereof; antibody-producing cells of the immunised mammal are fused with cells of a suitable myeloma cell line, the hybrid cells obtained in the fusion are cloned, and cell clones secreting the desired antibodies are selected. For example spleen cells of Balb/c mice immunised with Cnx or ERp57 are fused with cells of the myeloma cell line PAI or the myeloma cell line Sp2/0-Ag14, the obtained hybrid cells are screened for secretion of the desired antibodies, and positive hybridoma cells are cloned.

We describe a process for the preparation of a hybridoma cell line, characterised in that Balb/c mice are immunised by injecting subcutaneously and/or intraperitoneally between 10 and $10^7$ and $10^8$ cells expressing Cnx or ERp57 and a suitable adjuvant several times, e.g. four to six times, over several months, e.g. between two and four months, and spleen cells from the immunised mice are taken two to four days after the last injection and fused with cells of the myeloma cell line PAI in the presence of a fusion promoter, such as polyethylene glycol. The myeloma cells may be fused with a three- to twentyfold excess of spleen cells from the immunised mice in a solution containing about 30% to about 50% polyethylene glycol of a molecular weight around 4000. After the fusion the cells are expanded in suitable culture media as described hereinbefore, supplemented with a selection medium, for example HAT medium, at regular intervals in order to prevent normal myeloma cells from overgrowing the desired hybridoma cells.

Recombinant DNAs comprising an insert coding for a heavy chain variable domain and/or for a light chain variable domain of antibodies directed to Cnx or ERp57 as described hereinbefore are also disclosed. By definition such DNAs comprise coding single stranded DNAs, double stranded DNAs consisting of said coding DNAs and of complementary DNAs thereto, or these complementary (single stranded) DNAs themselves.

Furthermore, DNA encoding a heavy chain variable domain and/or for a light chain variable domain of antibodies directed to Cnx or ERp57 can be enzymatically or chemically synthesised DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted or exchanged with one or more other amino acids. The modification(s) may be outside the CDRs of the heavy chain variable domain and/or of the light chain variable domain of the antibody. Such a mutant DNA is also intended to be a silent mutant wherein one or more nucleotides are replaced by other nucleotides with the new codons coding for the same amino acid(s). Such a mutant sequence is also a degenerated sequence. Degenerated sequences are degenerated within the meaning of the genetic code in that an unlimited number of nucleotides are replaced by other nucleotides without resulting in a change of the amino acid sequence originally encoded. Such degenerated sequences may be useful due to their different restriction sites and/or frequency of particular codons which are preferred by the specific host, particularly *E. coli*, to obtain an optimal expression of the heavy chain murine variable domain and/or a light chain murine variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Also disclosed are recombinant DNAs comprising an insert coding for a heavy chain murine variable domain of an antibody directed to Cnx or ERp57 fused to a human constant domain g, for example γ1, γ2, γ3 or γ4, such as γ1 or γ4. Likewise recombinant DNAs comprising an insert coding for a light chain murine variable domain of an antibody directed to Cnx or ERp57 fused to a human constant domain κ or λ, such as κ are also disclosed.

In another embodiment, we disclose recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA coding for a peptide facilitating the purification of the antibody and/or a cleavage site and/or a peptide spacer and/or an effector molecule.

The DNA coding for an effector molecule is intended to be a DNA coding for the effector molecules useful in diagnostic or therapeutic applications. Thus, effector molecules which are toxins or enzymes, especially enzymes capable of catalysing the activation of prodrugs, are particularly indicated. The DNA encoding such an effector molecule has the sequence of a naturally occurring enzyme or toxin encoding DNA, or a mutant thereof, and can be prepared by methods well known in the art.

Use

Anti-Cnx and anti-ERp57 antibodies may be used in method of detecting a Cnx or ERp57 polypeptide present in biological samples by a method which comprises: (a) providing an anti-Cnx or anti-ERp57 antibody; (b) incubating a biological sample with said antibody under conditions which allow for the formation of an antibody-antigen complex; and (c) determining whether antibody-antigen complex comprising said antibody is formed.

Suitable samples include extracts tissues such as brain, breast, ovary, lung, colon, pancreas, testes, liver, muscle and bone tissues or from neoplastic growths derived from such tissues. In particular, a sample may comprise a breast or liver tissue, such as a breast or liver tissue from an individual suspected to be suffering from breast or liver cancer.

Antibodies may be bound to a solid support and/or packaged into kits in a suitable container along with suitable reagents, controls, instructions and the like.

Antibody Delivery

The antibodies against the Cnx or ERp57 protein may be delivered into a cell by means of techniques known in the art, for example by the use of liposomes, polymers, (e.g., polyethylene glycol (PEG), N-(2-hydroxypropyl) methacrylamide (HPMA) copolymers, polyamidoamine (PAMAM) dendrimers, HEMA, linear polyamidoamine polymers etc) etc. The immunoglobulins and/or antibodies may also be delivered into cells as protein fusions or conjugates with a protein capable of crossing the plasma membrane and/or the nuclear membrane. For example, the immunoglobulin and/or target may be fused or conjugated to a domain or sequence from such a protein responsible for the translocational activity. Translocation domains and sequences may include domains and sequences from the HIV-1-trans-activating protein (Tat), *Drosophila* Antennapedia homeodomain protein and the herpes simplex-1 virus VP22 protein.

Pharmaceutical Compositions and Administration

While it is possible for the Cnx/ERp57 inhibitor, including an Cnx or ERp57 nucleic acid, polypeptide, fragment, homologue, variant or derivative thereof, modulator, agonist or antagonist, a structurally related compound, or an acidic salt of either to be administered alone, the active ingredient may be formulated as a pharmaceutical formulation.

We therefore also disclose pharmaceutical compositions comprising an Cnx/ERp57 inhibitor. Such pharmaceutical compositions are useful for delivery of the Cnx/ERp57 inhibitor such as in the form of a composition as described, to an individual for the treatment or alleviation of symptoms as described.

A pharmaceutical composition in the context of the present document is a composition of matter comprising at least an Cnx/ERp57 inhibitor as an active ingredient.

The pharmaceutical formulations comprise an effective amount of the Cnx/ERp57 inhibitor together with one or more pharmaceutically-acceptable carriers. An "effective amount" is the amount sufficient to alleviate at least one symptom of a disease as described.

The effective amount will vary depending upon the particular disease or syndrome to be treated or alleviated, as well as other factors including the age and weight of the patient, how advanced the disease etc state is, the general health of the patient, the severity of the symptoms, and whether the Cnx/ERp57 inhibitor is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g. immune response) when administered to the host.

The active ingredient(s) of a pharmaceutical composition is contemplated to exhibit therapeutic activity, for example, in the alleviation of cancer, tumours, neoplasms and other related diseases. Dosage regimes may be adjusted to provide the optimum therapeutic response. For example, several divided doses may be administered daily or the dose may be proportionally reduced as indicated by the exigencies of the therapeutic situation.

The active compound may be administered in a convenient manner such as by the oral, intravenous (where water soluble), intramuscular, subcutaneous, intranasal, intradermal or suppository routes or implanting (e.g. using slow release molecules). Depending on the route of administration, the active ingredient may be required to be coated in a material to protect said ingredients from the action of enzymes, acids and other natural conditions which may inactivate said ingredient.

The Cnx/ERp57 inhibitor may be administered alone, or in combination with other therapeutic agents. Other therapeutic agents suitable for use herein are any compatible drugs that are effective for the intended purpose, or drugs that are complementary to the agent formulation. The formulation utilized in a combination therapy may be administered simultaneously, or sequentially with other treatment, such that a combined effect is achieved.

Oral Administration

In some embodiments, the inhibitor of Cnx or ERp57 activity, expression or amount is provided as an oral composition and administered accordingly. The dosage of the inhibitor of Cnx or ERp57 activity, expression or amount may be between about 1 mg/day to about 10 mg/day.

The pharmaceutical composition can be administered in an oral formulation in the form of tablets, capsules or solutions. An effective amount of the oral formulation is administered to patients 1 to 3 times daily until the symptoms of the disease alleviated.

The effective amount of agent depends on the age, weight and condition of a patient. In general, the daily oral dose of agent is less than 1200 mg, and more than 100 mg. The daily oral dose may be about 300-600 mg. Oral formulations are conveniently presented in a unit dosage form and may be prepared by any method known in the art of pharmacy. The composition may be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat the disease.

The composition may be suitably orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. The amount of active compound in such therapeutically useful compositions in such that a suitable dosage will be obtained.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen, or cherry flavouring. When the dosage unit form is a capsule, it may contain, in addition to materials of the above type, a liquid carrier.

Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavouring such as cherry or orange flavour. Of course, any material used in preparing any dosage unit form should be pharmaceutically pure and substantially non-toxic in the amounts employed. In addition, the active compound may be incorporated into sustained-release preparations and formulations.

Injectable or Intravenous Administration

In some embodiments, the Cnx/ERp57 inhibitor is provided as an injectable or intravenous composition and administered accordingly. The dosage of the Cnx/ERp57 inhibitor may be between about 5 mg/kg/2 weeks to about 10 mg/kg/2 weeks. The Cnx/ERp57 inhibitor may be provided in a dosage of between 10-300 mg/day, such as at least 30 mg/day, less than 200 mg/day or between 30 mg/day to 200 mg/day.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating such as lecithin, by the maintenance of the required particle size in the case of dispersion and by the use of superfactants.

Topical Administration

The pharmaceutical compositions disclosed here include those suitable for topical and oral administration, with topical formulations being preferred where the tissue affected is primarily the skin or epidermis (for example, psoriasis, eczema and other epidermal diseases).

The topical formulations include those pharmaceutical forms in which the composition is applied externally by direct contact with the skin surface to be treated. A conventional pharmaceutical form for topical application includes a soak, an ointment, a cream, a lotion, a paste, a gel, a stick, a spray, an aerosol, a bath oil, a solution and the like. Topical therapy is delivered by various vehicles, the choice of vehicle can be important and generally is related to whether an acute or chronic disease is to be treated. As an example, an acute skin proliferation disease generally is treated with aqueous drying preparations, whereas chronic skin proliferation disease is treated with hydrating preparations. Soaks are the easiest method of drying acute moist eruptions. Lotions (powder in water suspension) and solutions (medications dissolved in a solvent) are ideal for hairy and intertriginous areas. Ointments or water-in-oil emulsions, are the most effective hydrating agents, appropriate for dry scaly eruptions, but are greasy and depending upon the site of the lesion sometimes undesirable. As appropriate, they can be applied in combination with a bandage, particularly when it is desirable to increase penetration of the agent composition into a lesion. Creams or oil-in-water emulsions and gels are absorbable and are the most cosmetically acceptable to the patient. (Guzzo et al, in Goodman & Gilman's Pharmacological Basis of Therapeutics, 9th Ed., p. 1593-15950 (1996)). Cream formulations generally include components such as petroleum, lanolin, polyethylene glycols, mineral oil, glycerin, isopropyl palmitate, glyceryl stearate, cetearyl alcohol, tocopheryl acetate, isopropyl myristate, lanolin alcohol, simethicone, carbomen, methylchlorisothiazolinone, methylisothiazolinone, cyclomethicone and hydroxypropyl methylcellulose, as well as mixtures thereof.

Other formulations for topical application include shampoos, soaps, shake lotions, and the like, particularly those formulated to leave a residue on the underlying skin, such as the scalp (Arndt et al, in Dermatology In General Medicine 2:2838 (1993)).

In general, the concentration of the composition in the topical formulation is in an amount of about 0.5 to 50% by weight of the composition, such as about 1 to 30%, about 2-20%, or about 5-10%. The concentration used can be in the upper portion of the range initially, as treatment continues, the concentration can be lowered or the application of the formulation may be less frequent. Topical applications are often applied twice daily. However, once-daily application of a larger dose or more frequent applications of a smaller dose may be effective. The stratum corneum may act as a reservoir and allow gradual penetration of a drug into the viable skin layers over a prolonged period of time.

In a topical application, a sufficient amount of active ingredient must penetrate a patient's skin in order to obtain a desired pharmacological effect. It is generally understood that the absorption of drug into the skin is a function of the nature of the drug, the behaviour of the vehicle, and the skin. Three major variables account for differences in the rate of absorption or flux of different topical drugs or the same drug in different vehicles; the concentration of drug in the vehicle, the partition coefficient of drug between the stratum corneum and the vehicle and the diffusion coefficient of drug in the stratum corneum. To be effective for treatment, a drug must cross the stratum corneum which is responsible for the barrier function of the skin. In general, a topical formulation which exerts a high in vitro skin penetration is effective in vivo. Ostrenga et al (J. Pharm. Sci., 60:1175-1179 (1971) demonstrated that in vivo efficacy of topically applied steroids was proportional to the steroid penetration rate into dermatomed human skin in vitro.

A skin penetration enhancer which is dermatologically acceptable and compatible with the agent can be incorporated into the formulation to increase the penetration of the active compound(s) from the skin surface into epidermal keratinocytes. A skin enhancer which increases the absorption of the active compound(s) into the skin reduces the amount of agent needed for an effective treatment and provides for a longer lasting effect of the formulation. Skin penetration enhancers are well known in the art. For example, dimethyl sulfoxide (U.S. Pat. No. 3,711,602); oleic acid, 1,2-butanediol surfactant (Cooper, J. Pharm. Sci., 73:1153-1156 (1984)); a combination of ethanol and oleic acid or oleyl alcohol (EP 267,617), 2-ethyl-1,3-hexanediol (WO 87/03490); decyl methyl sulphoxide and Azone® (Hadgraft, Eur. J. Drug. Metab. Pharmacokinet, 21:165-173 (1996)); alcohols, sulphoxides, fatty acids, esters, Azone®, pyrrolidones, urea and polyoles (Kalbitz et al, Pharmazie, 51:619-637 (1996)); Terpenes such as 1,8-cineole, menthone, limonene and nerolidol (Yamane, J. Pharmacy & Pharmocology, 47:978-989 (1995)); Azone® and Transcutol (Harrison et al, Pharmaceutical Res. 13:542-546 (1996)); and oleic acid, polyethylene glycol and propylene glycol (Singh et al, Pharmazie, 51:741-744 (1996)) are known to improve skin penetration of an active ingredient.

Levels of penetration of an agent or composition can be determined by techniques known to those of skill in the art. For example, radiolabeling of the active compound, followed by measurement of the amount of radiolabeled compound absorbed by the skin enables one of skill in the art to determine levels of the composition absorbed using any of several methods of determining skin penetration of the test compound. Publications relating to skin penetration studies include Reinfenrath, W G and G S Hawkins. The Weaning Yorkshire Pig as an Animal Model for Measuring Percutaneous Penetration. In: Swine in Biomedical Research (M. E. Tumbleson, Ed.) Plenum, New York, 1986, and Hawkins, G. S. Methodology for the Execution of In Vitro Skin Penetration Determinations. In: Methods for Skin Absorption, B W Kemppainen and W G Reifenrath, Eds., CRC Press, Boca Raton, 1990, pp. 67-80; and W. G. Reifenrath, Cosmetics & Toiletries, 110:3-9 (1995).

For some applications, a long acting form of agent or composition may be administered using formulations known in the arts, such as polymers. The agent can be incorporated into a dermal patch (Junginger, H. E., in Acta Pharmaceutica Nordica 4:117 (1992); Thacharodi et al, in Biomaterials 16:145-148 (1995); Niedner R., in Hautarzt 39:761-766 (1988)) or a bandage according to methods known in the arts, to increase the efficiency of delivery of the drug to the areas to be treated.

Optionally, the topical formulations described here can have additional excipients for example; preservatives such as methylparaben, benzyl alcohol, sorbic acid or quaternary ammonium compound; stabilizers such as EDTA, antioxidants such as butylated hydroxytoluene or butylated hydroxanisole, and buffers such as citrate and phosphate.

Parenteral Administration

The active compound may also be administered parenterally or intraperitoneally. Dispersions can also be prepared in glycerol, liquid polyethylene glycols, and mixtures thereof and in oils. In some embodiments, the dispersions may be prepared in 30% Capsitol (CyDex, Inc., Lenexa, Kansas, USA). Capsitol is a polyanionic β-cyclodextrin derivative with a sodium sulfonate salt separated from the lipophilic cavity by a butyl ether spacer group, or sulfobutylether (SBE). The cyclodextrin may be SBE7-β-CD.

Adjuvants

The composition may be administered in an adjuvant, co-administered with enzyme inhibitors or in liposomes. Adjuvant is used in its broadest sense and includes any immune stimulating compound such as interferon. Adjuvants contemplated herein include resorcinols, non-ionic surfactants such as polyoxyethylene oleyl ether and n-hexadecyl polyethylene ether. Enzyme inhibitors include pancreatic trypsin. Liposomes include water-in-oil-in-water CGF emulsions as well as conventional liposomes.

Prevention of Microorganism Growth

Under ordinary conditions of storage and use, these preparations may contain a preservative to prevent the growth of microorganisms.

The prevention of the action of microorganisms can be brought about by various antibacterial and antifungal agents, for example, parabens, chlorobutanol, phenol, sorbic acid, thirmerosal, and the like. In many cases, it is possible to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compound in the required amount in the appropriate solvent with various of the other ingredients enumerated above, as required, followed by filtered sterilisation. Generally, dispersions are prepared by incorporating the sterilised active ingredient into a sterile vehicle which contains the basic dispersion medium and the required other ingredients from those enumerated above. In the case of sterile powders for the preparation of sterile injectable solutions, the methods of preparation may include vacuum drying and the freeze-drying technique which yield a powder of the active ingredient plus any additional desired ingredient from previously sterile-filtered solution thereof.

Pharmaceutically Acceptable Carrier

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

Dosage Unit Forms

It is especially advantageous to formulate pharmaceutical compositions in dosage unit form for ease of administration and uniformity of dosage.

Dosage unit form as used herein refers to physically discrete units suited as unitary dosages for the subjects to be treated; each unit containing a predetermined quantity of active material calculated to produce the desired therapeutic effect in association with the required pharmaceutical carrier. The specification for the novel dosage unit forms are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

EXAMPLES

Example 1. Materials and Methods

Antibodies and Reagents

Anti-Cnx (ab10286, ab22595), anti-ERp57 (ab13506, ab13507), anti-IgG isotype control (ab37415), anti-MMP14 (ab51074), anti-MMP9 (ab38898), anti-MMP2 (ab37150), anti-mCherry (ab125096) and anti-beta actin (ab8226) antibodies were purchased from Abcam. Anti-cortactin (p80/85) and anti-MMP14 (MAB3328, clone LEM-2/15.8) were purchased from Millipore. Anti-NEM OX133 antibody was purchased from Absolute Antibody. Anti-collagen I (cleavage site) was purchased from Immunoglobe. Agarose bound *Vicia Villosa* Lectin (VVL, #AL-1233)) was purchased from Vector Laboratories. Anti-rabbit IgG-HRP antibody and anti-mouse IgG-HRP antibody were purchased from GE Healthcare Life Sciences. Streptavidin-HRP antibody was purchased from Jackson ImmunoResearch. Alexa fluor 488, 594 or 647 secondary antibodies for immunofluorescence were purchased from Life Technologies. Hoechst 33342 is used to stain nucleus and comes from Invitrogen. Alexa fluor 635 phalloidin was purchased from Molecular Probes. N-ethylmaleimide (NEM) was purchased from ThermoFisher Scientific. Tris(2-carboxyethyl)phosphine hydrochloride (TCEP #64, 654-7) was purchased from Sigma Aldrich. GM6001 was purchased from Tocris.

Cell Culture

MDA-MB-231 and NIH3T3 cells were maintained in DMEM (HyClone high glucose, GE Healthcare Life Sciences) supplemented with 10% foetal bovine serum (FBS, Sigma Aldrich), at 37° C. in a 10% $CO_2$ incubator.

Human Samples

Human liver samples were obtained from HCC patients from National Cancer Center in Singapore as previously described (Nguyen et al., 2017).

Immunofluorescence and Imaging

Cells were seeded on coverslips, at 70 000 cells per well in a 24-well plate (ThermoFisher Scientific) and incubated overnight. Cells were fixed with 4% paraformaldehyde (PFA) in Phosphate Buffered Saline (PBS, Gibco) for 10 min, rinsed 3 times with PBS and then permeabilized with 0.2% Triton X-100 for 10 min. Cells were incubated with primary antibodies (1/100 diluted in 2% FBS-PBS) for 1 h 30 at room temperature, rinsed 3 times with PBS and incubated with secondary antibodies (1/200 diluted in 2% FBS-PBS) for 40 min before being rinsed and mounted on microscope slides.

Live cell immunofluorescence were realized by incubating live cells with anti-calnexin (ab22595) antibody (1/100 diluted in culture media) for 15 min. Then cells were washed 3 times with PSB 1× and fixed with 4% PFA. Then, an immunofluorescence with secondary antibodies was performed. Images were made using LSM-700 (Zeiss) confocal microscope.

ECM Degradation Assay

Gelatin (#G1393, Sigma) was first coupled to 5-carboxy-X-rhodamine succinimidyl ester (#C-6125, ThermoFisher Scientific). Sterile coverslips were coated with gelatin for 20 min, then fixed with 0.5% glutaraldehyde (#15960, Electron Microscopy Sciences) for 40 min. After washing, a layer of 0.5 mg/ml type I collagen (#354236 rat tail, Corning) was coated onto these gelatin coverslips and incubated 4 h at 37° C. before cell seeding. Cells were incubated overnight before fixation and staining. At least 20 images were acquired for each condition, experiments were done in 3 biological replicates. The area of degradation was quantified using ImageJ and normalized to the number of nuclei in each image.

Chemical Collagen Disulfide Bond Reduction

To chemically reduce collagen disulfide bonds before cell seeding and ECM degradation assay, a 0.5 mg/ml type I collagen matrix was coated onto red gelatin coverslips and incubated 4 h at 37° C. for polymerization. Collagen was incubated with 2.5 mM TCEP (#64, 654-7, Sigma Aldrich) for 30 min at room temperature, rinsed 3 times with 1% BSA in PBS, and incubated with 5 mM N-ethylmaleimide (NEM

23030, ThermoFisher Scientific) for 30 min at room temperature. Coverslips were gently rinsed 3 more times with 1% BSA in PBS before cell seeding and ECM degradation assay.

GSH and GPX Experiments

To study the involvement of GSH in collagen disulfide bond reduction, cells were seeded on red gelatin and collagen I coated coverslips to proceed to ECM degradation assay. Cells were incubated 2 h to adhere and where then incubated with 1 mM L-gluthatione reduced (GSH #4251, Sigma Aldrich) overnight before fixation. For the opposite experiment, cells were seeded into red gelatin and collagen I coated coverslips, incubated 2 h to adhere and treated with 10 mg GPx1 (SRP-8010, Sigma Aldrich) and $H_2O_2$ every 30 min for 6 hours before fixation. ECM degradation quantification was performed as described above.

Western Blotting

Cells were washed twice with ice-cold PBS, scraped in ice-cold RIPA lysis buffer (50 mM Tris, 200 mM NaCl, 0.5% NP-40, Complete and PhoStop inhibitor [Roche Applied Science]) and lysed for 30 min at 4° C. Lysates were then clarified by centrifugation at 13000 g for 10 min at 4° C. Lysate concentrations were determined using Bradford reagent (Bio-Rad). Lysates were boiled at 95° C. for 5 min and separated by SDS-PAGE electrophoresis using 4-12% Bis-Tris NuPage gels (Invitrogen) at 180V for 70 min. Samples were then transferred on nitrocellulose membranes using iBlot transfer system (Invitrogen) and blocked using 3% BSA dissolved in TBST (50 mM Tris, 150 mM NaCl and 0.1% Tween-20) for 1 h at room temperature. Membranes were then incubated with primary antibodies (1/1000 diluted in 3% BSA-TBST) overnight at 4° C. The next day, membranes were washed 3 times with TBST and incubated with secondary antibody conjugated with horseradish peroxidase (HRP) or streptavidin-HRP for 1 h 30 at room temperature. Membranes were washed 3 more times with TBST before ECL exposure.

Cnx Immunoprecipitation

Protein G Dynabeads (Life Technologies) were washed twice with PBS and once with RIPA lysis buffer before being incubated 1 h at 4° C. with 2 μg of anti-Cnx antibody (ab22595, Abcam). The beads were then incubated with clarified cell lysates for 1 h at 4° C. with constant agitation, before being washed 5 times with RIPA lysis buffer. Precipitated proteins were eluted in 2×LDS sample buffer containing 50 mM DTT and boiled at 95° C. for 10 min before being analyzed SDS-PAGE electrophoresis and western blot.

VVL Immunoprecipitation on Hepatic Lysates

Harvested liver tissues were homogenized in ice-cold RIPA lysis buffer and lysed for 1 h at 4° C. with constant agitation. Samples were then clarified by centrifugation at 13000 g for 15 min at 4° C. Clarified tissue lysates were incubated with agarose-bound VVL beads (Vector Laboratories) overnight at 4° C. Beads were washed 3 times with RIPA lysis buffer, and the precipitated proteins were eluted in 2×LDS sample buffer containing 50 mM DTT. Samples were boiled at 95° C. for 10 min before being separated by SDS-PAGE electrophoresis and analyzed by western blotting.

MMP Activity

In order to quantify total MMP activity, we used a FRET-based MMP activity assay kit (ab112147), on cell lysates, according to the manufacturer's protocol. Fluorescence was read at 540 nm using a microplate reader (Tecan) every 5 min for 2 h.

CRISPR/Cas9 Knock-out (KO) Cell Line Creation

MDA ER-G2 Cnx KO cell line was made using Cnx CRISPR/Cas9 KO Plasmid (sc-400154) and Cnx HDR Plasmid (sc-400154-HDR), from Santa Cruz Biotechnology. Cells were transfected twice with these 2 plasmids using Lipofectamine 3000 reagent (ThermoFisher Scientific) in order to achieve a complete KO in some cells. Transfected cells were then selected by clonal selection, and clones were tested for Cnx expression before expansion.

siRNA Transfection siRNA oligonucleotides were purchased from Dharmacon. Endogenous Cnx was depleted by 2 rounds of siRNA transfection. Briefly, cells were first treated by reverse transfection with 25 nM of control siRNA (5'-UGGUUUA-CAUGUCGACUAA-3') or siRNA against Cnx (5'-CAAGAGUGGUCCUAGGAGAUU-3') using Lipofectamine RNAiMAX (ThermoFisher Scientific). The day after, cells were treated again by forward transfection with nM siRNA diluted in Opti-MEM medium (Gibco) and incubated 5 more days before analyzing.

Cloning

To construct the Cnx plasmids, pDONR221-calexin wild-type (cnx WT) or pDONR221-Cnx mutant were gene synthesized (GenScript) and cloned into pCDNA-DEST40-CmCherry destination vector using Gateway LR cloning reaction.

DNA Transfection

MDA ERG2 Cnx KO cells were seeded at 500 000 cells per well in a 6-well plate (ThermoFisher Scientific) and incubated overnight before transfection. pCDNA-Cnx-CmCherry (WT or mutant) plasmids were transfected into cells using Lipofectamine 3000 reagent (ThermoFisher Scientific), according to the manufacturer's protocol. After transfection, cells were incubated for 2 days before use for further experiment, or 3 days before protein extraction and SDS-PAGE analysis.

Proximity Ligation Assay (PLA)

MDA WT and MDA ER-G2 cells were seeded on glass coverslips and incubated overnight before using. Cells were then incubated for 15 min at 37° C. with Cnx (ab10286) and ERp57 (ab13506) primary antibodies before being washed and fixed with 4% paraformaldehyde for 10 minutes. Then, PLA experiment was performed using Duolink in situ red starter kit mouse/rabbit (Sigma Aldrich), according to manufacturer's protocol.

Sleeping Beauty Vector Construction

The plasmid expressing both oncogenic NRas-G12V and shRNA targeting p53 tumour suppressor gene was made by replacing EGFP sequences of the pT2/shp53/PGK-EGFP (Nguyen et al., 2017) with the mCherry-fused human NRas-G12V through NotI sites. The resultant vectors, named pT2/shp53/PGK-mCherry-Nras together with the pPGK-SB13 expressing Sleeping Beauty transposase were used to induce liver tumor in this study.

Mouse Models for Antibody Treatment

All animal experiments were performed in compliance with the Institutional Animal Care and Use Committee guidelines approved by Biological Resource Centre (BRC, Biomedical Sciences Institute, A*STAR).

Liver Cancer and Lung Metastases Model

Hydrodynamic tail-vein injection was performed in 5-6-week-old C57BL/6J male mice obtained from InVivos (Singapore). This technology was previously described (Carlson et al., 2005 and Nguyen et al., 2017). Each animal will be only injected one. Plasmids were prepared using EndoFree Maxi Kit (Qiagen). Transposon/transposase mixture to be used is diluted in lactated Ringer's (BRAun) in a volume corresponding to 10% of the body weight of the mice being injected. Each animal received approximately 10 µg of transposase-encoding plasmid (pPGK-SB13) and 30 µg of pT2/shp53/PGK/mCherry-Nras plasmid. Animals being injected are not anesthetized but immobilized with a plastic restrainer. Sterile single-use 27-gauge needles will be used. Injection will be completed via the lateral tail vein in less than 8 sec. Mice at 3 day-post injection (dpi) or 30 dpi of Nras/shp53-induced liver tumors were used for treatment. Intraperitoneal injection (i.p.) of anti-Calnexin antibody (Abcam, ab22595, 200 ug/mouse) or anti-Rabbit IgG (Abcam, ab37415, 200 ug/mouse) as Control. Repeat of antibodies i.p. every 2-3 days. Mice were monitored twice weekly for general health and tumor burden. At desired time points, mice were euthanized. Livers and lungs were collected for analysis of treatment efficacy.

Breast Cancer Cells Metastasis Model

MDA-231 WT and MDA-231 ER-G2 cells ($1-1.5\times10^6$) were injected in the tail vein of 6-week-old nude BALB/c mice. At 5 dpi, mice following i.p. injection of anti-Calnexin antibody (Abcam, ab22595, 200 ug/mouse) or anti-Rabbit IgG (Abcam, ab37415, 200 ug/mouse) as Control. Repetition of antibodies i.p. every 7 days. Mice were closely monitored and necropsied at desired time points. Tissues were snap-frozen or fixed in 10% Formalin solution (Sigma Aldrich) and embedded in paraffin. Sections (5-µm-thick) were stained with a standard protocol for H&E staining. Slides were scanned at 20× using a Leica SCN400 slide scanner (Leica Microsystems). Images were analyzed using Measure Stained Area algorithms of Slidepath TissueIA software. Data were collated using Microsoft Excel. Scanning and image analysis was performed by the Advanced Molecular Pathology Laboratory, Institute of Molecular and Cell Biology, Singapore.

Immunohistochemistry (IHC)

Samples were de-paraffinized in Bond Dewax Solution and rehydrated through 100% ethanol to 13 Bond Wash Solution (Leica Biosystems). Samples were boiled for 40 min at 100° C. for antigen retrieval using Bond Epitope Retrieval Solution, then treated with 3% hydrogen peroxide for 15 min and incubated with 10% goat serum block for 30 min. Subsequent staining with VVL-Biotin (Vector Biolabs, B-1235, 1:1000), mCherry (Abcam, ab125096, 1:500) was performed at room temperature for 60 min. After rinsing three times in Bond Wash Solution, samples were incubated with secondary Streptavidin-HRP antibody (Jackson ImmunoResearch Inc, 016-030-084, 1:200), anti-Rabbit-HRP antibody (GE Healthcare, NA934, 1:200) or anti-Mouse-HRP antibody (GE Healthcare, NA931, 1:200) at room temperature for 30 min. Signals indicating horseradish peroxidase (HRP-DAB) activity were visualised using Bond Refine Detection Kit (Leica) following the manufacturer's instructions. The nuclei were counterstained with hematoxylin for 5 min, dehydrated, and mounted for microscopic examination.

Immunofluorescence (IF) Microscopy

The slides required deparaffinization, antigen retrieval at pH6, and blocking steps before incubation with antibodies. Staining for mCherry (Abcam, ab125096, 1:400) and Chicken anti-Rabbit IgG performed overnight and counterstained with anti-mouse Alexa Fluor 594 (Invitrogen, A-21201, 1:400), and anti-rabbit Alexa Fluor 488 (Invitrogen, A-21441, 1:400) secondary antibodies for 30-45 min at RT. Slides were counterstained with DAPI and then mounted (Vectashield) before confocal imaging.

Statistical Analysis

Statistical significance was determined using Student's t test and calculated using GraphPad Prism software (GraphPad Software).

Example 2. Results: GALA Induces Cnx Glycosylation and Surfacing in Invadosomes

Figure 1B:
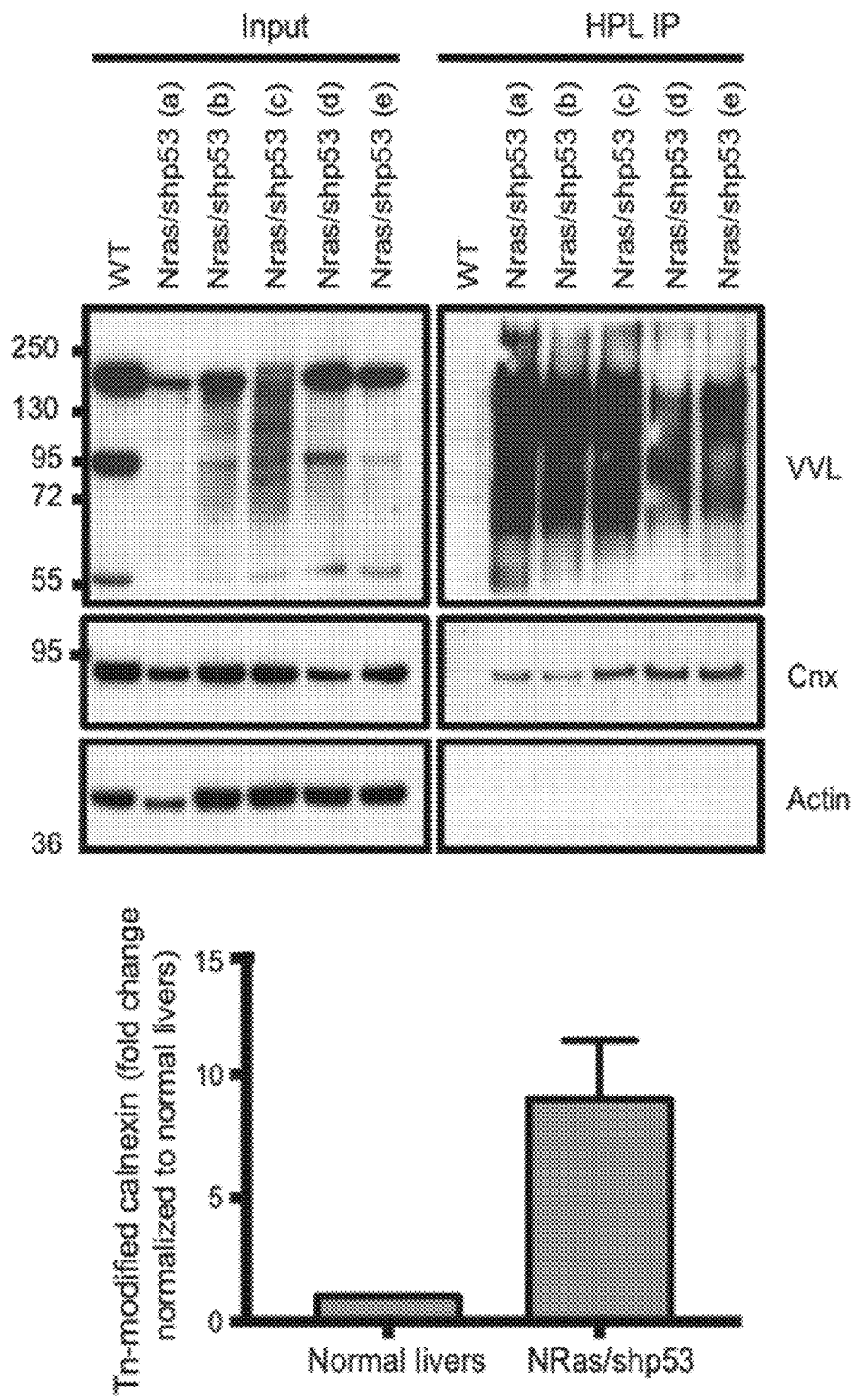
Figure 7A:
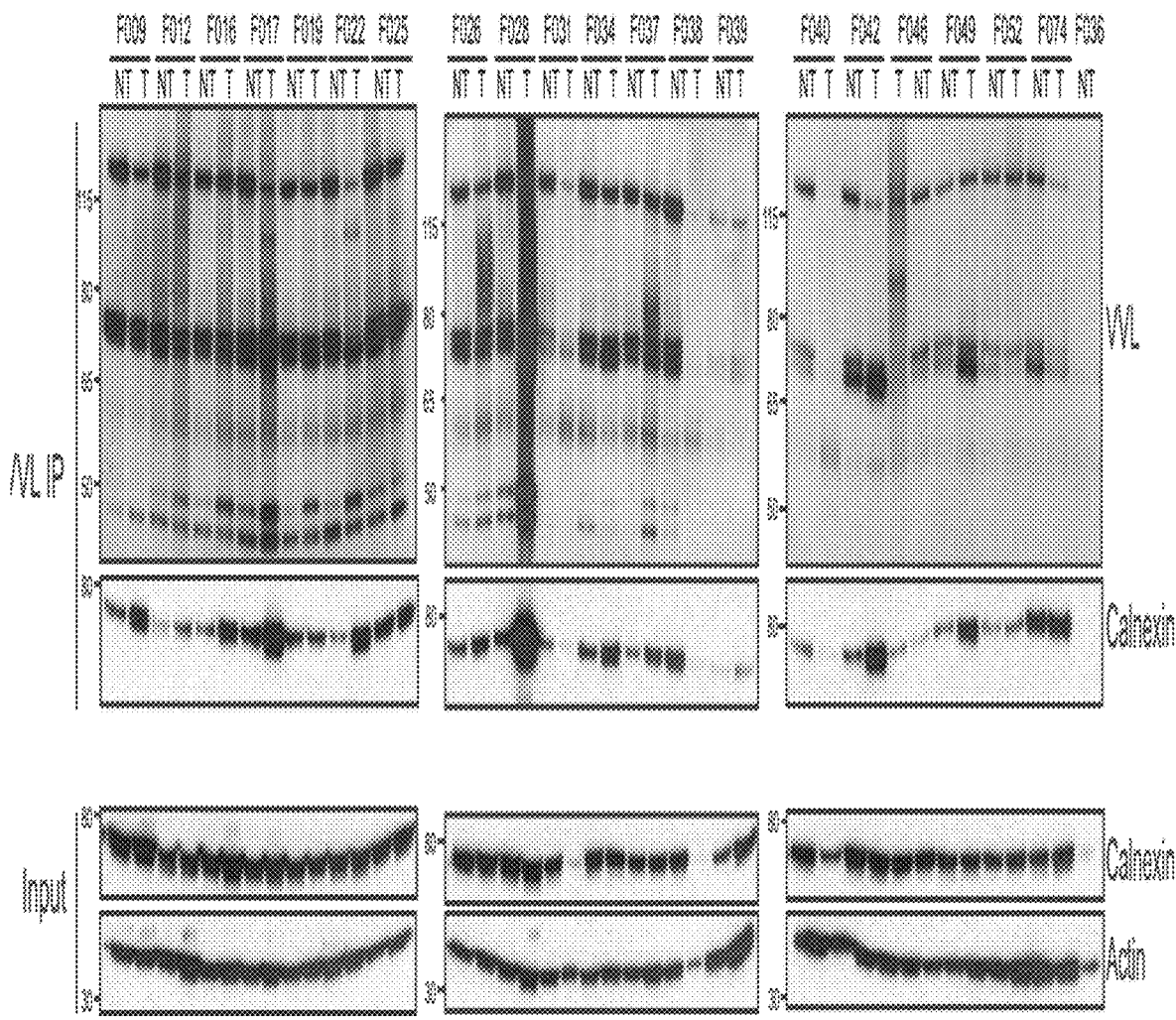
FIG. 7A is a drawing showing an immunoblot analysis of the level of Tn-modified Cnx in human liver tumors (T) versus the corresponding normal liver tissues (NT) from 20 liver cancer patients.

While we searched for glycoproteins prominent in cancers with elevated O-glycosylation, we identified Cnx as a potential carrier of Tn. On human samples with both liver tumors and matching adjacent non-tumoral tissue, we performed VVL immunoprecipitation followed by western blotting. For 15/20 of human tumor samples, Cnx had elevated levels of Tn glycosylation, to a highly variable degree (FIG. 1A and FIG. 7A). Surprisingly, in some adjacent non-tumoral tissues Cnx was also heavily glycosylated (FIG. 1A, FIG. 7A). It is not clear whether this reflects a contamination with invading tumor cells or whether there is GALA activation in the adjacent non-tumoral cells. Still, more than ~60% of human tumors exhibited high levels of Cnx glycosylation (FIG. 7A). We previously reported that GALA is activated in experimentally induced mouse liver tumors (see[3] for experimental details). Consistent with the human data, in 6-weeks old tumors, Cnx glycosylation increased by ~6 to 12 folds by comparison with healthy livers, which contain very low levels of glycosylated Cnx (FIG. 1B).

Figure 1C:
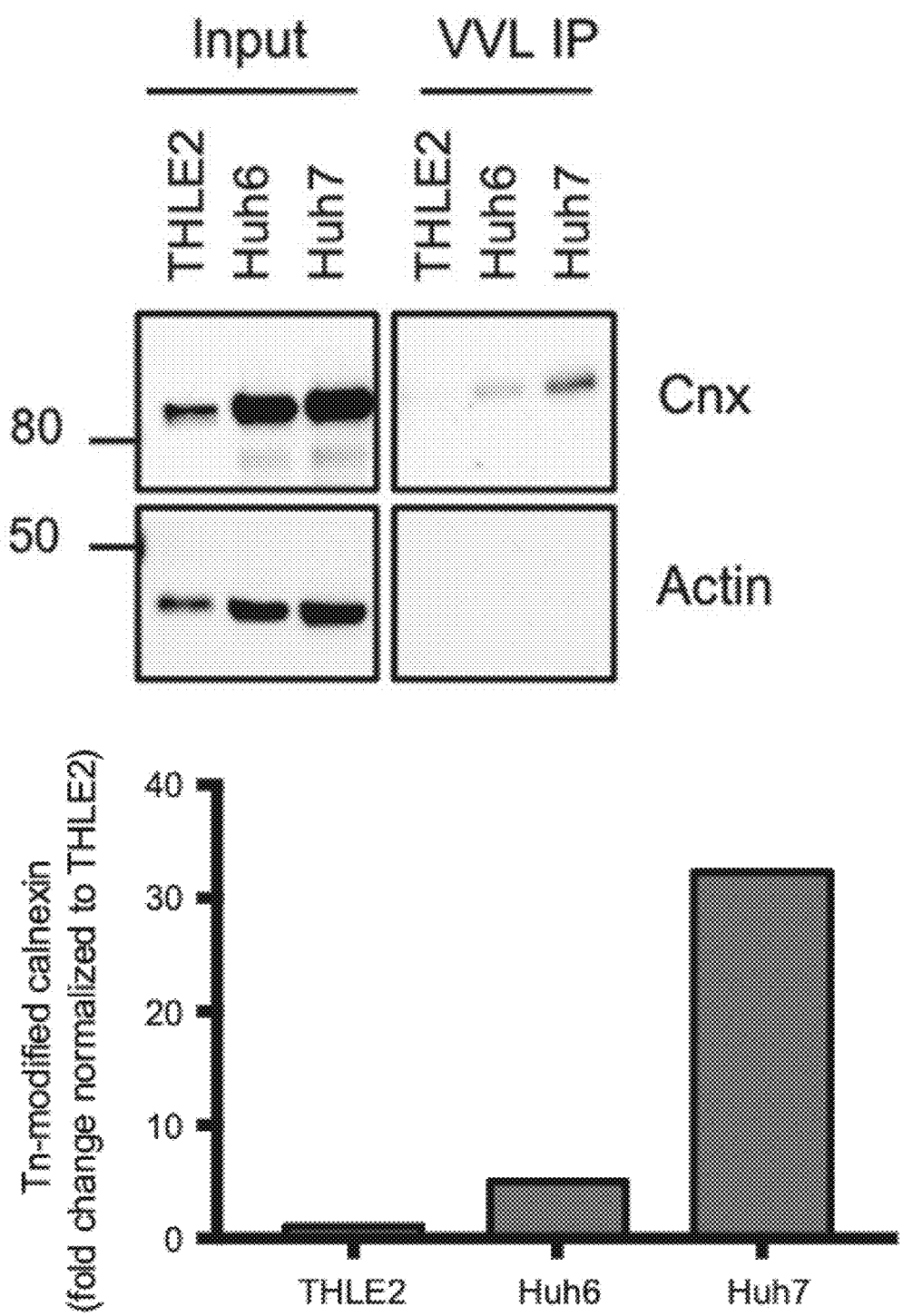
Figure 1D:
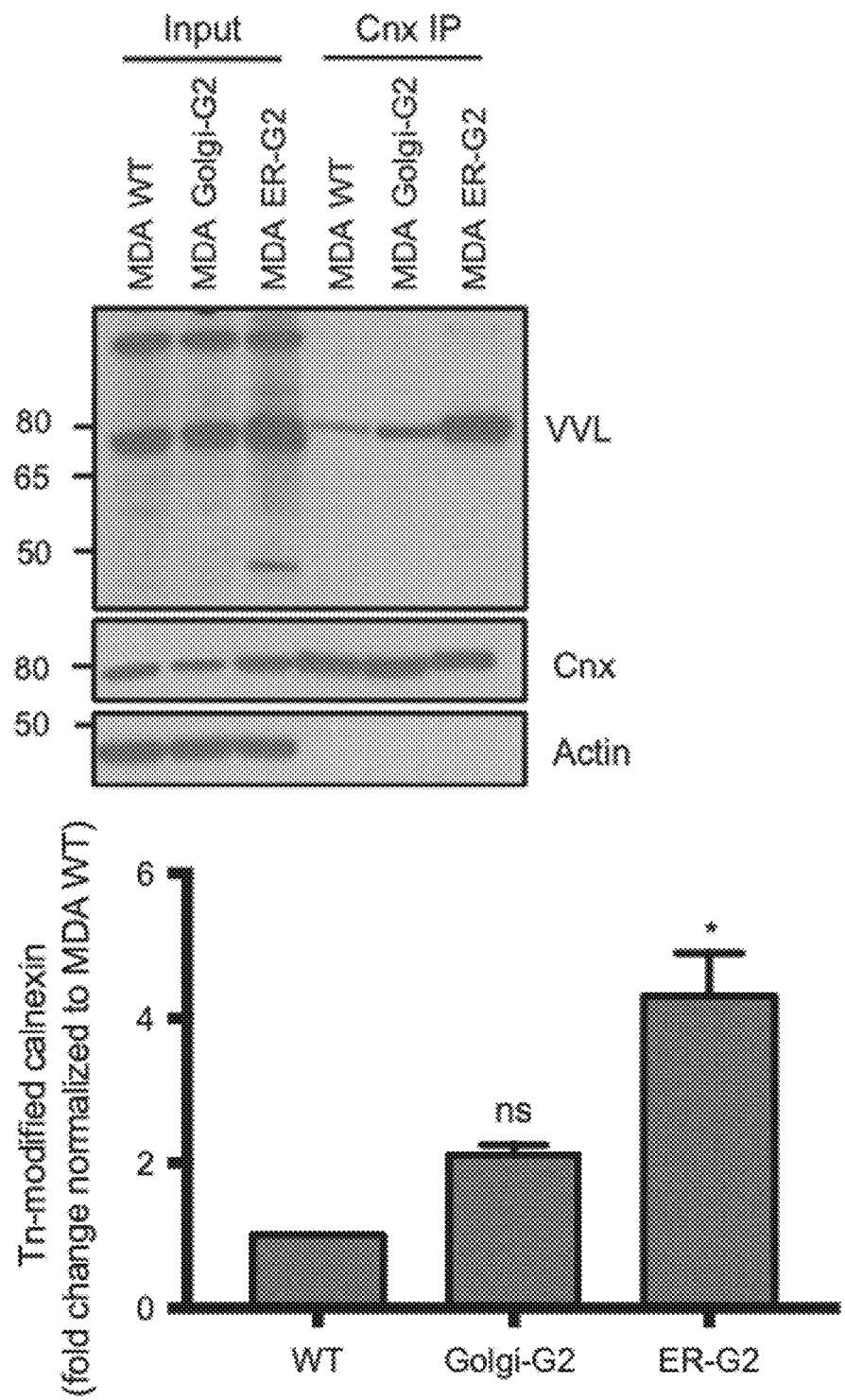
Figure 1E:
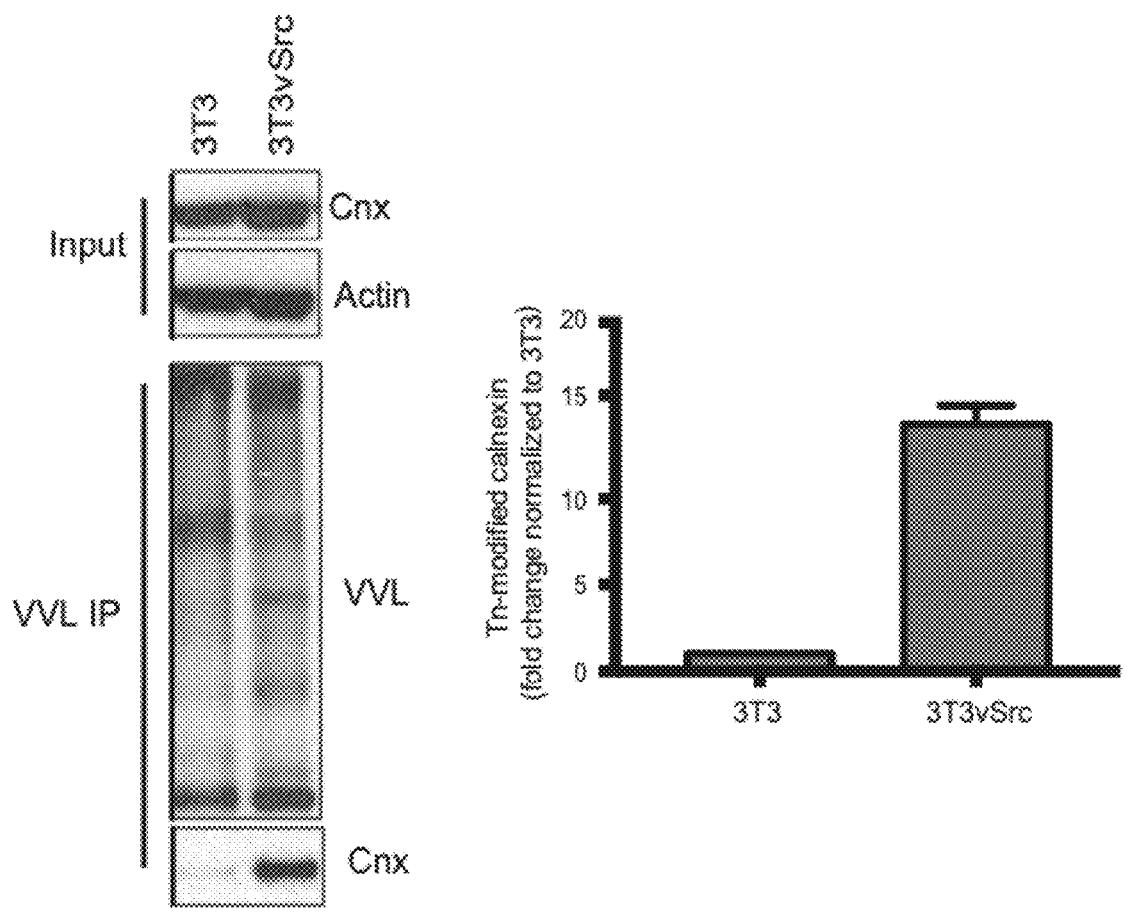

We next tested whether we would observe Cnx glycosylation in cancer cell lines. We compared human Huh6 and Huh7 liver cancer cells to immortalized liver epithelial cells THLE2[36,37]. The Huh6 and especially Huh7 cells displayed significant Cnx Tn glycosylation while their immortalized normal counterpart had very low levels (FIG. 1C). GALA is also activated in a majority of breast tumors[13]. As a model of breast cancer cell lines, we used MDA-MB-231 and found evidence of Cnx glycosylation (FIG. 1D). We previously reported that MDA-MB-231 have moderate levels of GALA compared to endogenous tumors[13]. To recapitulate in vivo levels, we generated cell lines stably expressing a GALA-mimicking chimera of GALNT2, constitutively targeted to the ER (abbreviated MDA ER-G2) and a control cell line expressing the wild-type form of GALNT2 (abbreviated MDA Golgi-G2). These three isogenic cell lines provide a system to specifically test the effect of increased ER O-glycosylation[13]. While Golgi-G2 induces only a limited increase of Cnx Tn glycosylation, ER-G2 increased it by about 4 fold as measured by VVL blot on immunoprecipitated Cnx (FIG. 1D). This comparison demonstrates that the relocation of GALNTs to the ER is sufficient to increase Cnx Tn glycosylation. Since one of the major triggers of GALA is the tyrosine kinase Src, we also compared NIH3T3 with NIH3T3vSrc (cells transformed with the viral oncogenic form of Src). Using the same approach of Cnx pull-down followed by lectin blot and measured a ~14-fold glycosylation increase induced by vSrc (FIG. 1E). Overall, our data indicate that Cnx glycosylation is occurring virtually systematically in GALA positive tumors and cells with high levels of GALNTs ER relocation or high levels of Src activity.

Figure 1F:
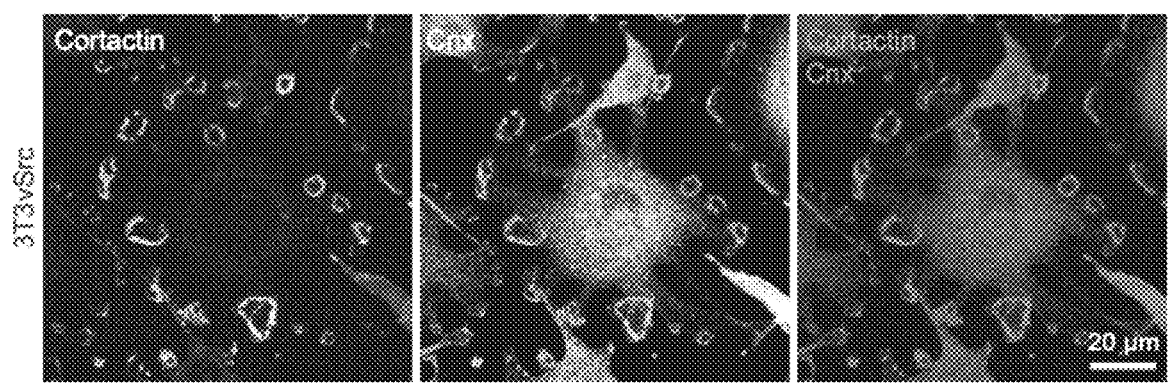
Figure 1G:
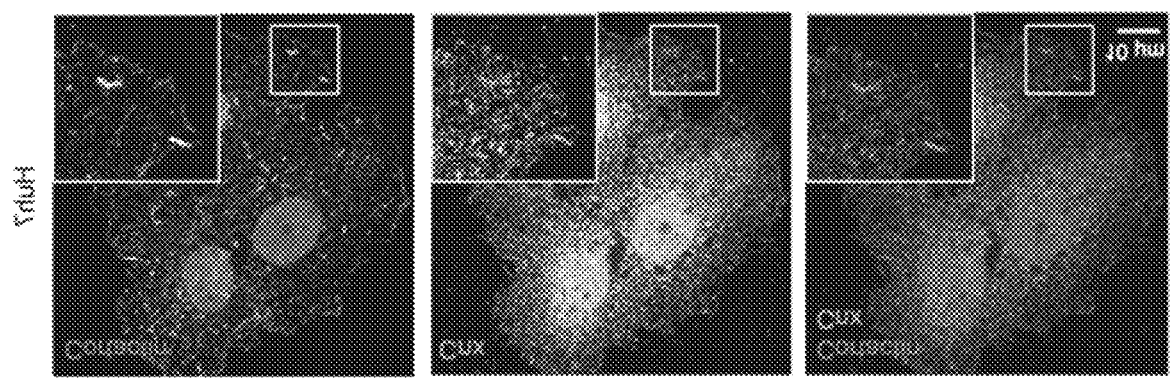
Figure 7B:
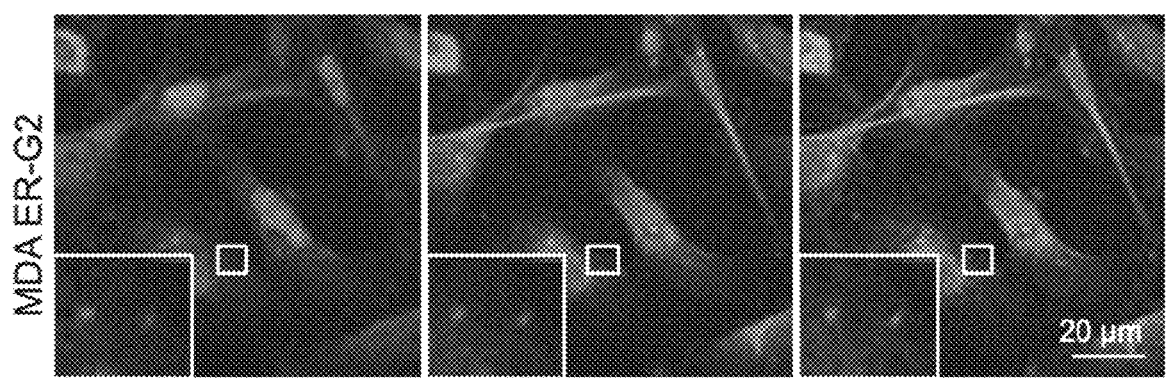
FIG. 7B is a drawing showing immunofluorescence of MDA ER-G2 cells stained with calnexin and cortactin. Scale bar, 20 µm.

While we were investigating the effects of O-glycosylation on Cnx, we observed a surprising colocalization of this protein with Cortactin, a marker of invadosomes. This was particularly clear in NIH3T3vSrc cells, which display invadosome rosettes (FIG. 1F). In the liver cancer-derived cell lines HUH7, Cnx staining was found in linear invadosomes, a structure typically associated with collagen degradation (FIG. 1G)[38]. In MDA ER-G2 cells, Cnx/Cortactin colocalization was found in punctate structures consistent with invadopodia (FIG. 7B).

Figure 1H:
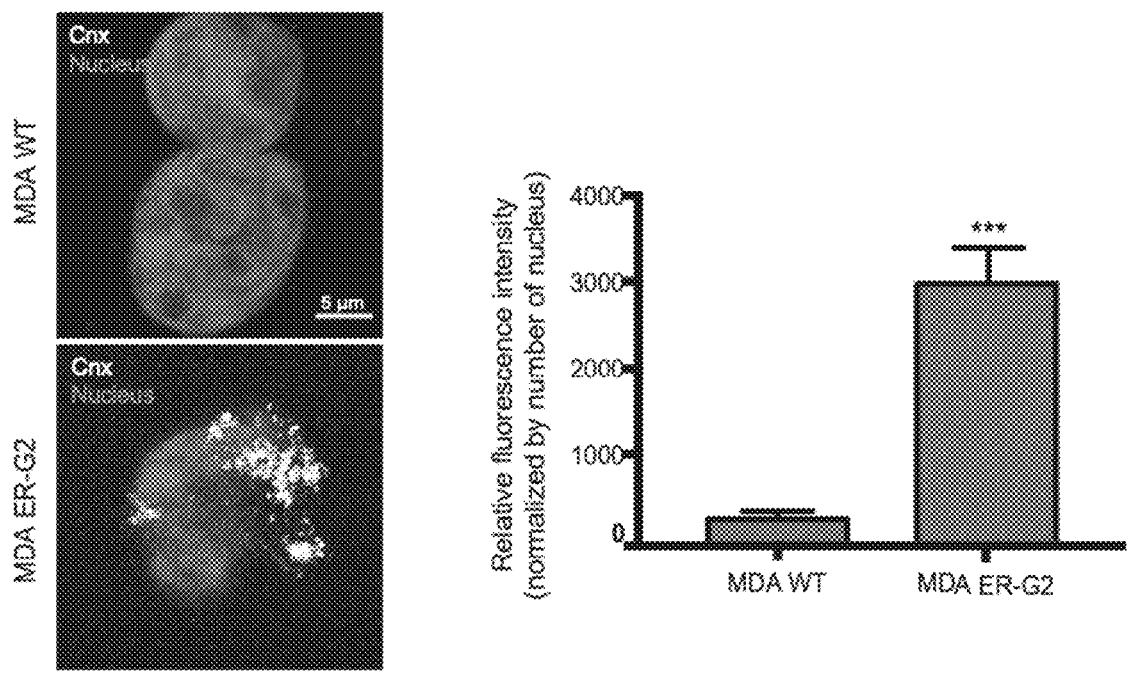
Figure 1I:
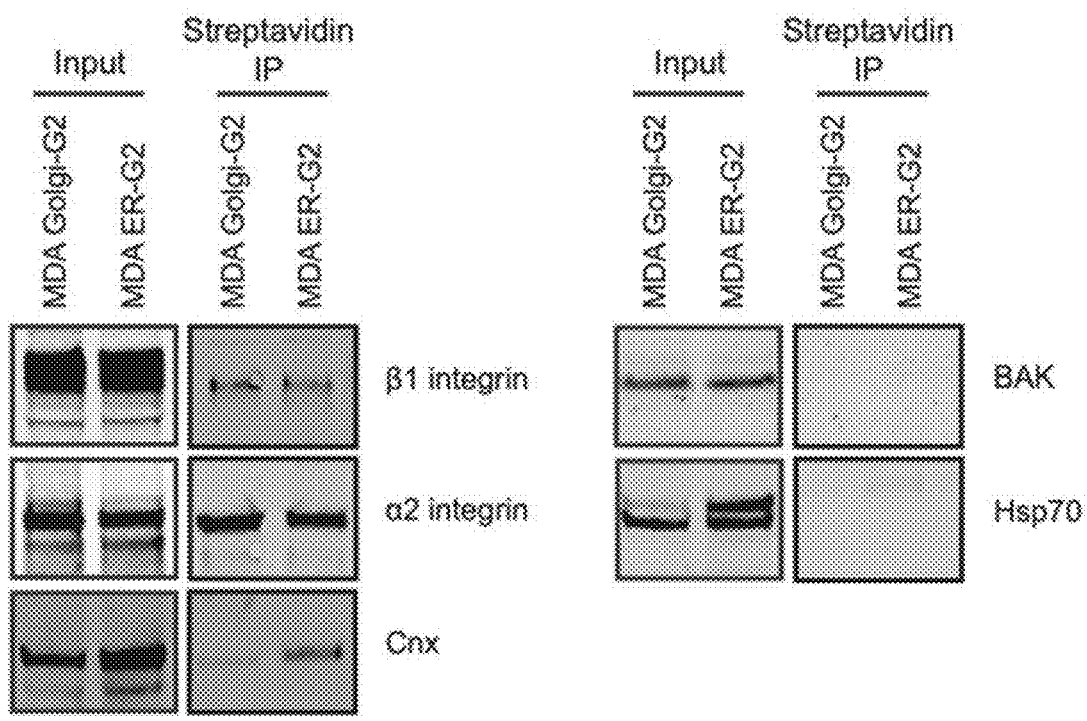

To verify that Cnx is exposed at the cell surface and not instead enriched in ER membranes associated with the invadosomes, we incubated live MDA ER-G2 cells with an anti-Cnx antibody. These ER-G2 expressing cells, but not the control, were significantly stained and had internalized the antibody, indicating Cnx is exposed to the extracellular space (FIG. 1H). Similarly, cell surface biotinylation followed by streptavidin pulldown and western blotting confirmed Cnx enrichment at the surface after GALA activation (FIG. 1I).

Figure 8A:
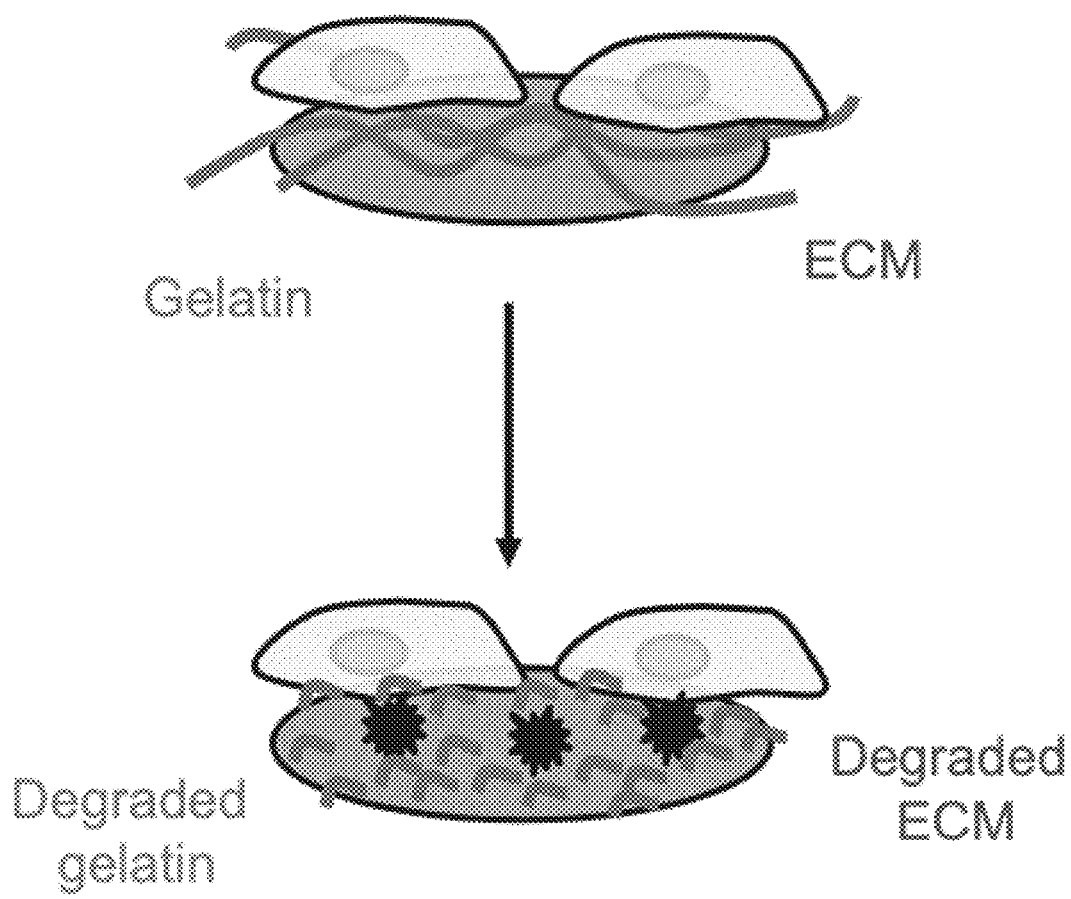
FIG. 8A is a drawing showing a schematic of matrix degradation assay.
Figure 8B:
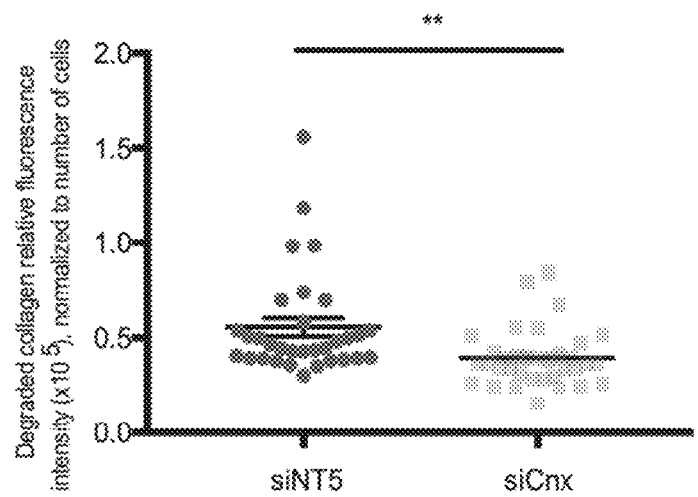
FIG. 8B is a drawing showing the relative intensity of degraded collagen antibody staining after incubation with NIH 3T3vSrc control cells and NIH 3T3vSrc Cnx KD cells. Values indicate the mean±SEM for 3 replicates. p<0.01 compared to siNT5 control conditions. Representatives images can be found on the right. Scale bar, 20 µm.
Figure 8B:
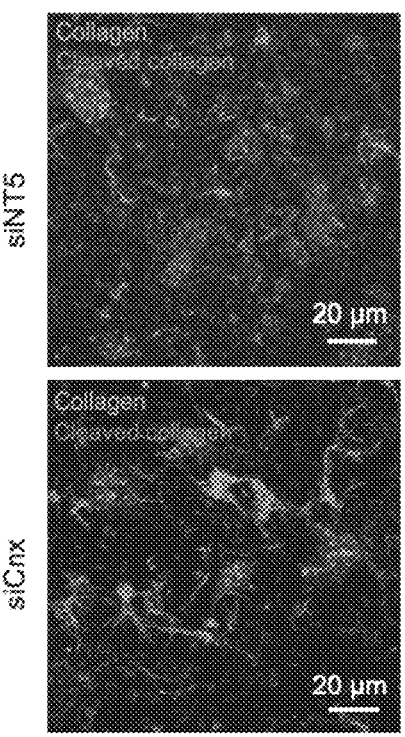

Example 3. Results: Cnx and Binding Partner ERp57 are Required for ECM Degradation Since GALA stimulates ECM degradation and Cnx is present in the responsible subcellular structures, we next asked whether surface Cnx is involved in this activity. To measure ECM degradation, we used a sandwich of fluorescently labeled gelatin overlaid with native ECM of different sources. To degrade the gelatin, cells need to first break down the overlaid ECM meshwork (FIG. 8A). We verified that cells indeed degrade collagen fibers by using an antibody specific for the cleaved form of fibrillar collagen (FIG. 8B). We quantified ECM degradative activity by measuring the loss of fluorescent gelatin using automated image analysis (FIG. 8C).

Figure 2A:
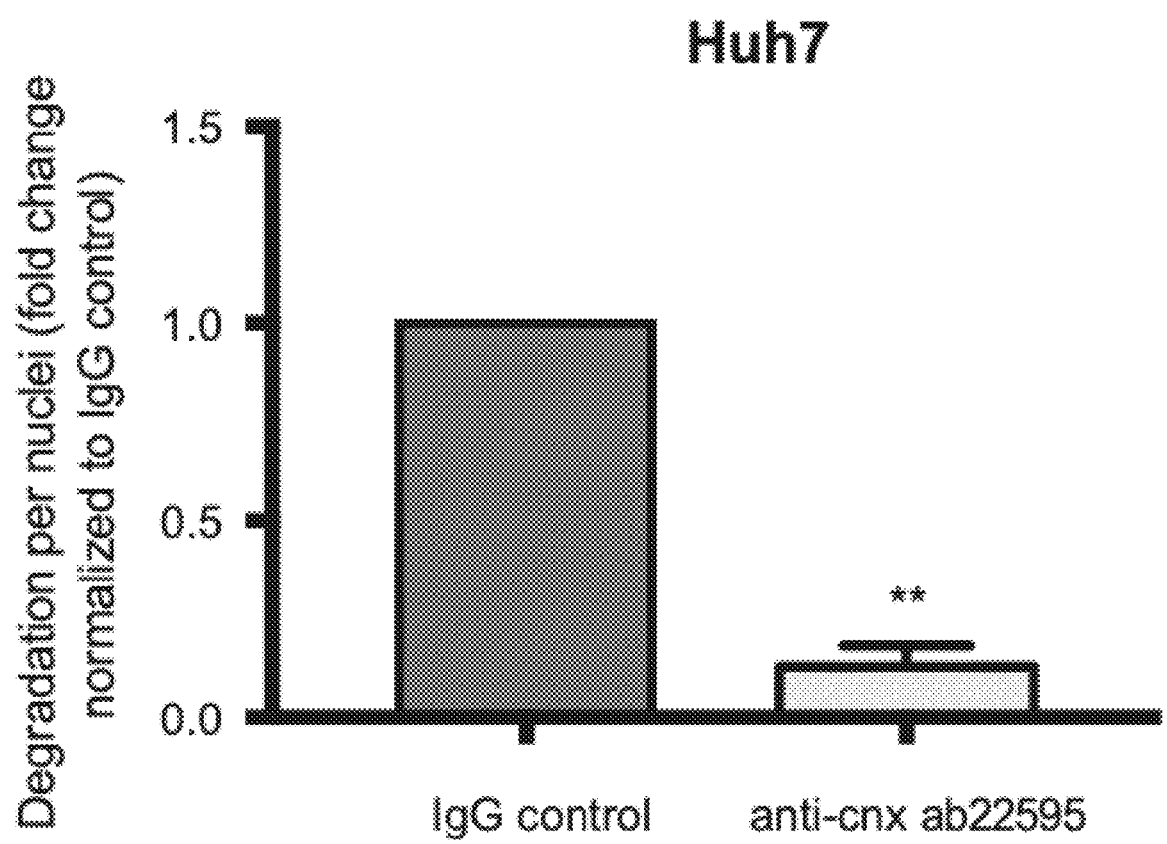
FIGS. 2A to 2I are drawings showing that Cnx and ERp57 are required for ECM degradation
Figure 2B:
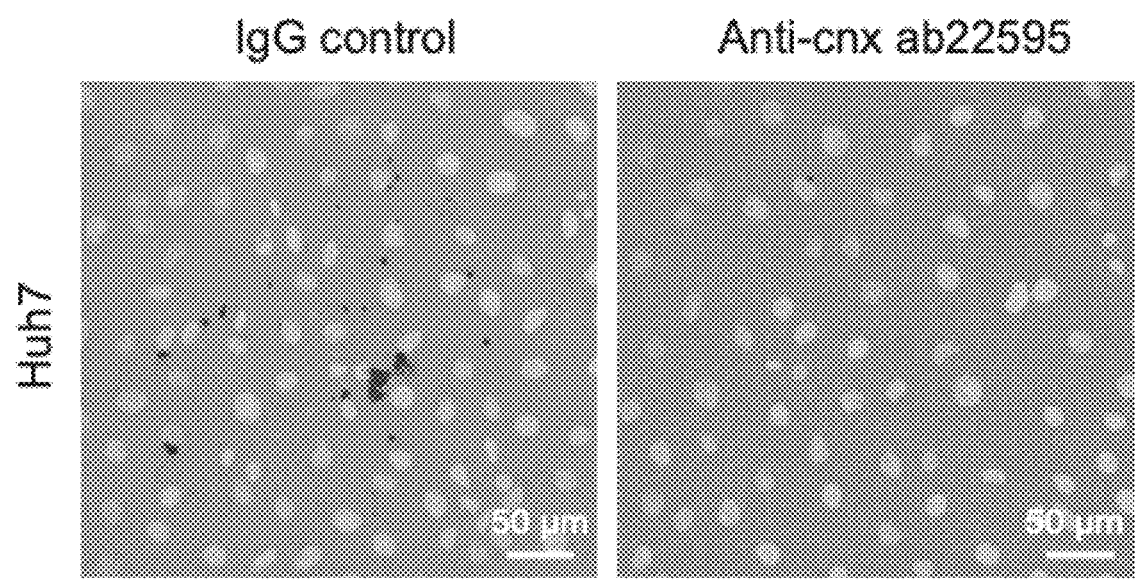
Figure 2C:
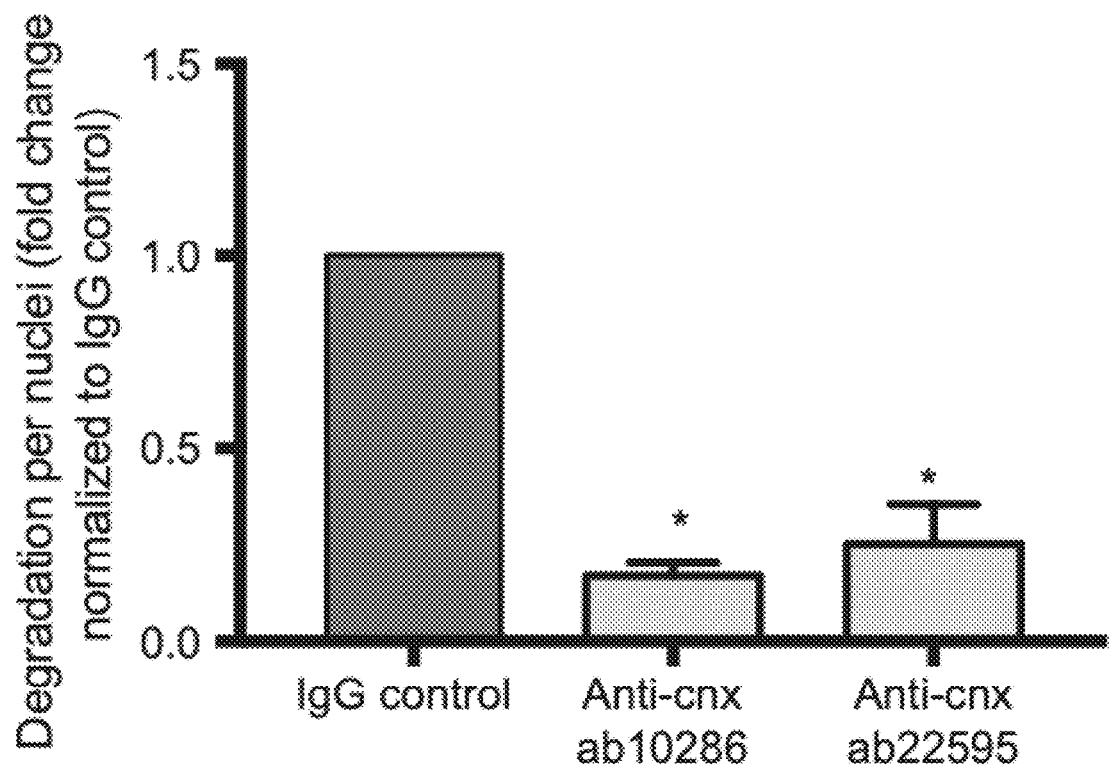
Figure 8D:
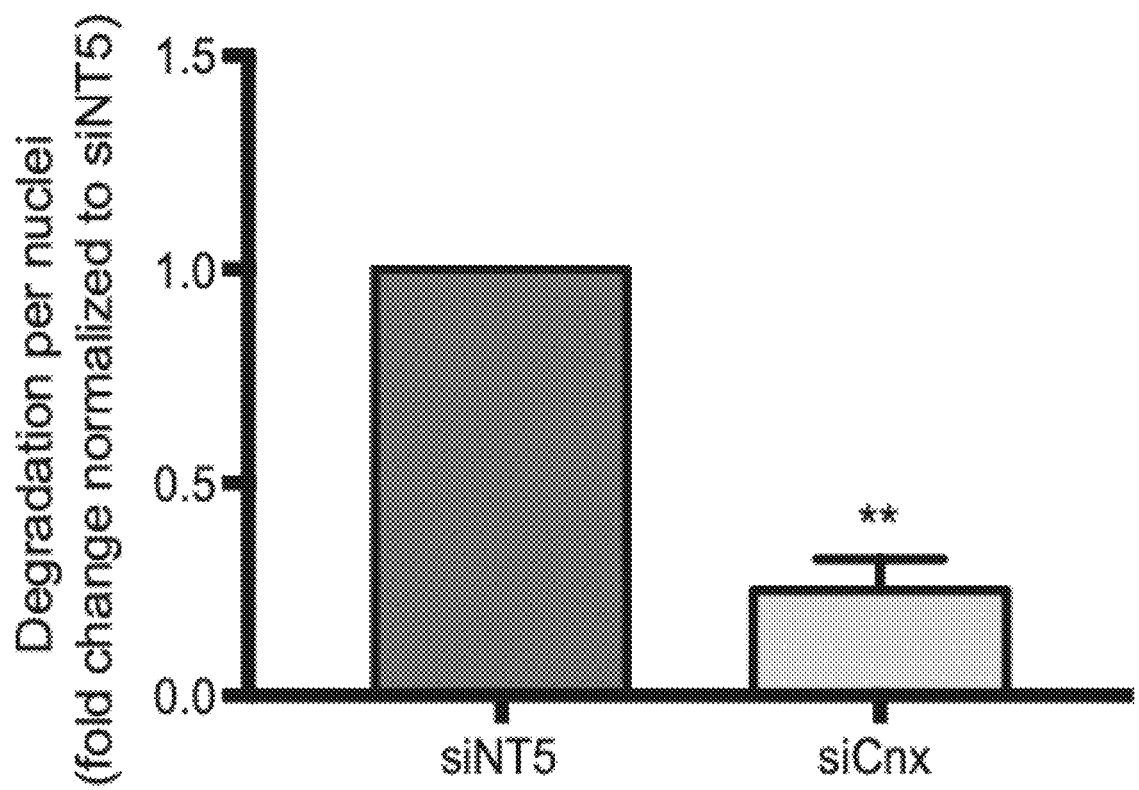
FIG. 8D is a drawing showing quantification of ECM degradation assay of NIH3T3vSrc cells transfected with control siRNA (siNT5) or siRNA against Cnx (siCnx). Values indicate the mean±SEM of normalized fold changes for 3 replicates. p<0.01 compared to siNT5 control conditions.
Figure 8E:
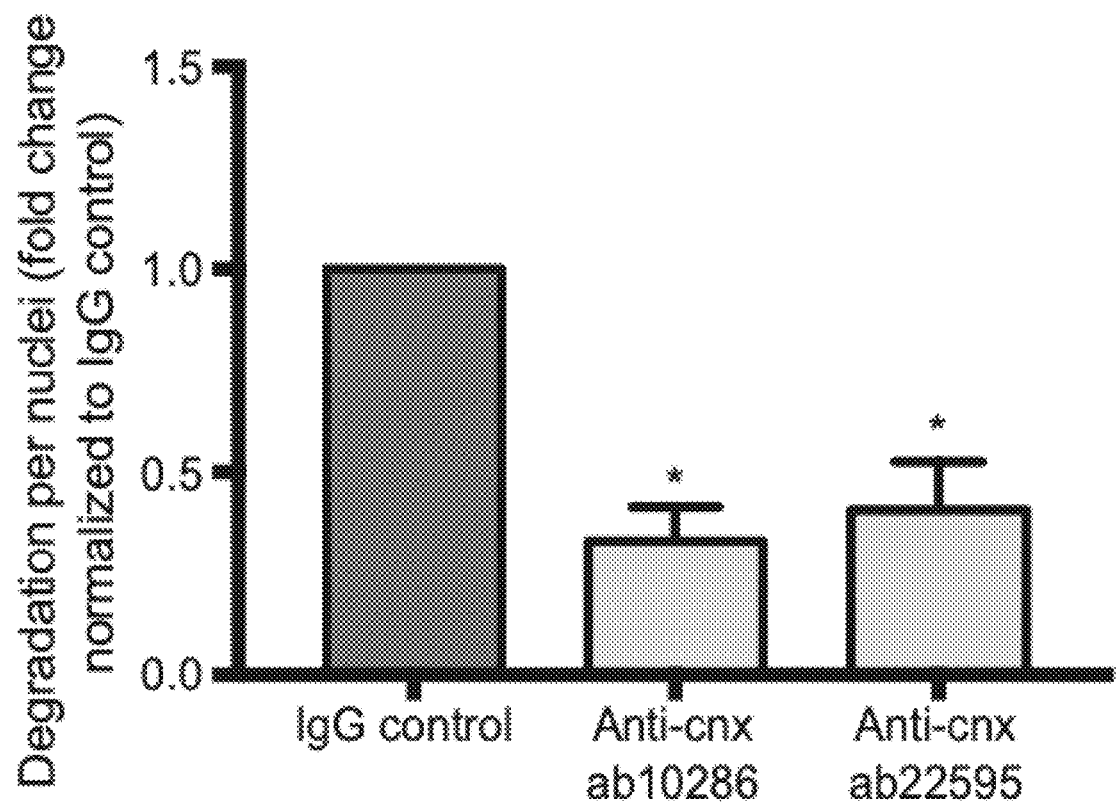
FIG. 8E is a drawing showing quantification of ECM degradation assay of NIH3T3vSrc cells incubated with control antibody (IgG control) or 2 different anti-Cnx antibodies. Values indicate the mean±SEM of normalized fold change for 3 replicates. *p<0.05 compared to IgG control.

To test Huh7 liver cancer cells, we used liver-derived native porcine ECM. To block Cnx function, cells were incubated with an anti-Cnx antibody targeting the extracellular domain. The antibody resulted in ~80% reduction (FIG. 2A, FIG. 2B). We repeated the experiment with MDA ER-G2 and a connective ECM derived from rat tail and obtained very similar results (FIG. 2C). Finally, we repeated the assay with NIH3T3vSrc and rat tail ECM. Compared to the other two models, NIH3T3vSrc are much more active at degrading ECM. Again, Cnx antibodies were able to inhibit degradation significantly (FIG. 8E).

Figure 2D:
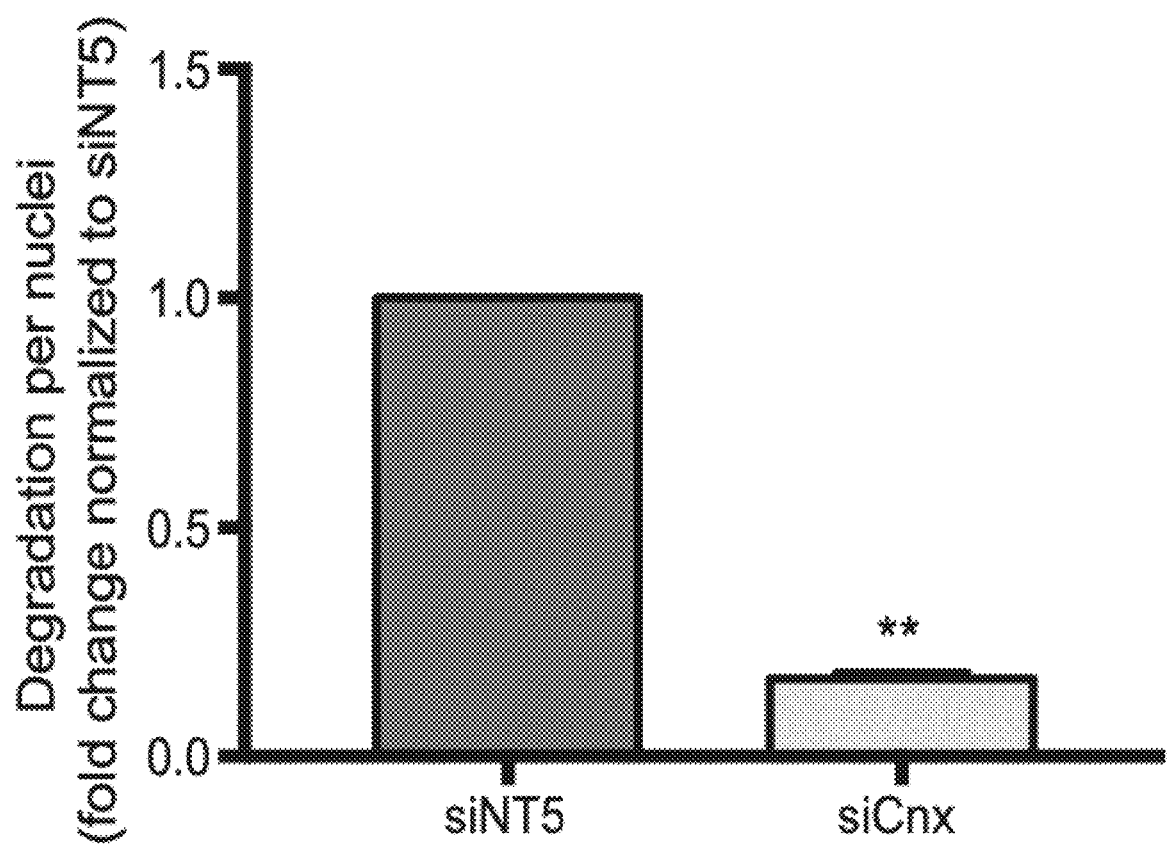

To discount a possible steric hindrance effect of the antibodies and establish the functional requirement of surface Cnx, we aimed to deplete the protein by siRNA treatment. As RNA interference in Huh7 was technically difficult, we performed the test in MDA ER-G2 and NIH3T3vSrc, and both systems resulted in a similar block of matrix degradation (FIG. 2D, FIG. 8D).

Figure 2E:
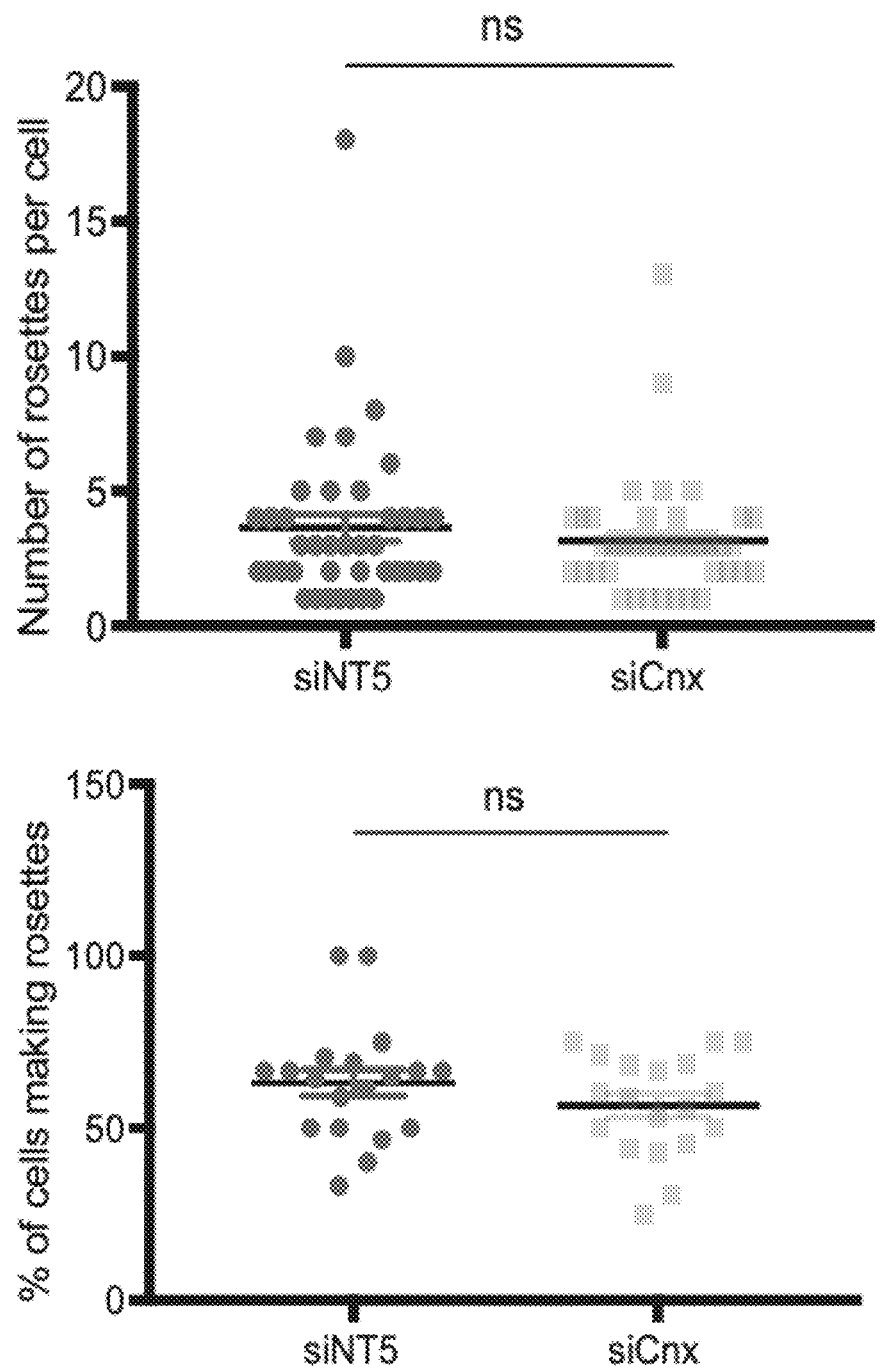
Figure 8F:
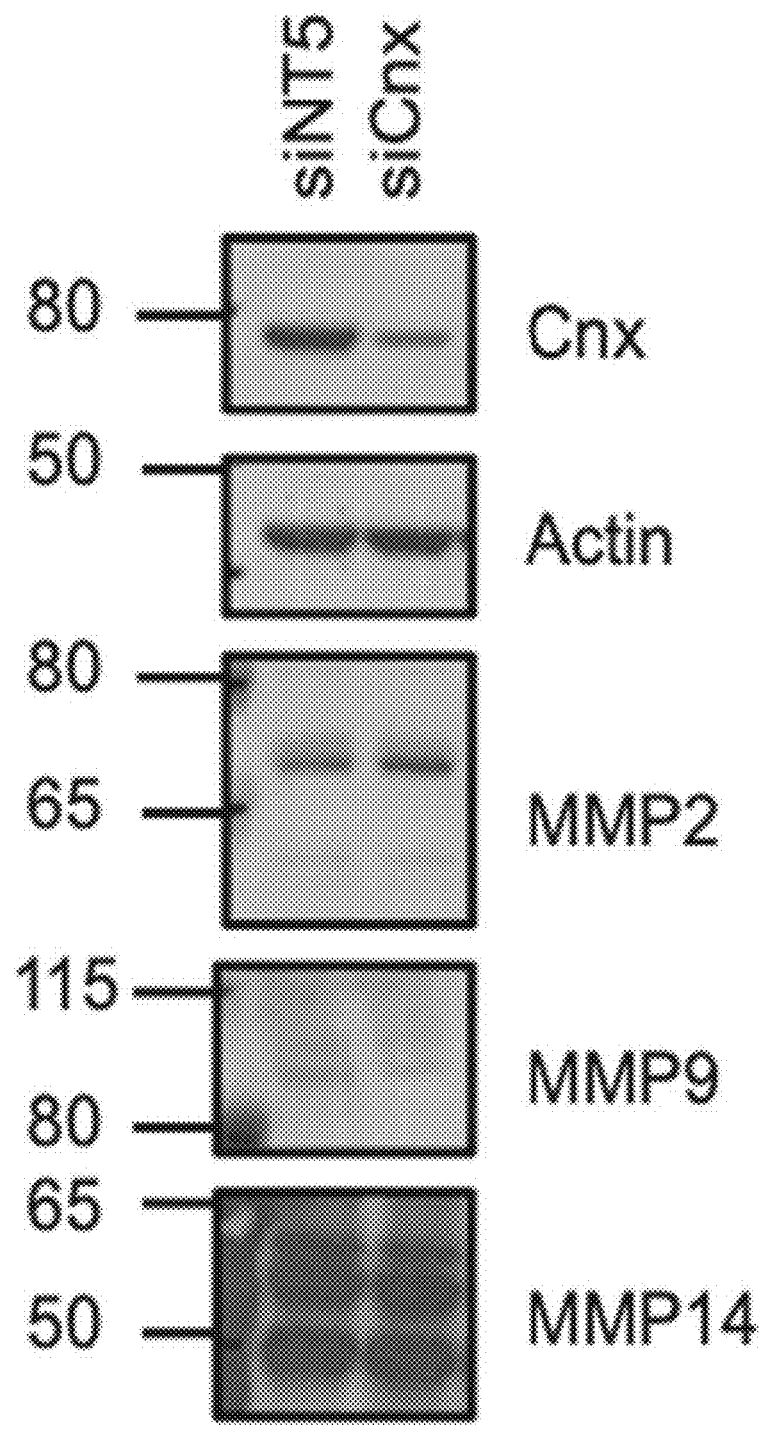
FIG. 8F is a drawing showing an immunoblot analysis of MMPs protein level in NIH3T3vSrc transfected with control siRNA (siNT5) or siRNA against Cnx (siCnx).
Figure 8G:
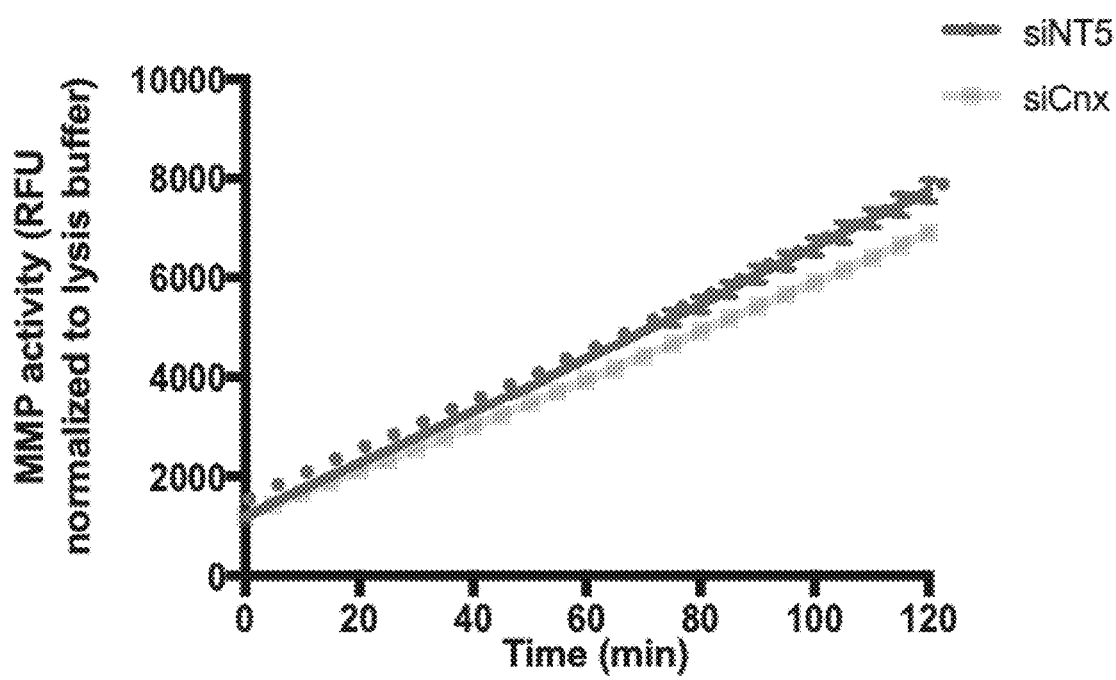
FIG. 8G is a drawing showing quantification of MMP activity by FRET assay of MDA ER-G2 cells transfected with control siRNA (siNT5) or siRNA against cnx (siCnx).
Figure 8H:
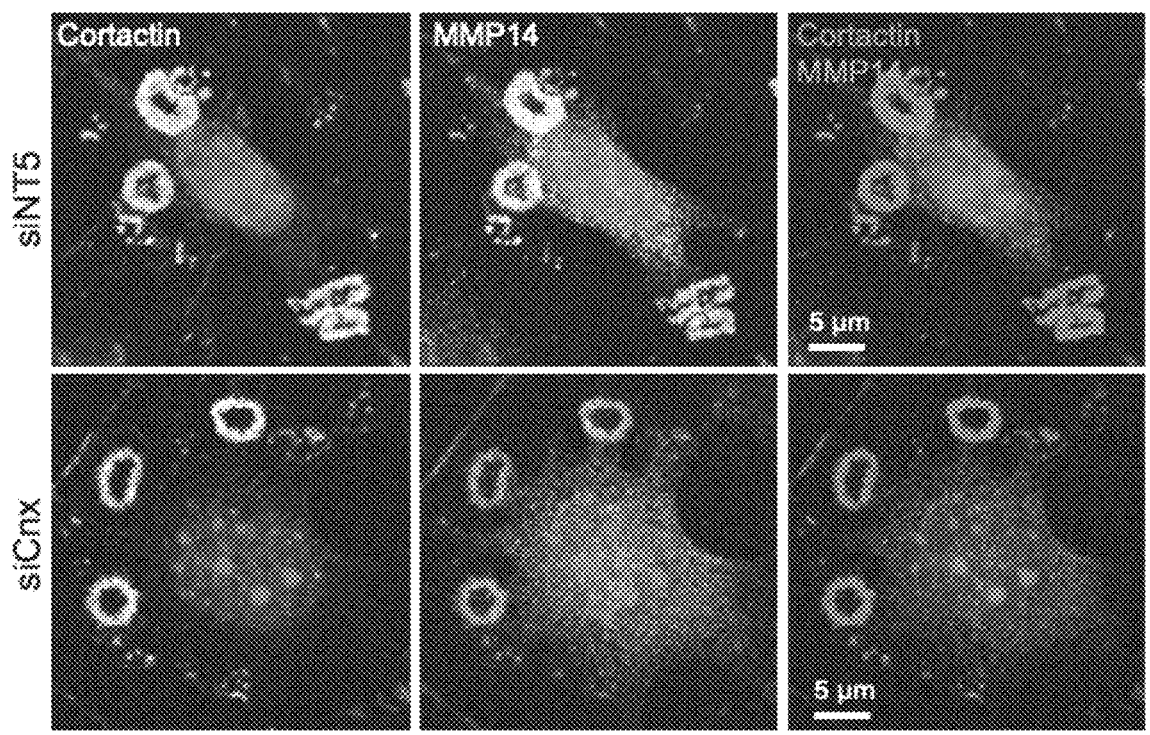
FIG. 8H is a drawing showing immunofluorescence of NIH3T3vSrc cells transfected with control siRNA (siNT5) or siRNA against Cnx (siCnx) and stained with MMP14 and the invadosome marker cortactin. Scale bar, 5 µm.

To better understand this Cnx requirement, we tested whether Cnx depletion affected invadosomes formation, which we measured in NIH3T3vSrc because of the abundance of invadosomes and ease of detection in these cells (FIG. 2E). Given the lack of effect, we hypothesized an effect on Matrix Metalloproteinases and measured MMP2, 9 and 14 abundance by western blot (FIG. 8F). We also measured MMPs activity in a cell lysate and MMP14 localization in invadosomes rosettes after Cnx depletion (FIG. 8G, FIG. 8H). However, we could not detect any difference in any of these assays, suggesting that Cnx is interacting directly with the ECM.

Figure 2F:
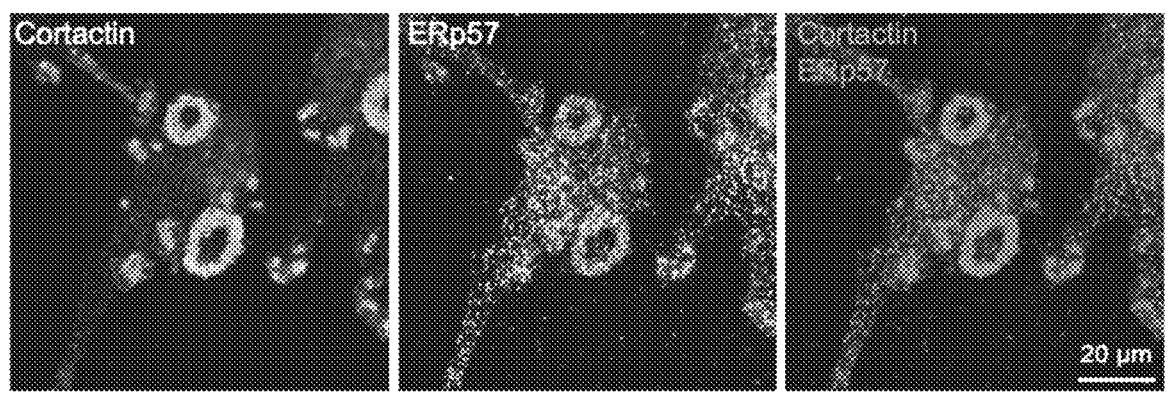
Figure 2G:
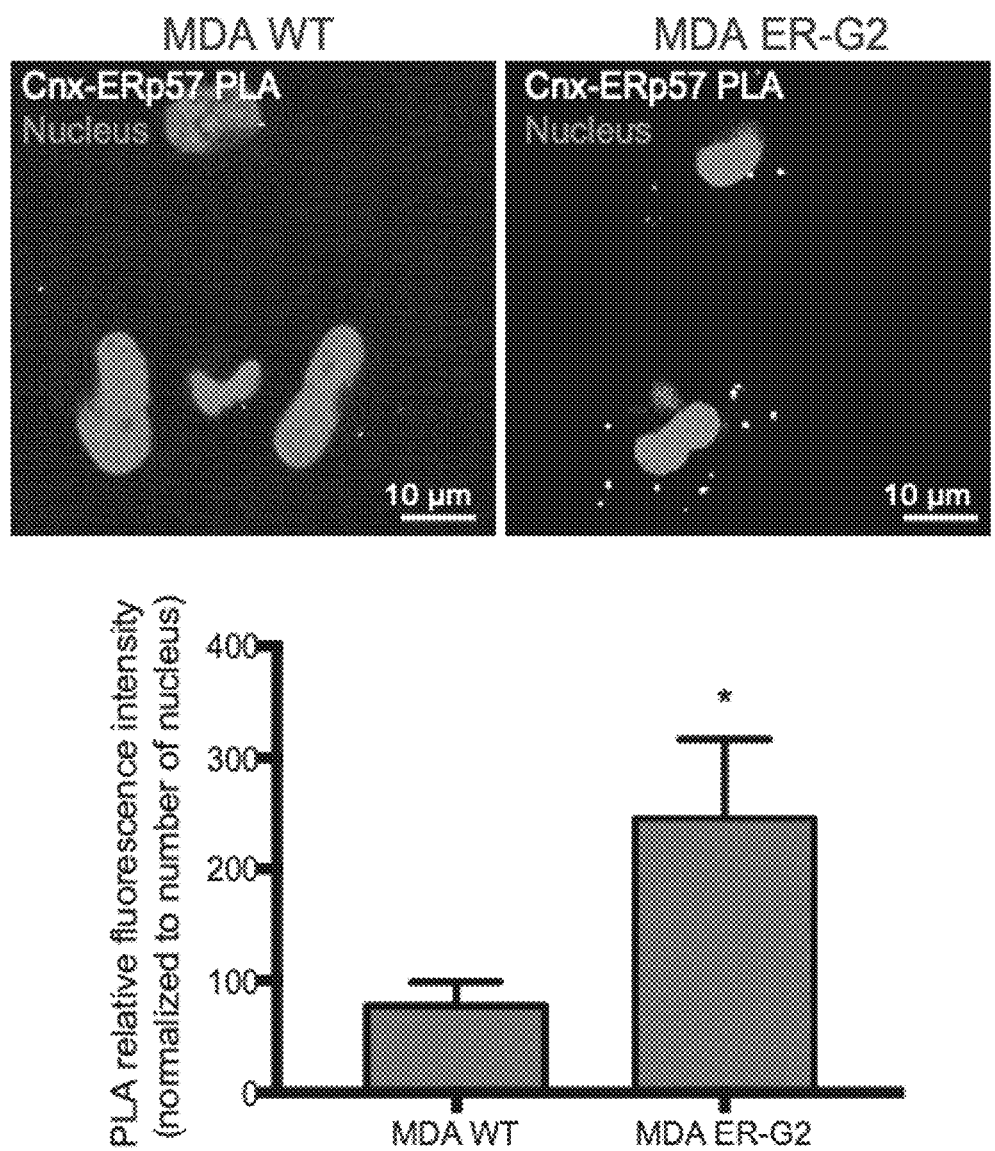
Figure 2H:
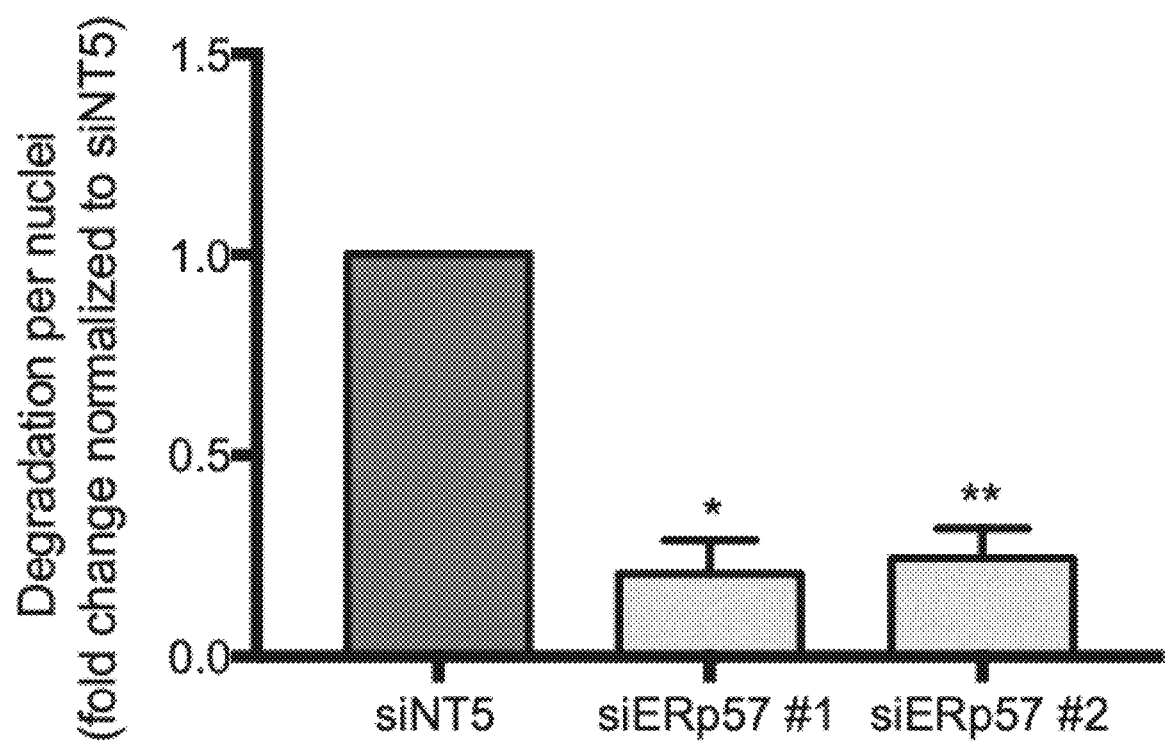
Figure 2I:
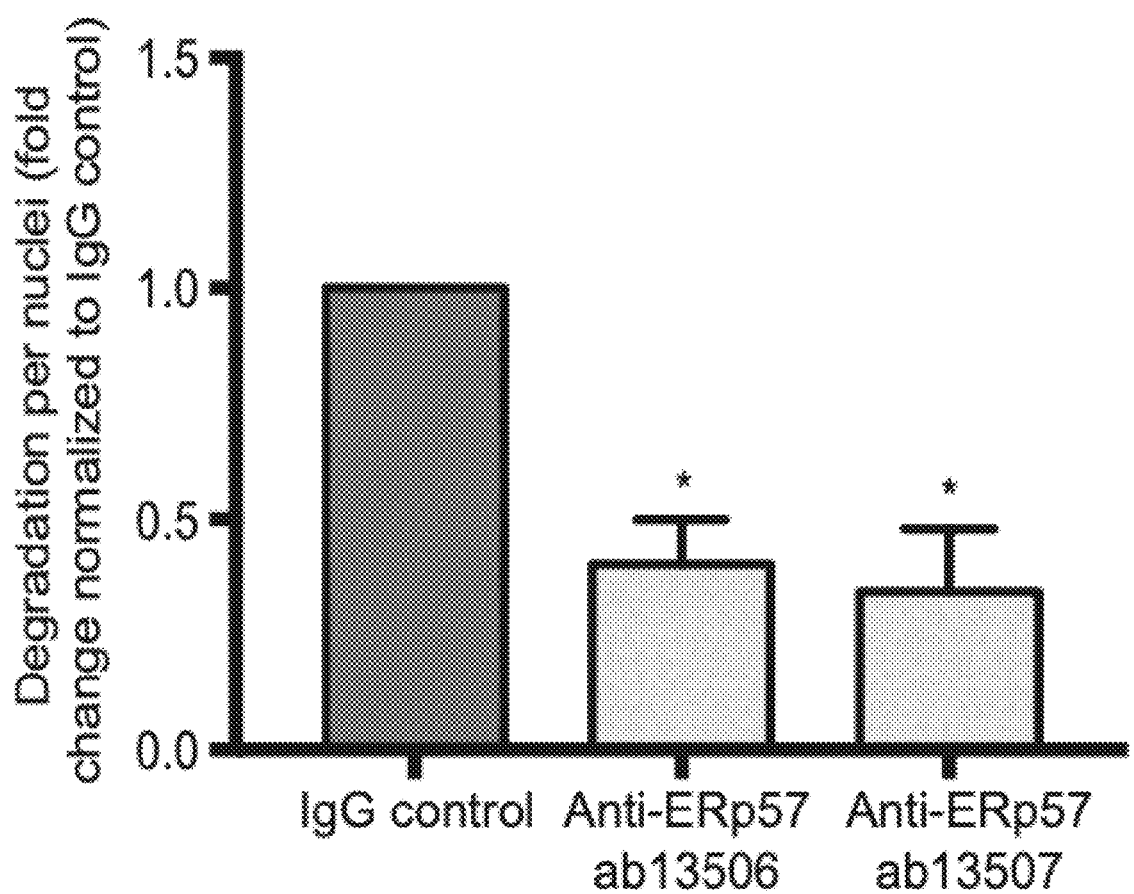

Example 4. Results: A Cell Surface Cnx-ERp57 Complex at Invadosomes is Required for Degradation To understand the role of Cnx at the surface, we sought to identify potential binding partners in invadosomes. ERp57 is an oxidoreductase known to interact with Cnx. We found that ERp57, like Cnx is enriched in invadosomes in the cell types we tested. In NIH3T3vSrc cells, ERp57 localizes clearly to invadosomes rosettes (FIG. 2F). This colocalization suggested that the two proteins form a complex in these structures as they do in the ER. To test this hypothesis, a proximity ligation assay was carried out in live and intact MDA ER-G2 cells and MDA-MB-231 for comparison. The signal was close to background levels in wild-type MDA cells and increased by ~10 fold in MDA ER-G2 (FIG. 2G). This strongly suggests that Cnx and ERp57 interact at the cell surface. Next, ERp57 was depleted with two different sets of siRNA in MDA ER-G2, where the depletion resulted in about six fold reduction in degradative activity (FIG. 2H). In NIH3T3vSrc, a mouse specific siRNA targeting Cnx similarly reduced ECM degradation (FIG. 8D). Finally, similar to the Cnx results, incubation of live MDA ER-G2 with anti-ERp57 antibodies blocked collagen degradation (FIG. 2I).

Example 5. Results: Glycosylated Cnx is Required for ECM Degradation

Figure 3A:
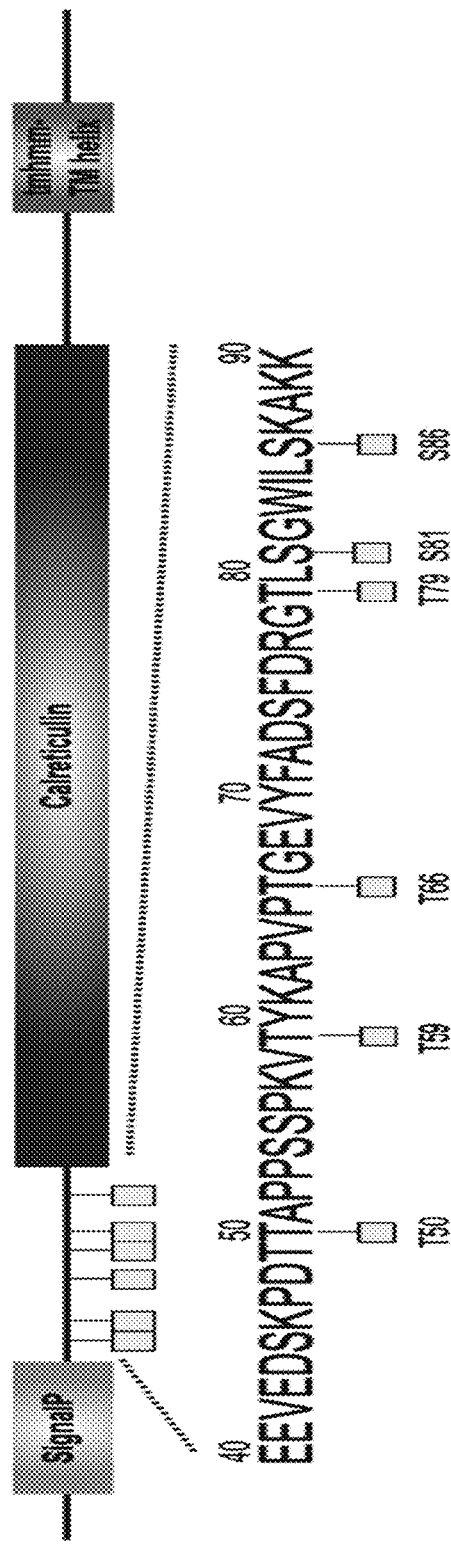
FIGS. 3A to 3F are drawings showing that glycosylated Cnx is required for ECM degradation
Figure 3B:
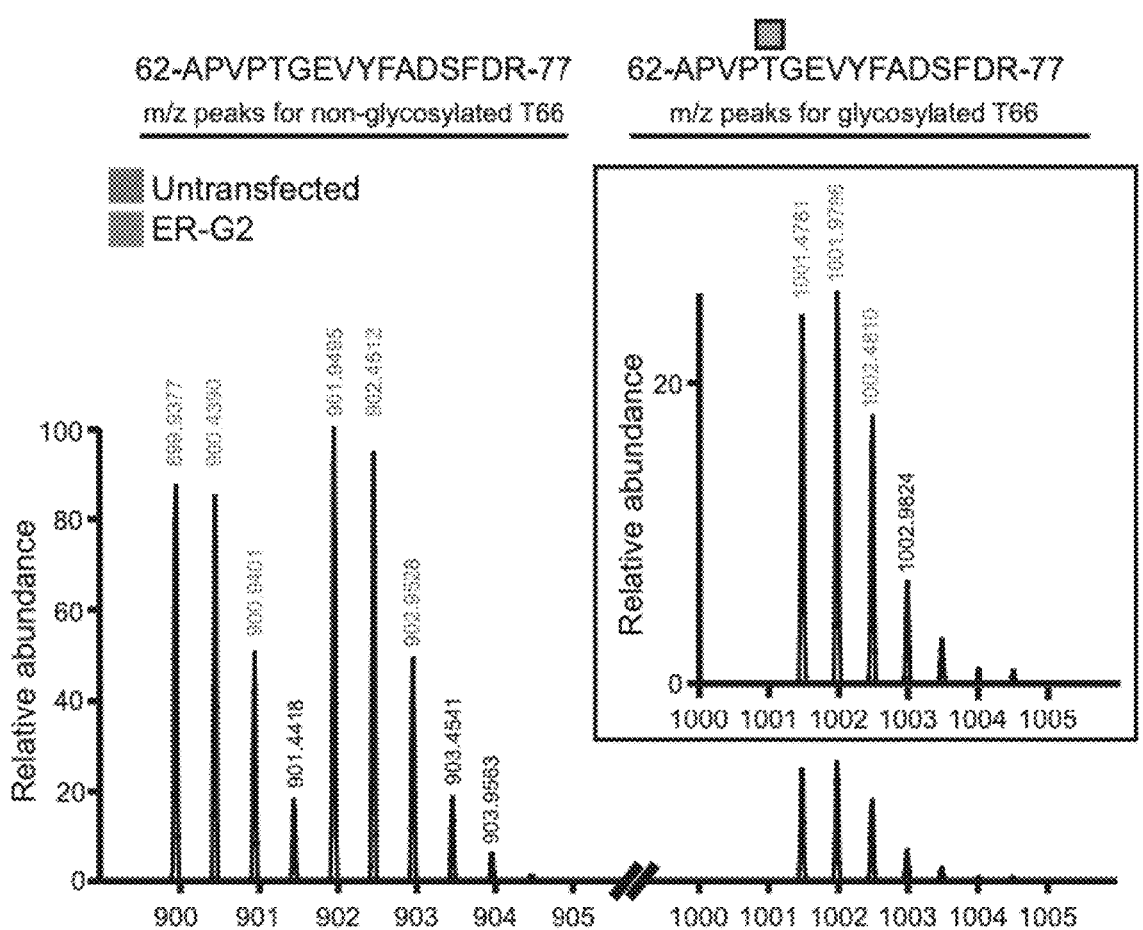
Figure 3C:
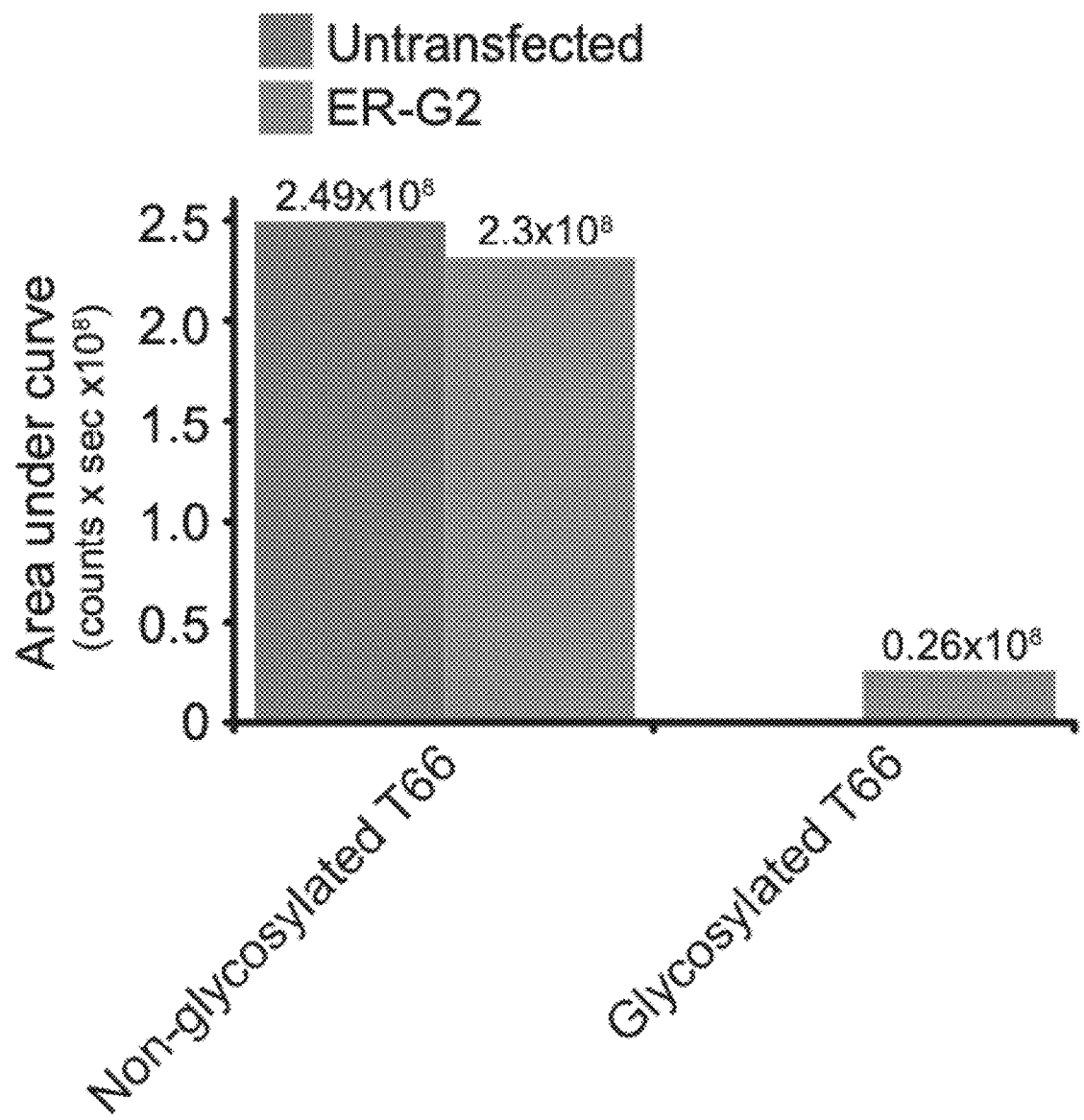

Next, we employed mass spectrometry to identify the glycosylation sites in Cnx. This approach has been greatly simplified by the use of genetically manipulated "SimpleCells" producing short O-glycans[39]. To apply the technique, we depleted HeLa SimpleCells of ERK8, a kinase that dynamically represses GALA[20]. We found that Cnx glycosylation occurred on a cluster of residues in the N-terminal region of the protein (FIG. 3A). Because of the clustered nature of Tn residues, we used a range of peptidases to map the glycosylation sites and identified 6 sites: T50, T59, T66, T79, S81 and S86. We also used dimethyl-labeling based mass spectrometry to quantify the increase of glycosylation and found that all sites were increased by GALA, with S81 and S86 the most affected, with a ~6-fold increase in glycosylation. We also attempted to quantify the proportion of unmodified and glycosylated peptides but could only obtain data for T66. Quantification of peaks revealed that only about 10% of the pool of T66-containing peptide becomes glycosylated, suggesting only a fraction of Cnx gets glycosylated (FIG. 3B, FIG. 3C). While this analysis remains semi-quantitative, it suggests an explanation for why only a fraction of Cnx is translocated to the cell surface. In sum, a N-terminal cluster of residues becomes hyperglycosylated in a pool of Cnx after GALA activation.

Figure 3D:
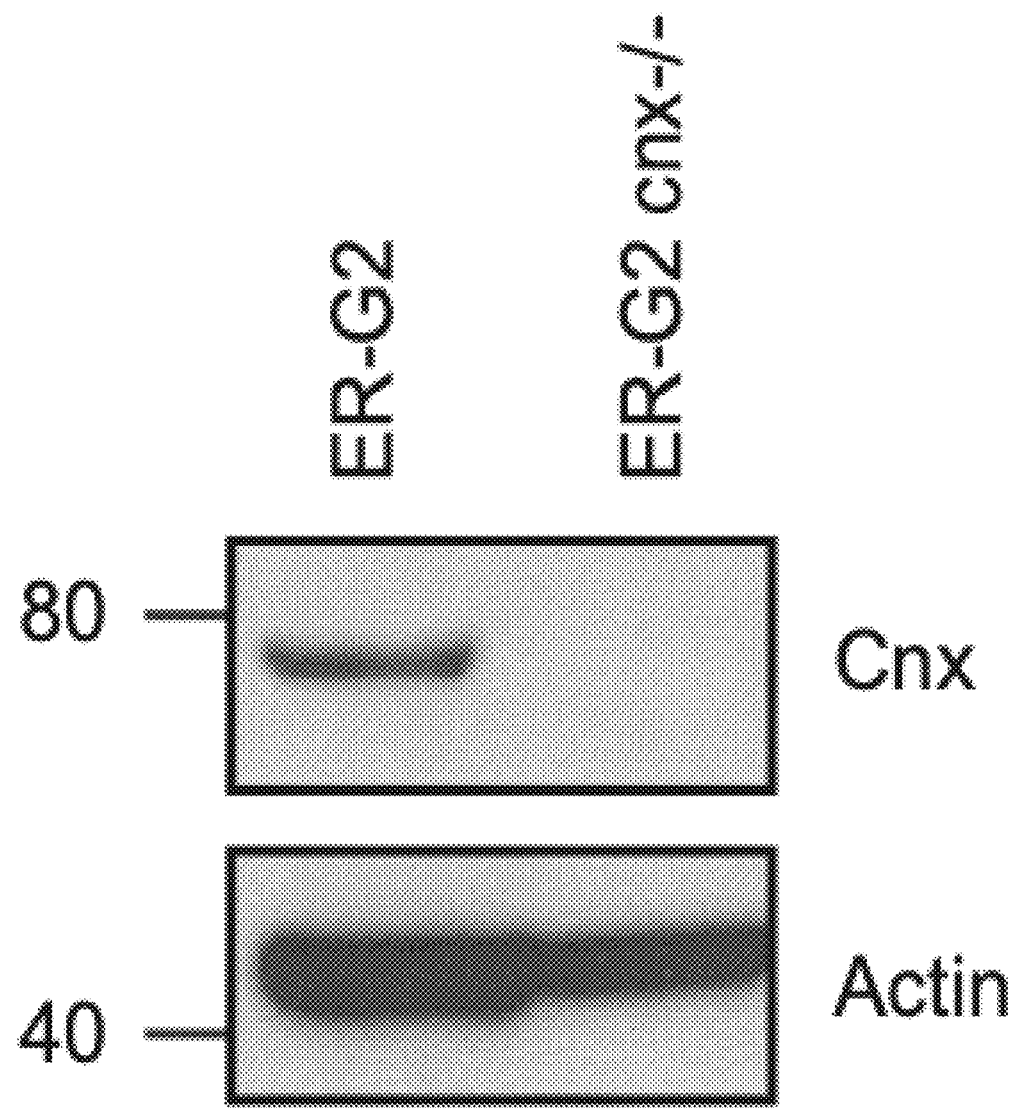
Figure 3E:
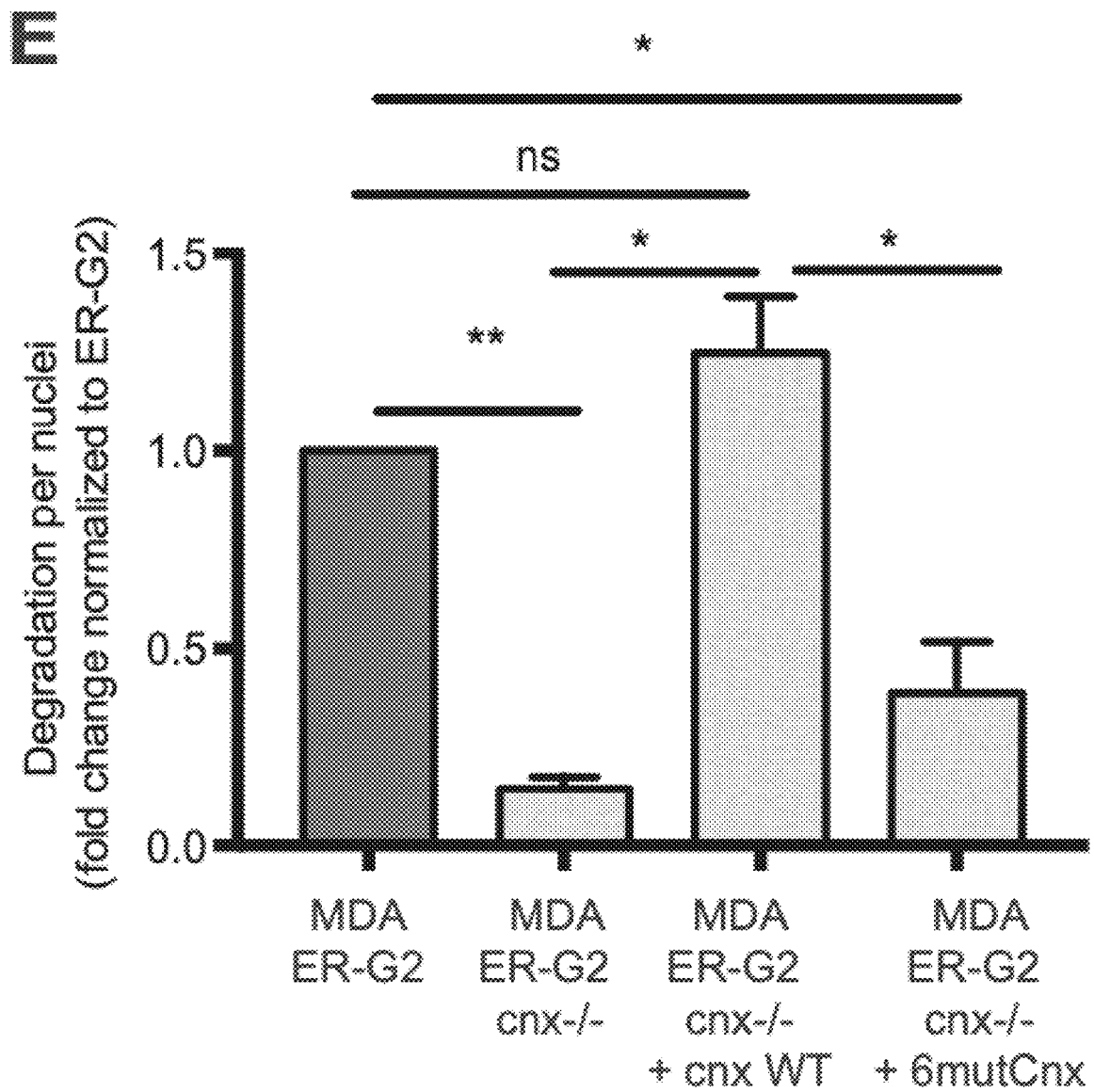
Figure 3F:
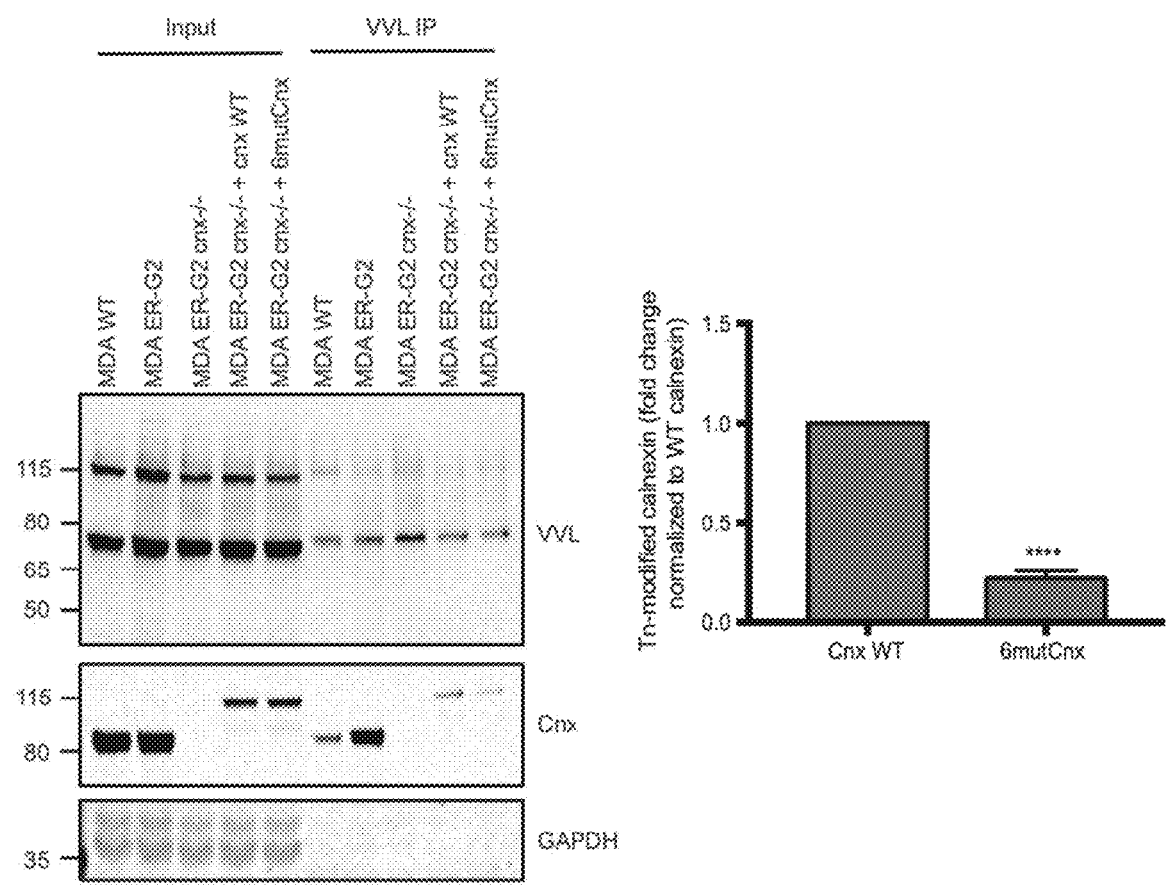

To test the requirement Cnx glycosylation for its translocation at the cell surface, we generated an MDA ER-G2 cell line depleted of Cnx using CRISPR (FIG. 3D). These mutant cells displayed a strongly reduced capacity for collagen degradation (FIG. 3E). We also generated a Cnx construct with all six glycosylation sites mutated (6mutCnx). Both wild-type Cnx and 6mutCnx were transfected into MDA ER-G2 Cnx−/− cells and assessed for Tn modification (FIG. 3F). This test revealed strongly decreased but residual glycosylation in the 6mutCnx construct, suggesting either that previously undetected glycosylation sites are present or that GALNT2 might glycosylate residues in the mutant it does not glycosylate in the wild-type form. When assessed for collagen degradation in MDA ER-G2 Cnx−/− cells, the wild type Cnx was able to fully restore degradative activity. By contrast, the mutant had only a marginal restorative effect (FIG. 3E).

Figure 4A:
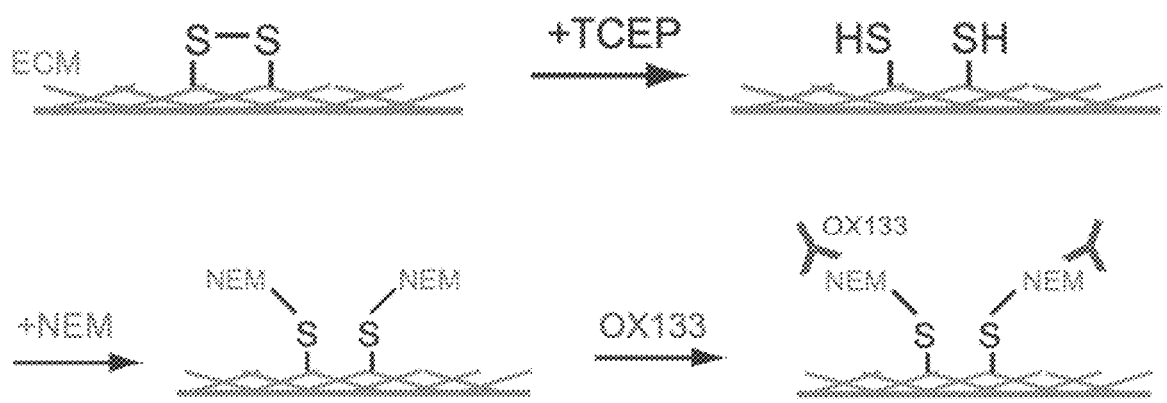
FIGS. 4A to 4F are drawings showing that Cnx and ERp57 are required for ECM disulfide bonds reduction
Figure 4B:
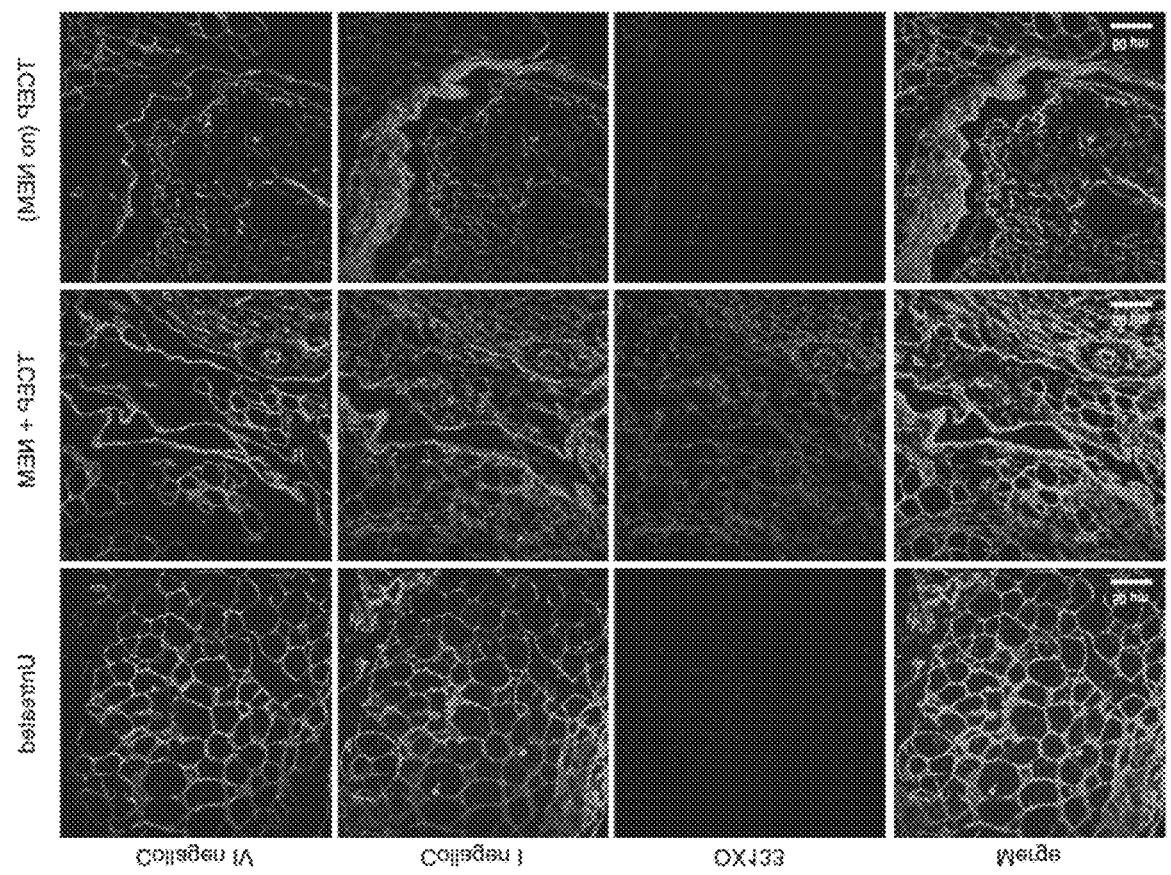
Figure 9A:
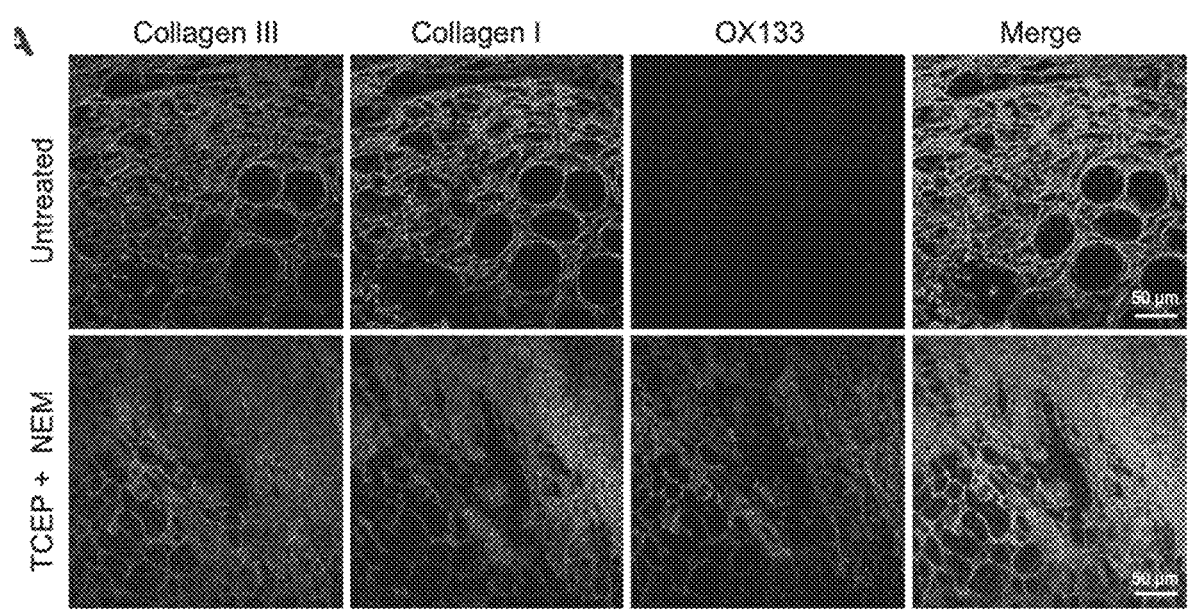
FIG. 9A is a drawing showing immunofluorescence of collagens I and III and OX133 on decellularized liver, untreated or treated with TCEP and NEM. Scale bar, 50 µm.
Figure 9B:
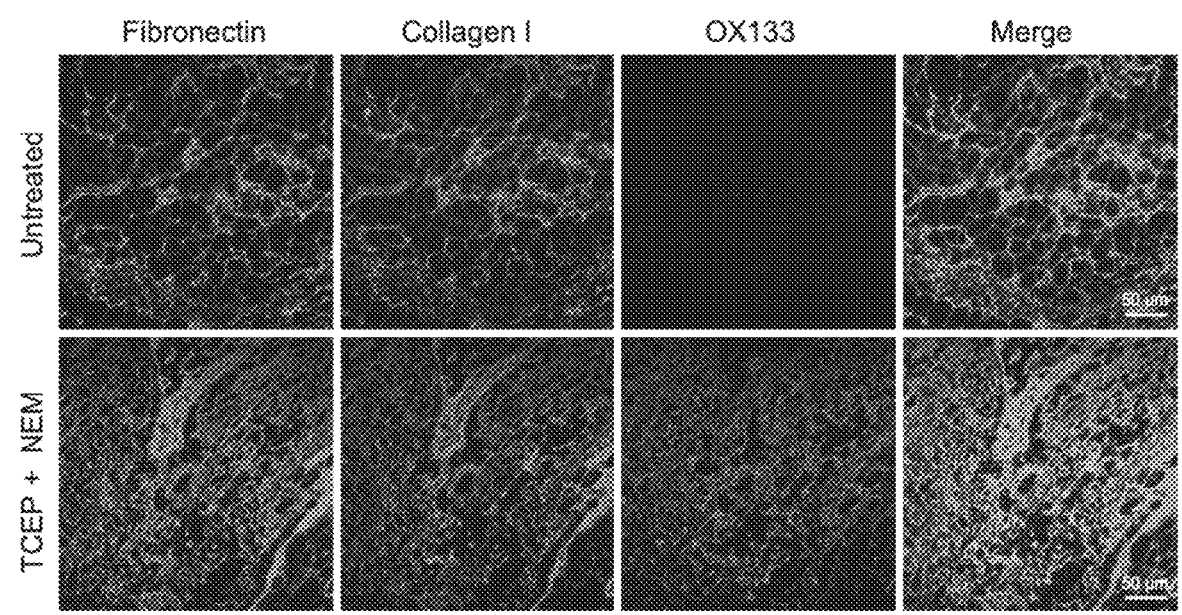
FIG. 9B is a drawing showing immunofluorescence of collagen I and fibronectin on decellularized liver, untreated or treated with TCEP and NEM. Scale bar, 50 µm.
Figure 9C:
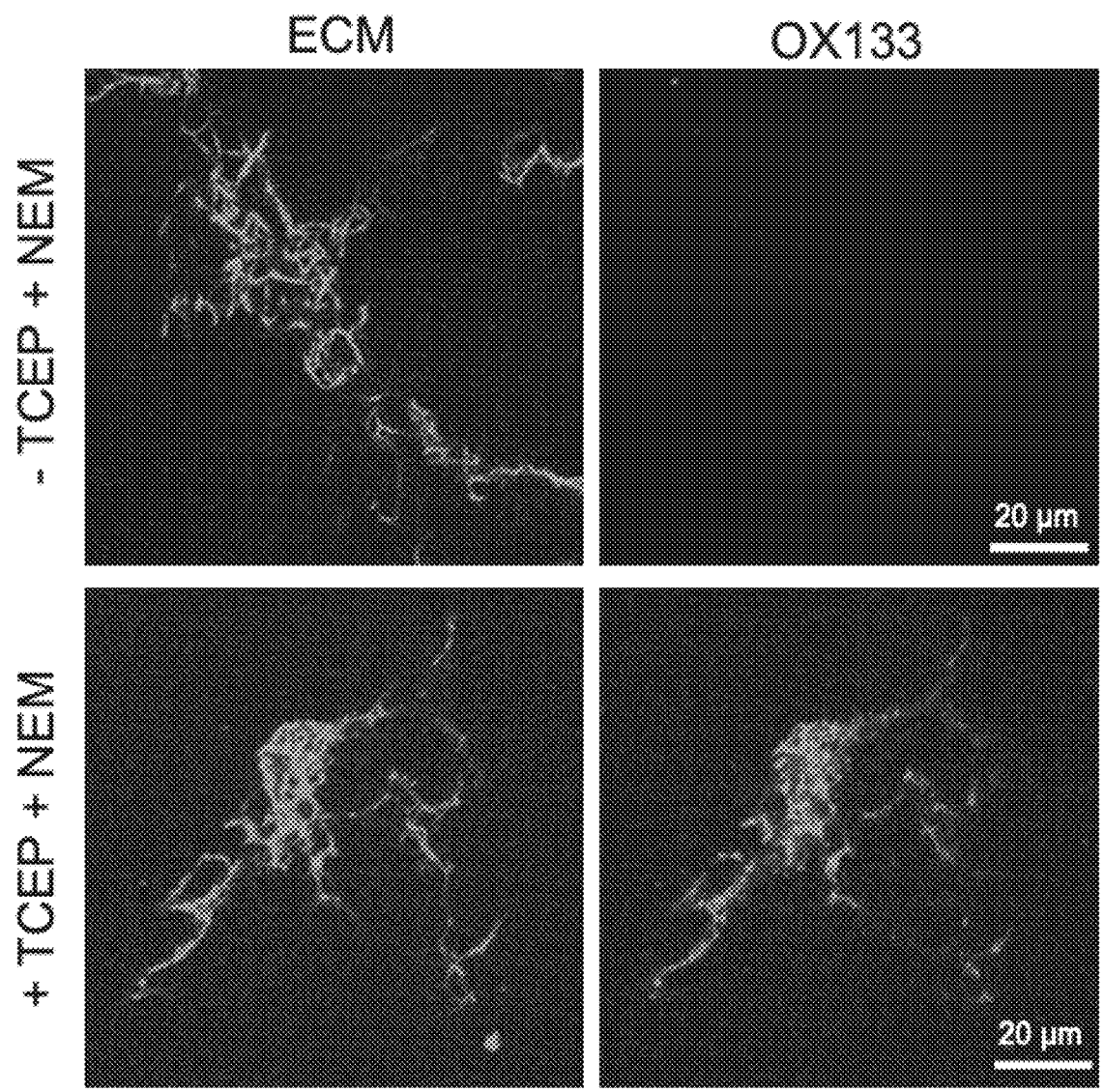
FIG. 9C is a drawing showing immunofluorescence of rat tail ECM, treated or non-treated with TCEP and NEM and stained with OX133 antibody. Scale bar, 20 µm.

Example 6. Results: Cnx and ERp57 are Required for Extracellular ECM Disulfide Bond Reduction In the ER, the Cnx-ERp57 complex mediates the formation and isomerization of disulfide bonds in neo-synthesized proteins[40]. To explain the surprising requirement of the same complex for matrix degradation, we hypothesized it could mediate the reduction of disulfide bonds in extracellular ECM fibers. To reveal disulfide bonds in ECM preparations, we used the reducing agent tris(2-carboxyethyl)phosphine (TCEP), followed by reaction with N-ethylmaleimide (NEM). The resulting cysteine-conjugated NEM could then be revealed using the OX133 antibody[41] (FIG. 4A). To test whether disulfide bonds are present in liver ECM, we prepared decellularized mouse liver tissue. The decellularized matrix presented as a meshwork with a diamond-shaped pattern, the fibers staining for Collagen I, III, IV, and fibronectin (FIGS. 4B, FIG. 9A, FIG. 9B). Using the disulfide bonds revelation technique, we obtained abundant OX133 staining on these fibers, suggesting a high level of cross-linking (FIG. 4B). Interestingly, we also observed significant perturbations of matrix organisation after TCEP treatment, suggesting the reduction of disulfide bonds had loosened the matrix (FIG. 4B). We also tested the commercially-sourced liver porcine ECM and the rat tail connective tissue and obtained in both cases an abundant staining with OX133 after TECP/NEM treatment (FIG. 9C). This staining was entirely dependent on TCEP and NEM. In all cases, most of the OX133 signal colocalized with collagen fibers. In sum, our results indicate that in both liver and connective ECM, there is an abundance of collagen associated proteins cross-linked by disulfide bonds.

Figure 4C:
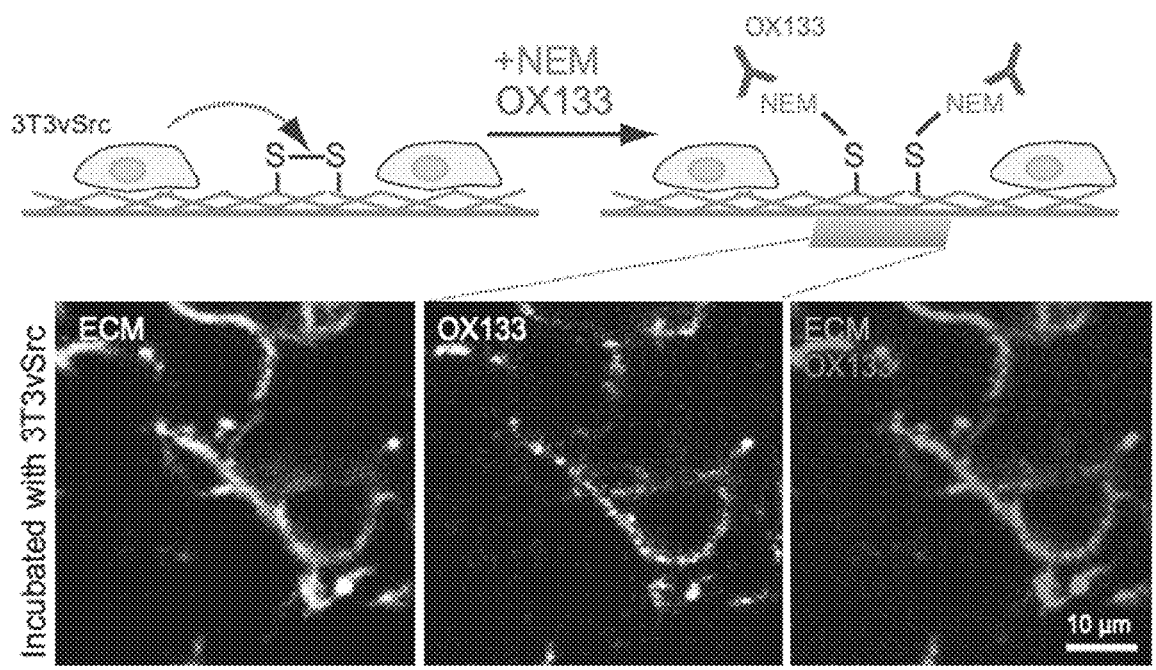
Figure 4D:
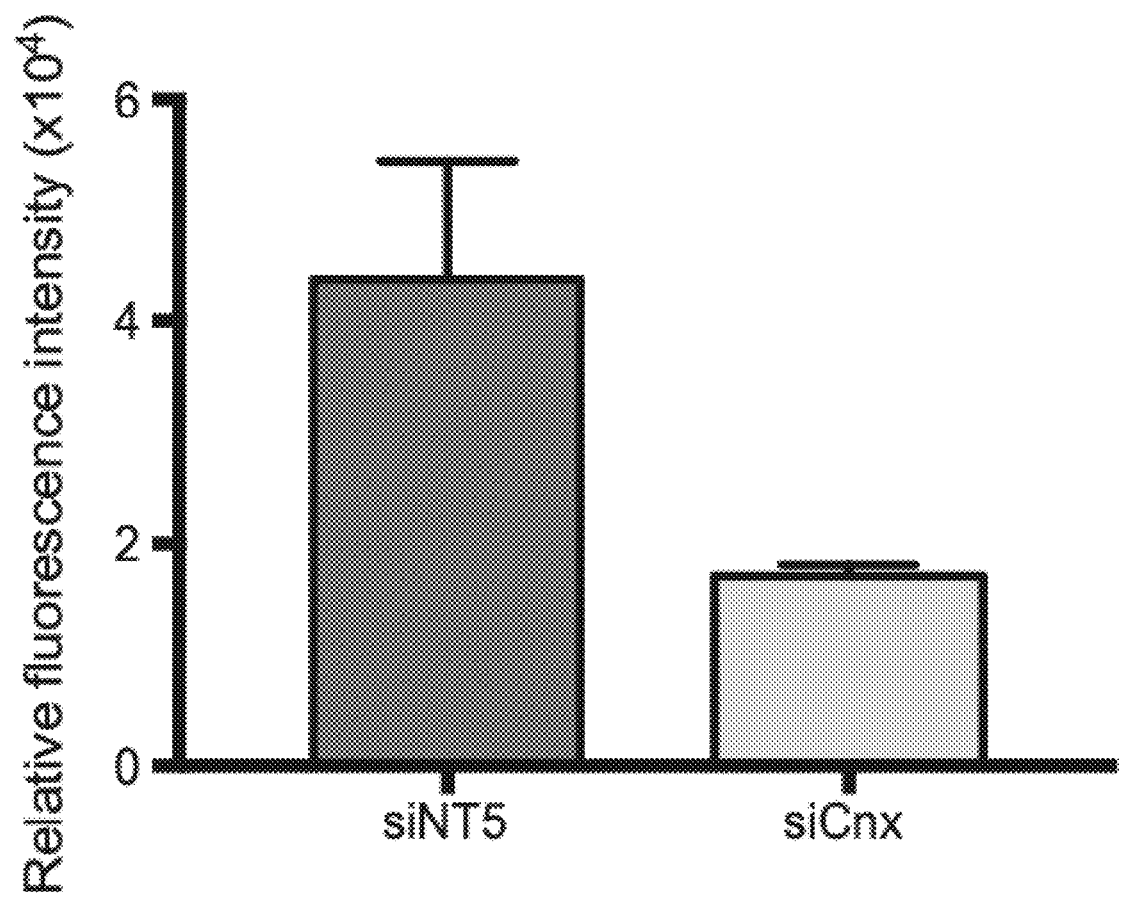

To test if cells are able to reduce these disulfide bonds, the actively degrading NIH3T3vSrc cells were sparsely seeded on rat tail ECM. The cells were treated with the MMP inhibitor GM6001 to prevent collagen degradation. NEM was then added to reveal reduced cysteines and after 16 hours, coverslips were fixed and labeled. In the presence of NIH3T3vSrc cells, collagen fibers became markedly OX133-labeled (FIG. 4C). By contrast, in Cnx depleted cells, staining with OX133 was significantly reduced (FIG. 4D).

Figure 9D:
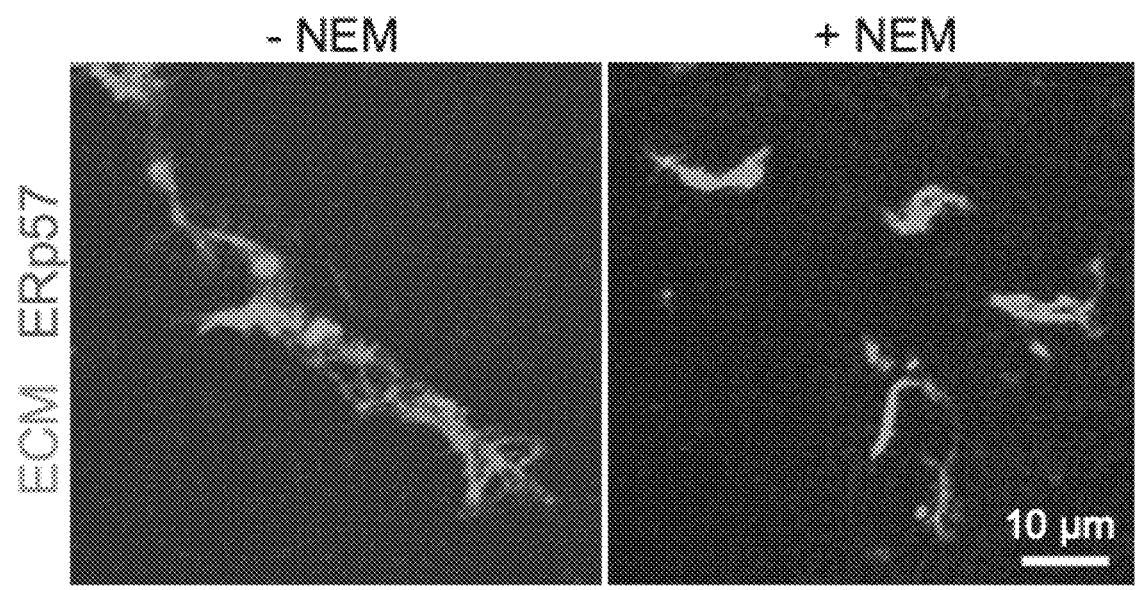
FIG. 9D is a drawing showing immunofluorescence of collagen incubated with NIH3T3vSrc (not shown), with or without NEM, and stained with ERp57 antibody. Collagen was previously coupled to 5-carboxy-X-rhodamin succinimidyl ester before cell seeding. Scale bar, 10 µm

ERp57 contains two thioredoxin domains, each with a pair of cysteines involved in the oxidoreduction of target cysteines[34]. It was previously reported that mutation of a single cysteine in a thioredoxin domain can result in the cross-linking of ERp57 with its client protein through the remaining cysteine. We reasoned that similarly, treatment with NEM might lead to cross-linking of ERp57 to collagen. Sparsely seeded NIH3T3vSrc cells were treated with NEM and GM6001 before fixation and ERp57 labeling. The treatment was conducted overnight to allow cells to move out of areas where ERp57 had been cross-linked. Indeed, some cell-free areas displayed ERp57 staining co-localising with collagen fibers, in a NEM-dependent fashion (FIG. 9D).

Figure 4E:
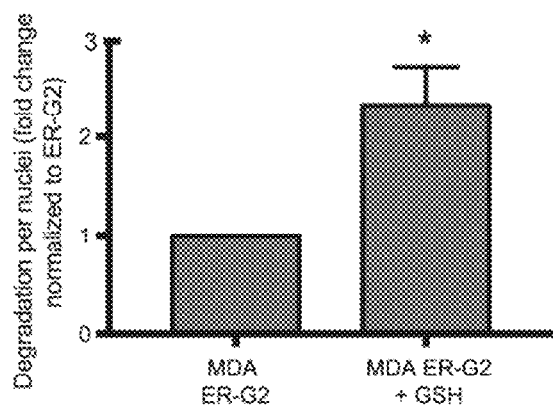
Figure 4E:
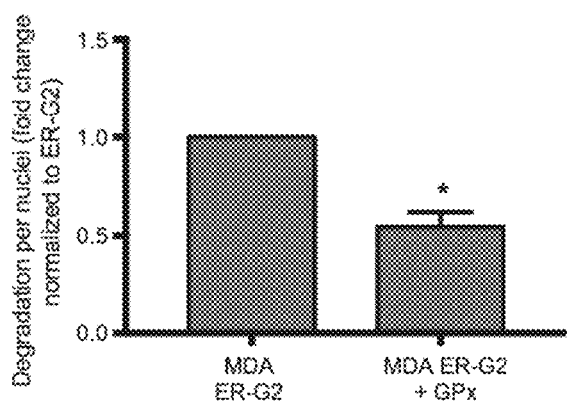
Figure 9E:
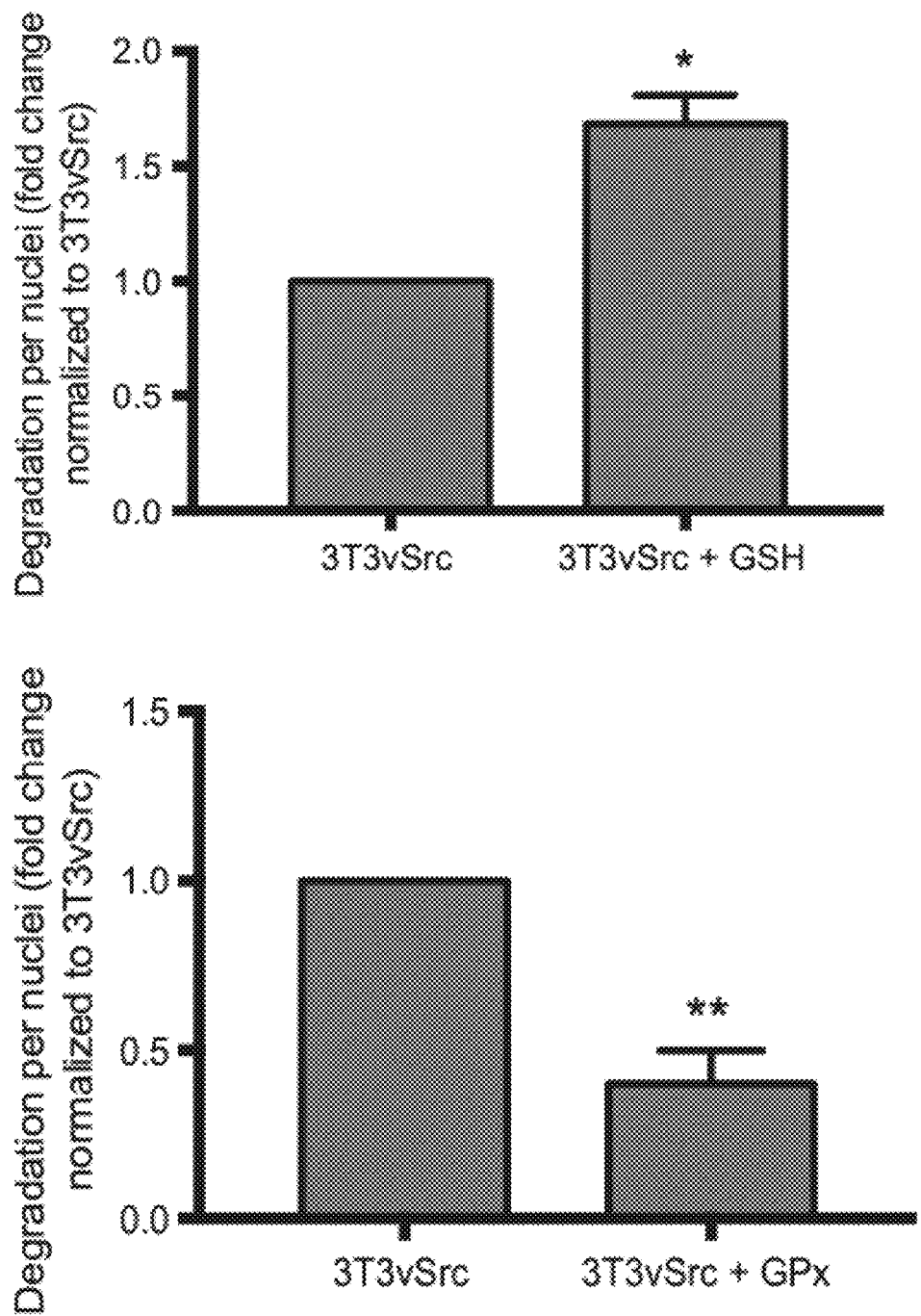
FIG. 9E is a drawing showing quantification of ECM degradation assay of NIH3T3vSrc cells incubated with GSH (+GSH) or with GPx and $H_2O_2$ (+GPx). Values indicate the mean±SEM of normalized fold changes for 3 replicates. *p<0.05 compared to control untreated cells.

To function as a reductase, ERp57 needs a reducing cofactor. Glutathione (GSH) has been shown to directly reduce ERp57[35]. Consistent with GSH involvement, 1 mM GSH supplemented MDA ER-G2 cells and NIH3T3vSrc cells were more efficient at ECM degradation (FIG. 4E and FIG. 9E). Conversely, treating cells with the GSH peroxidase (GPx) and $H_2O_2$ resulted in less efficient ECM degradation (FIG. 4E and FIG. 9E). This strongly suggests that extracellular GSH is the source of reducing electrons.

Figure 4F:
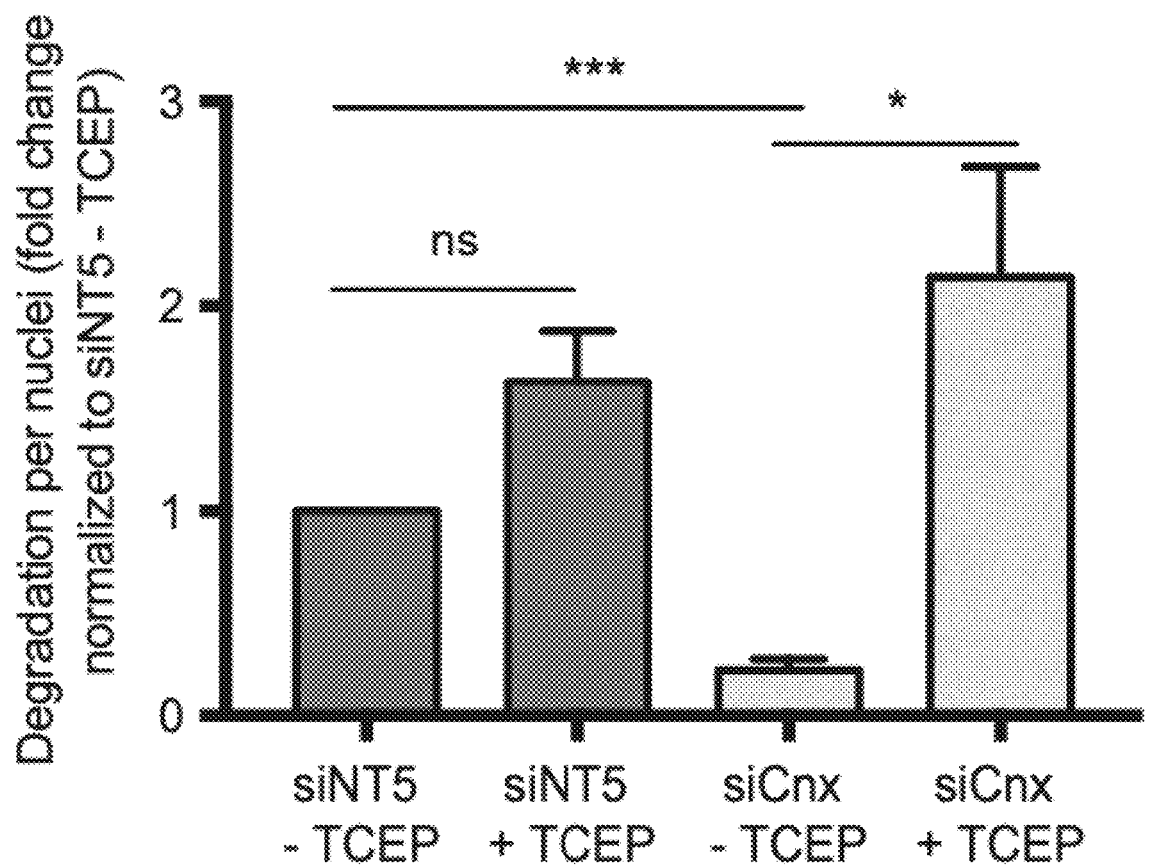
Figure 9F:
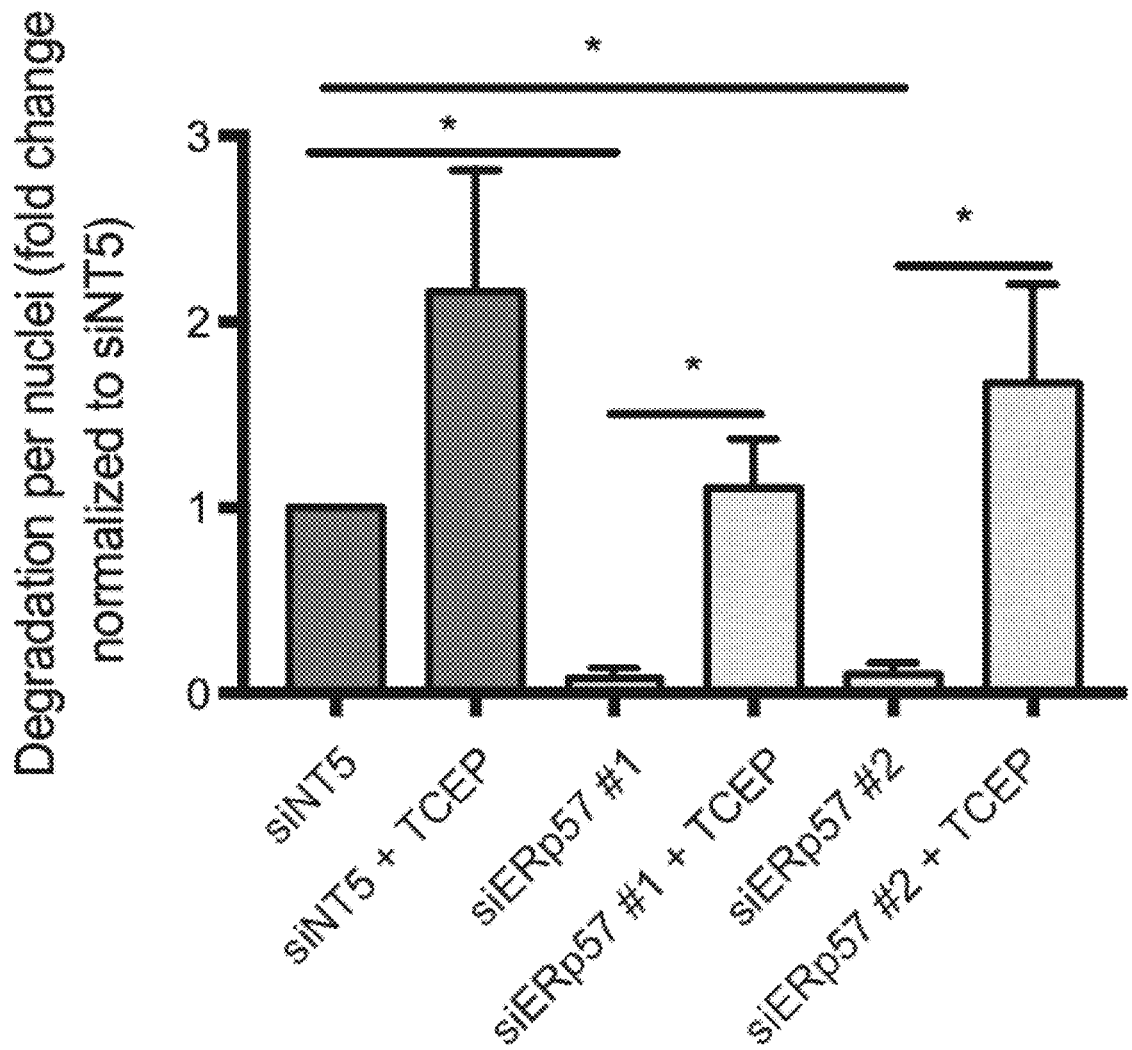
FIG. 9F is a drawing showing quantification of ECM degradation assay of MDA ER-G2 transfected with control siRNA or 2 different ERp57 siRNA (siERp57 #1 and #2). Collagen disulfide bonds were chemically reduced using TCEP (+TCEP) or left untreated (−TCEP) before cell seeding. Values indicate the mean±SEM of normalized fold changes for 3 replicates. *p<0.05

Finally, we reasoned that chemical reduction of ECM disulfide bonds might alleviate the requirement for the Cnx/ERp57 complex. To obtain cells depleted of Cnx, we reverted to MDA ER-G2. Before seeding cells, we pre-treated the ECM with TCEP. In cells depleted of Cnx or ERp57, this pre-treatment completely reversed the inhibitory effect of Cnx depletion (FIG. 4F and FIG. 9F). To note, ECM treatment with TCEP also had a stimulatory effect on ECM degradation in control cells (FIG. 4F and FIG. 10F). Thus, the data indicates that the requirement of the Cnx/ERp57 for ECM degradation is mainly if not exclusively the reduction of disulfide bonds in ECM proteins.

Example 7. Results: Blocking Cnx Function Prevents Metastases Formation

Figure 5A:
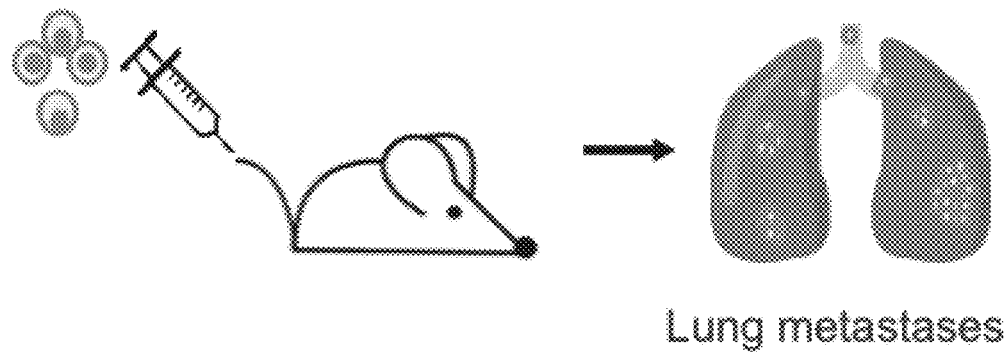
FIGS. 5A to 5G are drawings showing that anti-calnexin antibody treatment prevents tumor metastasis
Figure 5A:
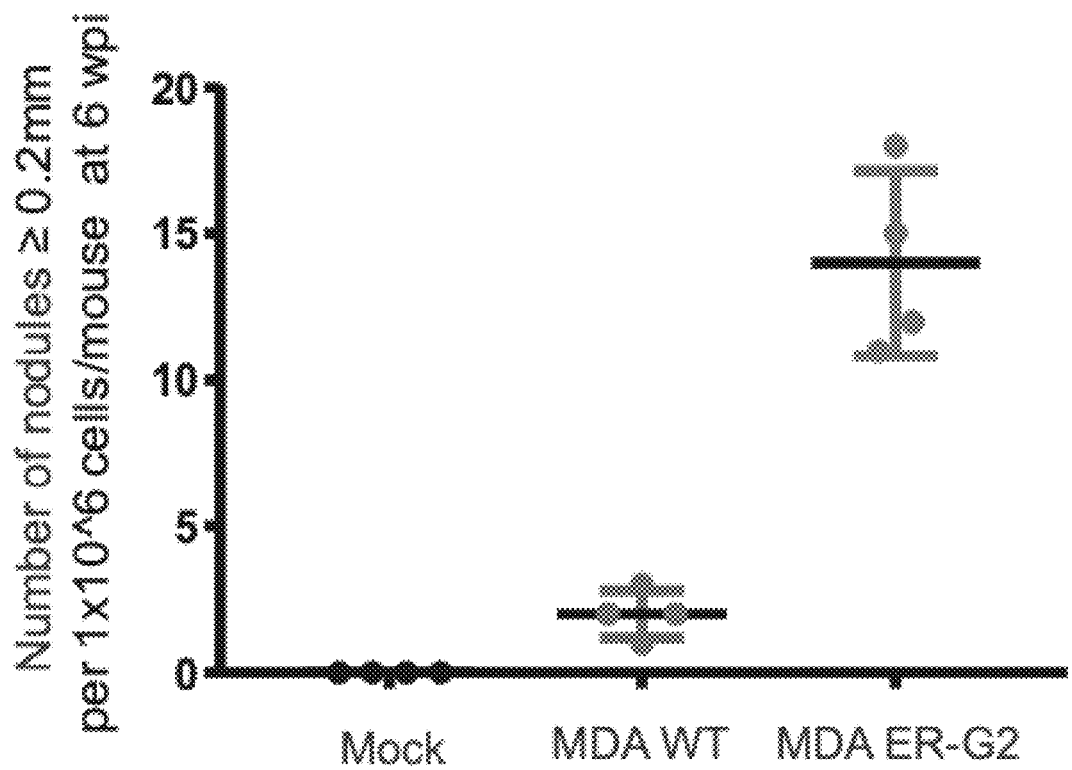
Figure 5B:
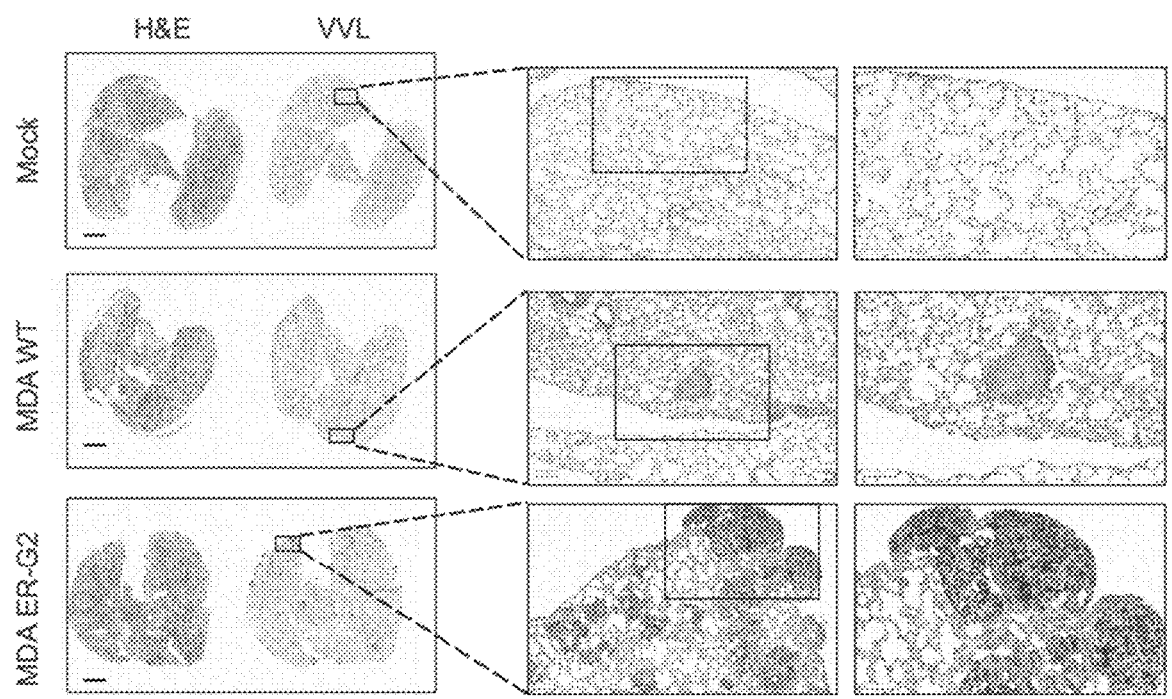
Figure 5C:
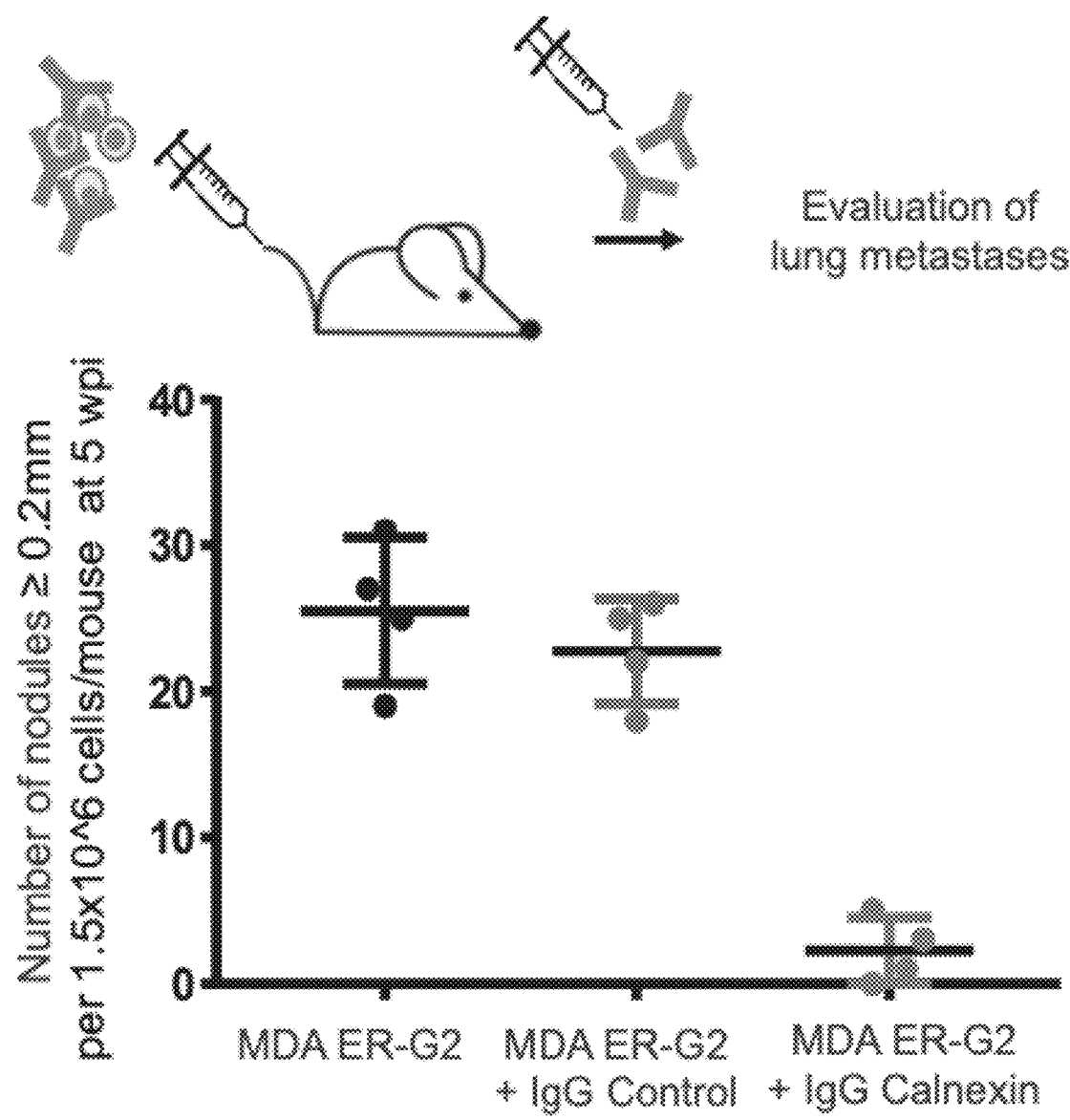
Figure 5D:
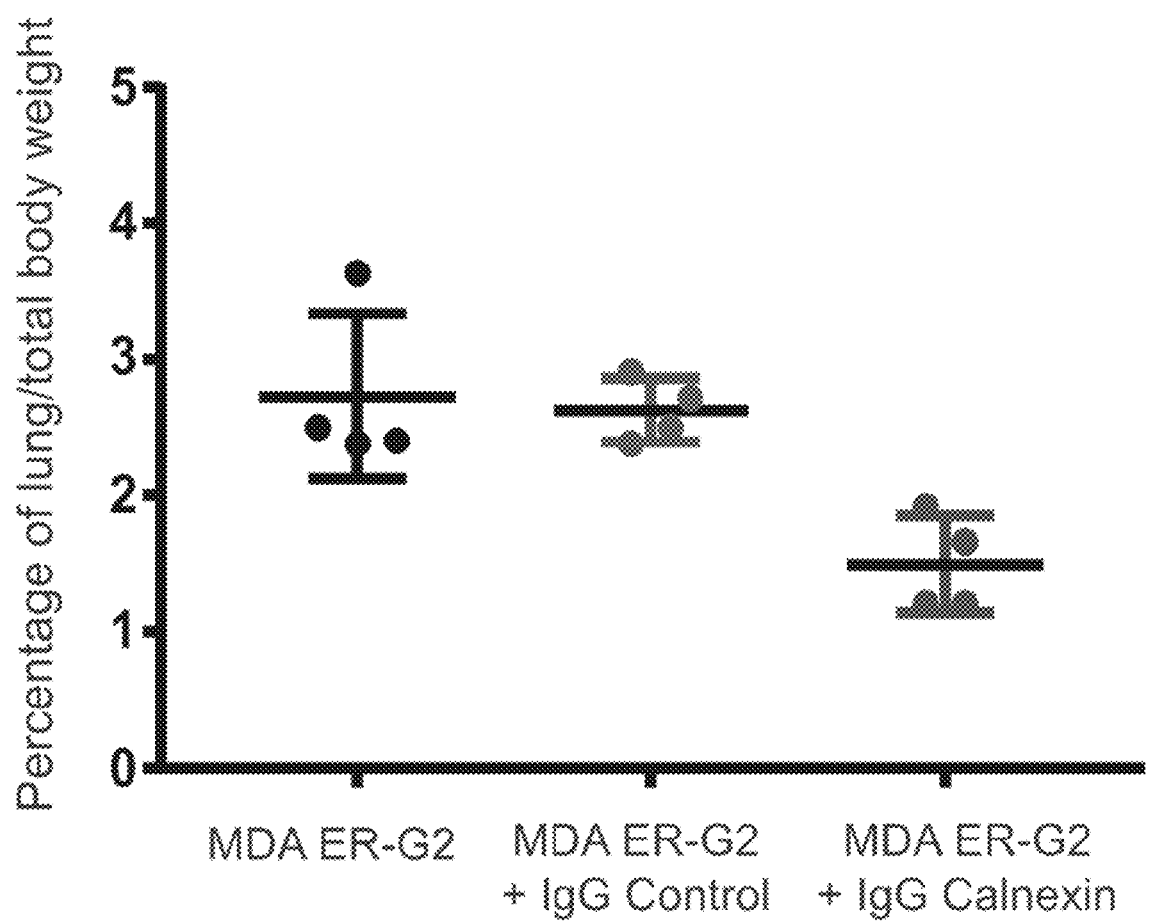
Figure 5E:
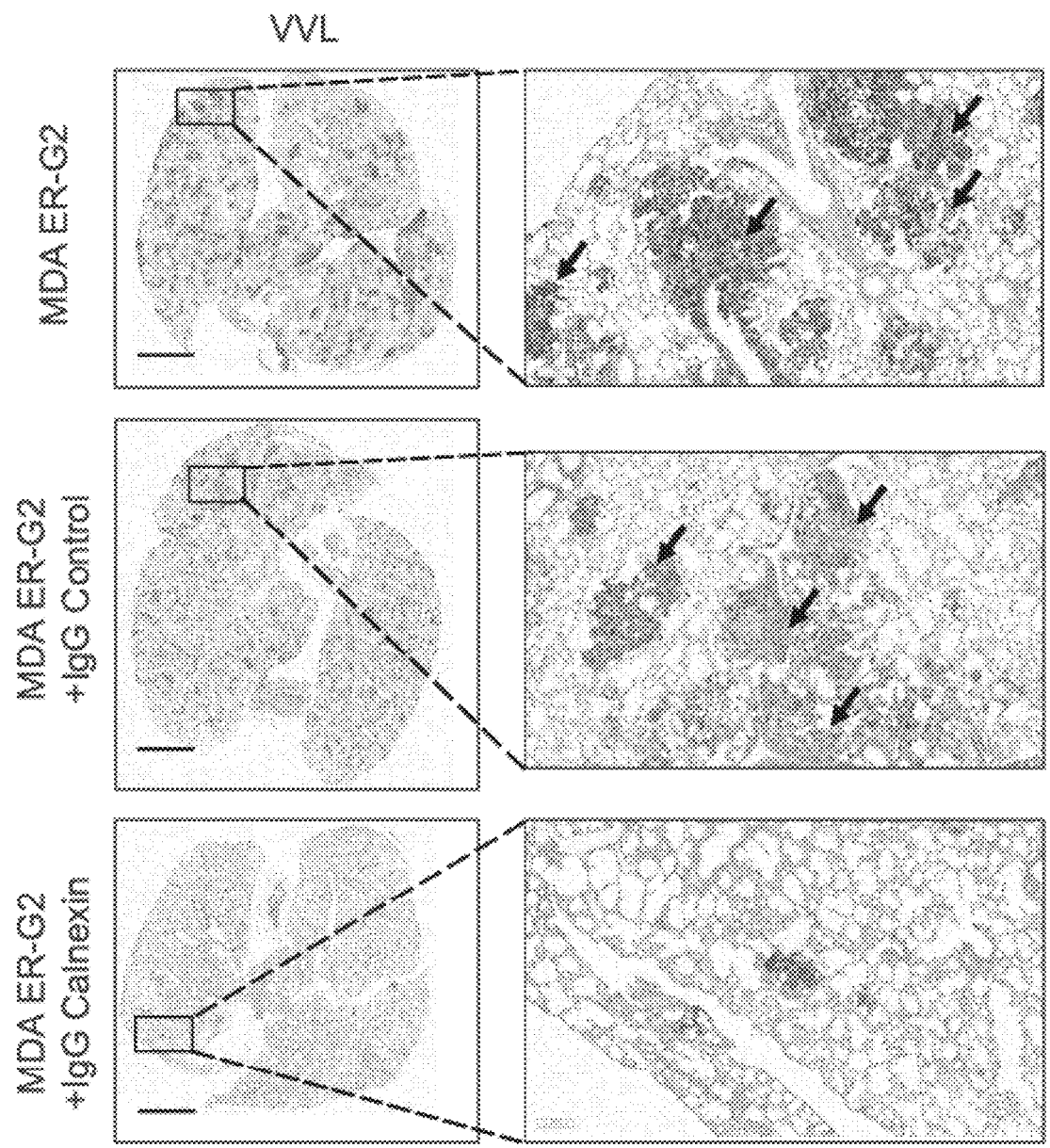
Figure 10A:
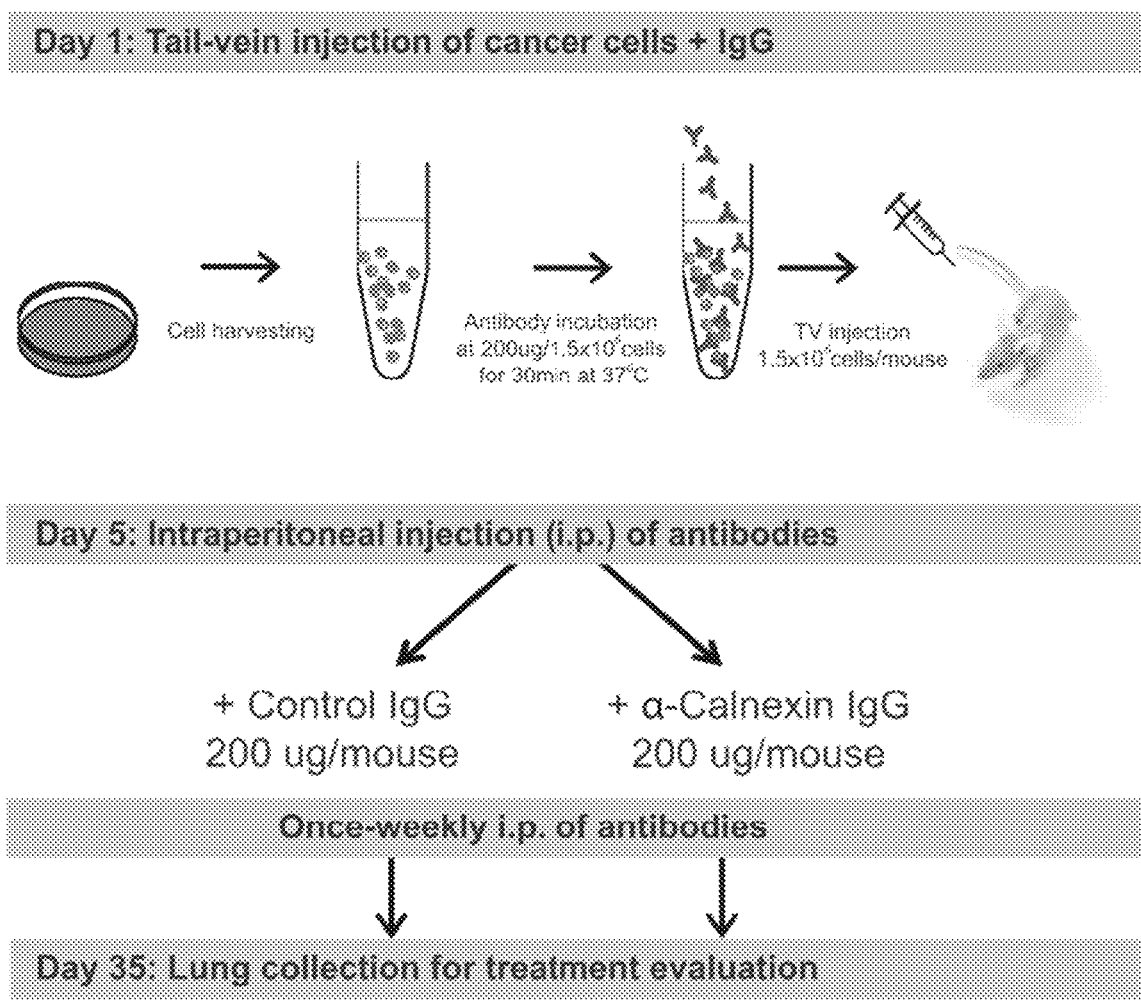
FIG. 10A is a drawing showing a schematic diagram of experiments using a mouse model of breast cancer metastasis to the lung to test anti-calnexin antibody.

Since ECM degradation is important for cancer cell invasion, we next sought to test whether GALA and Cnx was important for metastasis. MDA-MB-231 cell line is an established model for metastasis studies: after tail vein injection in 6-week-old nude BALB/c mice, they form nodules in the lungs. Using VVL staining on histological slices to reveal tumoral cells, we counted nodules bigger than 0.2 mm after 6 weeks (FIG. 5A). We observed that activation of GALA in MDA ER-G2 was able to promote their metastatic ability by at least one order of magnitude (FIG. 5A, FIG. 5B). Next, we incubated MDA ER-G2 with an anti-Cnx antibody before injecting the cells (FIG. 10A). Five days later and once weekly for 30 days, the nude mice were injected intraperitoneally with the antibodies. This treatment resulted in a dramatic reduction of metastases, which were barely detectable in the treated mice (FIG. 5C, FIG. 5D, FIG. 5E). The reduction in tumor load was important and the lungs weight of treated animals was comparable to control mice. It was markedly affected in MDA ER-G2 injected mice (FIG. 5D).

Figure 5F:
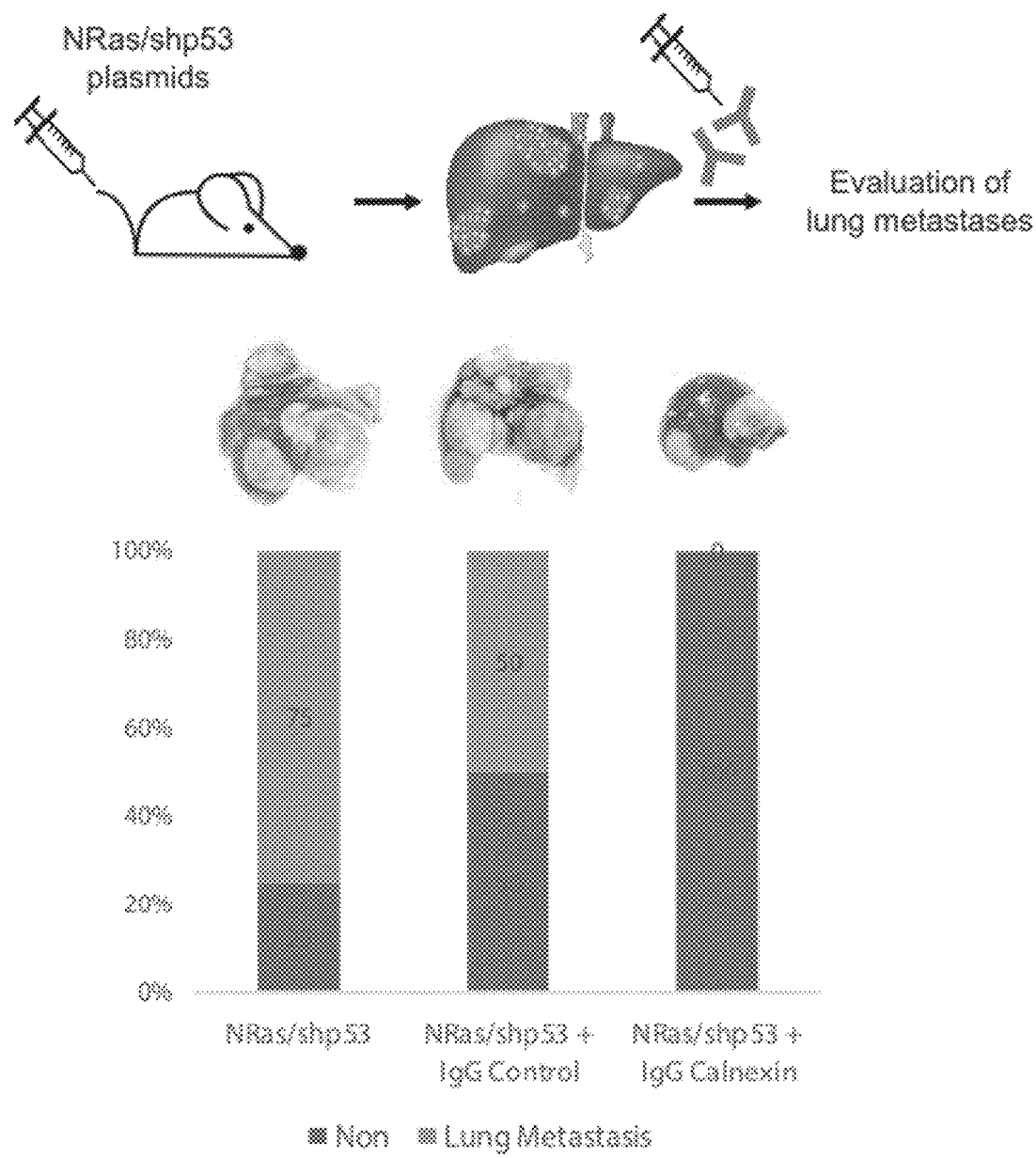
Figure 5G:
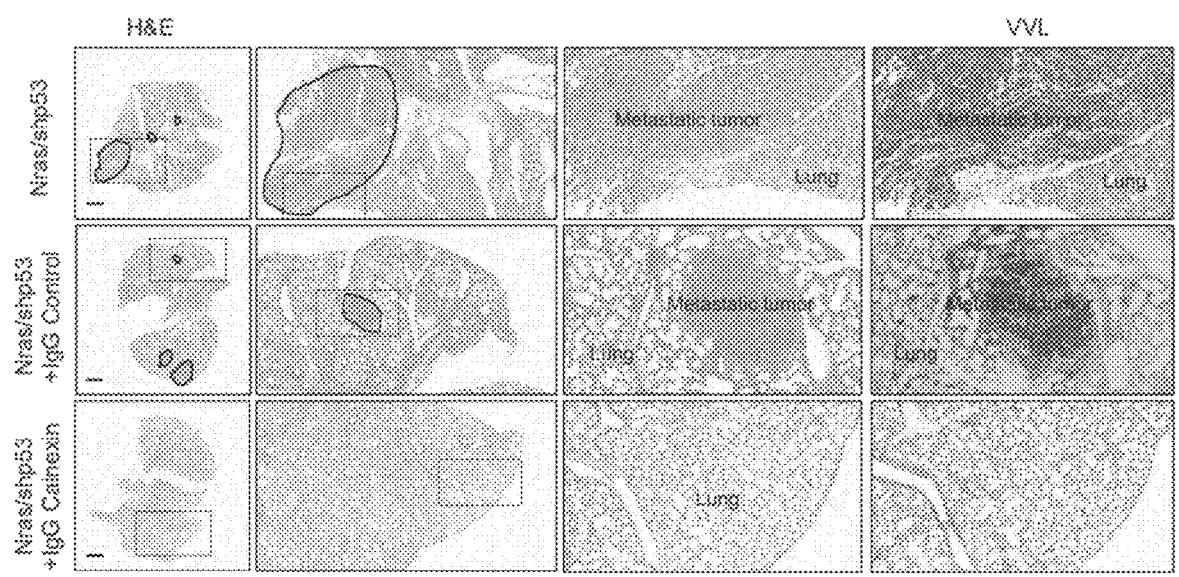
Figure 10B:
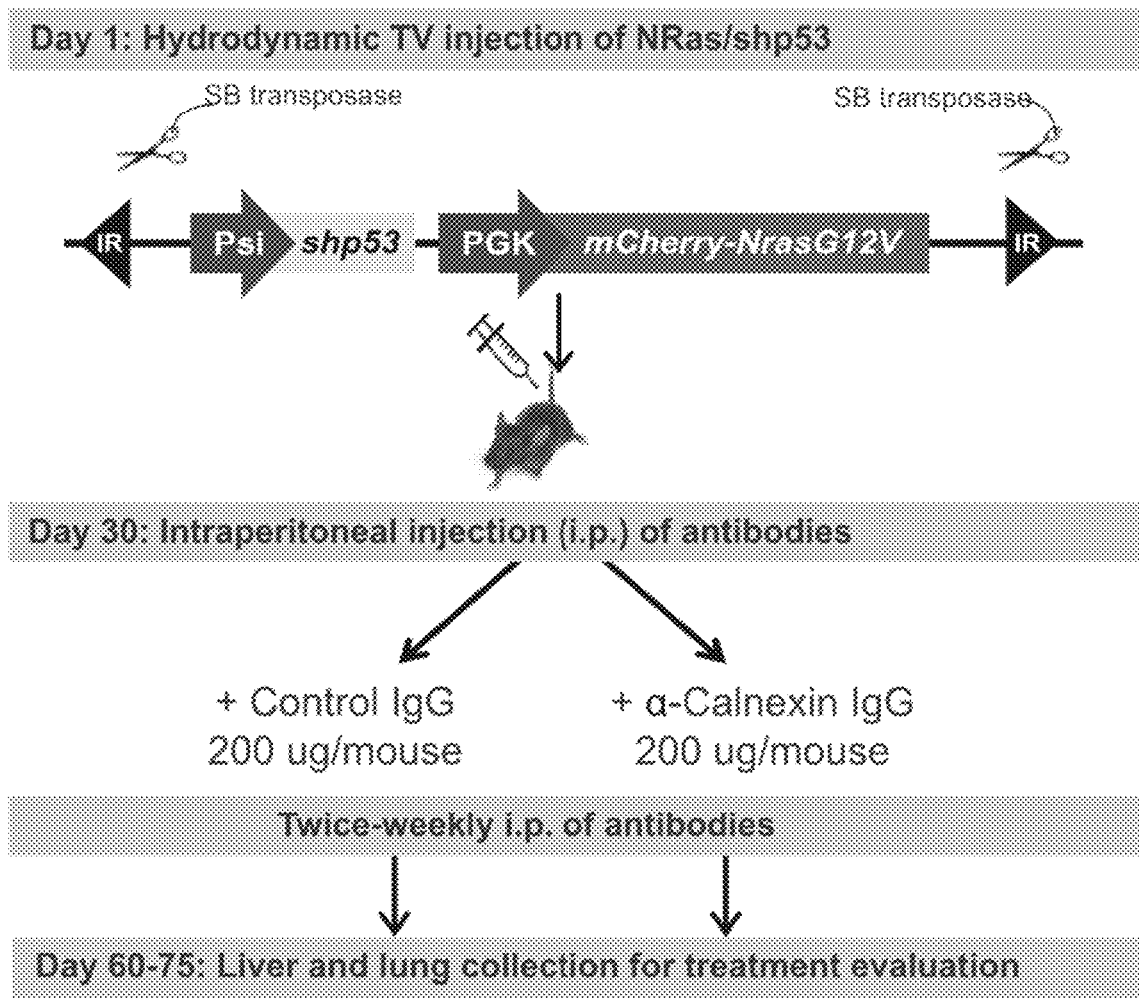
FIG. 10B is a drawing showing a schematic diagram of the workflow of the calnexin antibody treatment in a mouse model for liver cancer and its lung metastasis.

We next wanted to test whether the anti-Cnx antibody could also prevent lung metastasis from endogenous, N-RasV12 and anti-p53 shRNA-induced liver tumors. Lung metastasis in this model start to develop ~4 weeks after hydrodynamic injection. The tumors were allowed to develop for 30 days before antibodies injection. The mice were then treated twice weekly with antibody injection for an additional 45 days or until the animal required euthanasia (FIG. 5F, FIG. 10B). In this experiment, animals developed large liver tumor; however treatment with anti-Cnx antibody displayed smaller tumors, suggesting inhibition of tumor growth (FIG. 5F, FIG. 5G). Remarkably, despite the presence of tumors, animals treated with the anti-Cnx antibody did not present any lung metastases (FIG. 5F, FIG. 5G).

Example 8. Results: Anti-Cnx Antibody Prevents Tumor Growth In Vivo

Figure 6A:
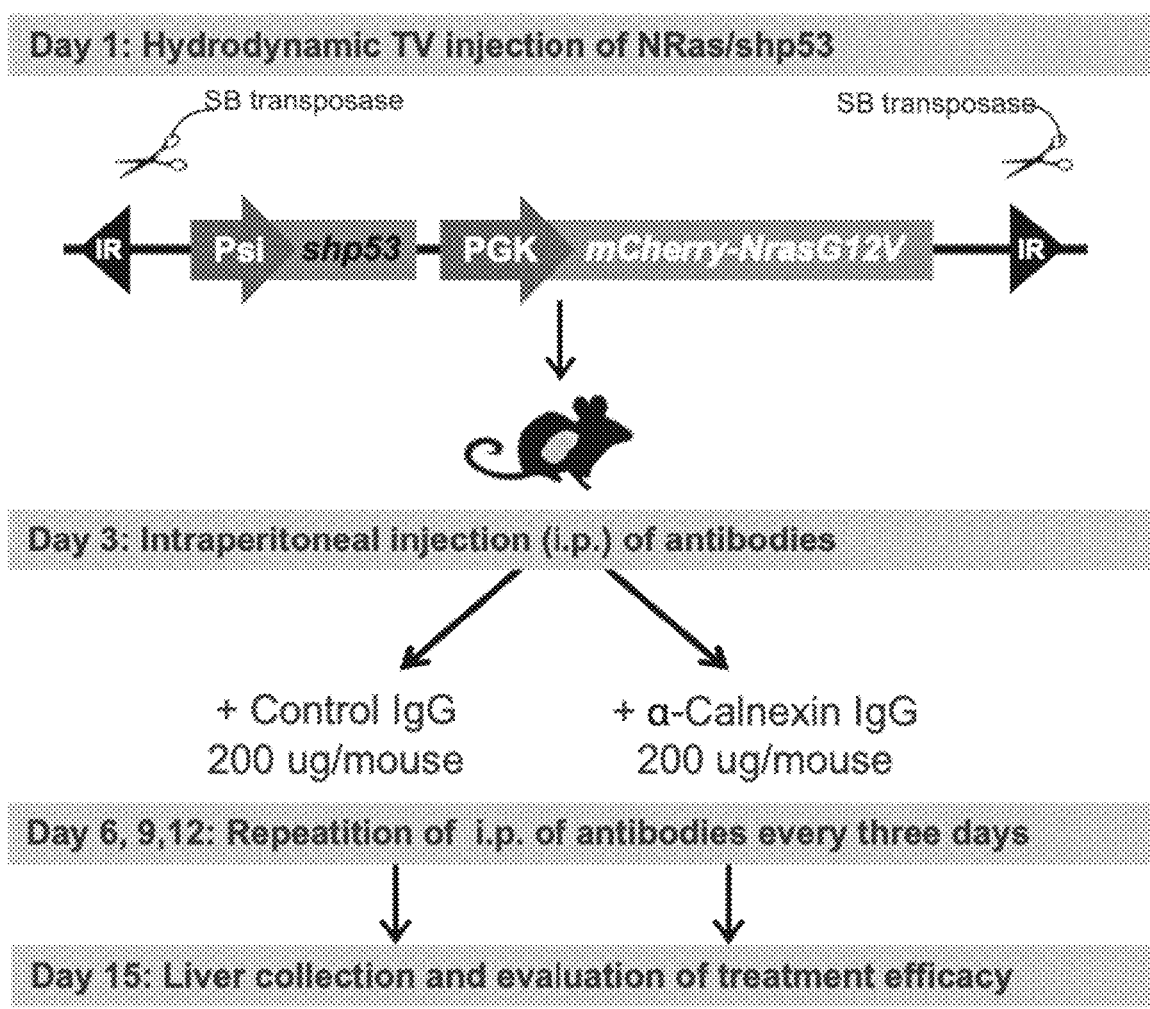
FIGS. 6A to 6D are drawings showing that antibody-mediated inhibition of Cnx reduces tumor growth
Figure 6B:
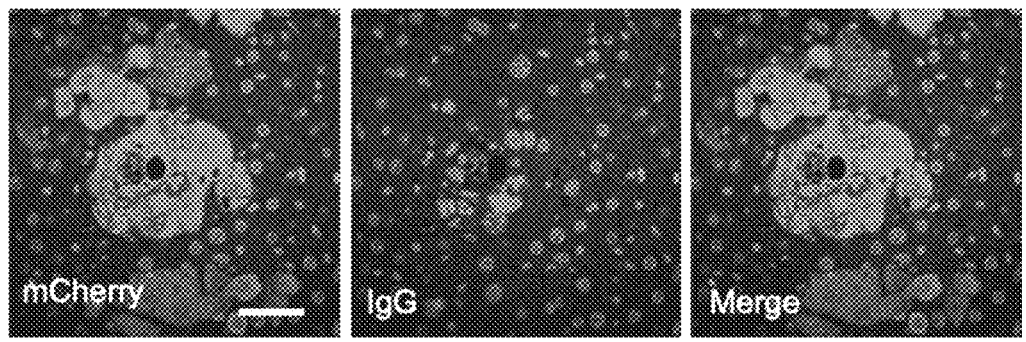
Figure 6B:
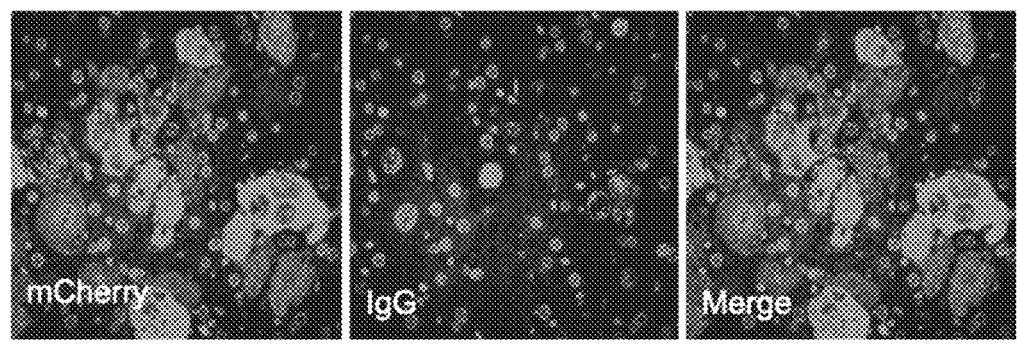
Figure 6B:
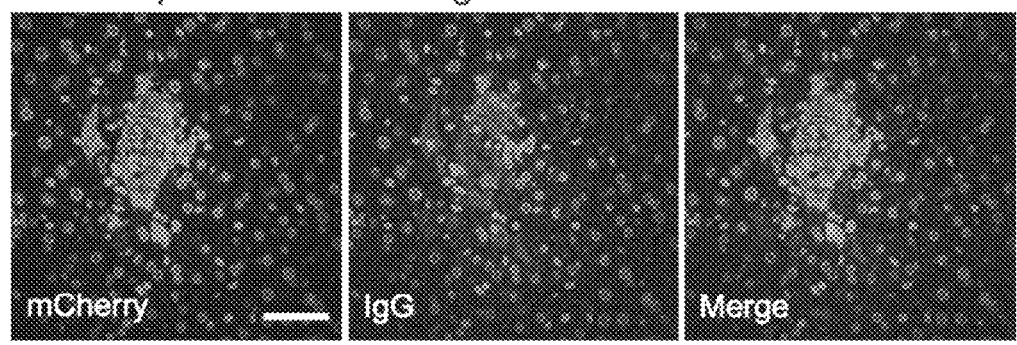
Figure 6B:
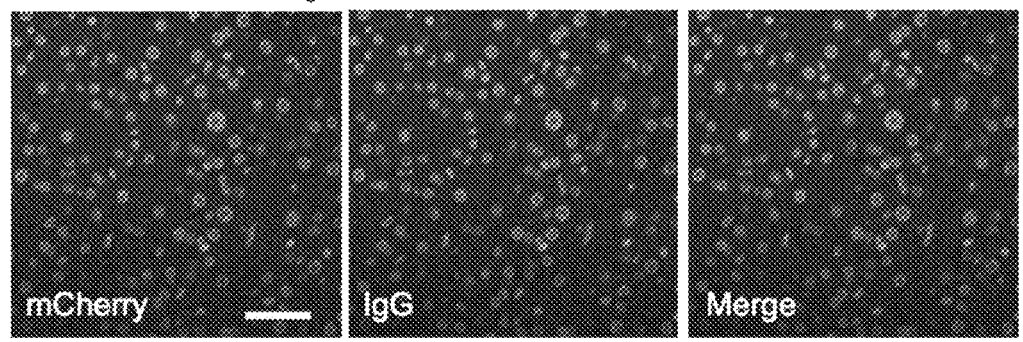

Results from the metastasis test suggested that cell surface Cnx is important during tumor growth. First, we sought to establish how early cell surface Cnx could be detected in vivo. HCC tumors were induced by hydrodynamic injection of plasmids encoding an oncogenic, mCherry tagged form of N-ras and an shRNA targeting p53, as previously described[3]. In this model system, tumors form abundant liver nodules as soon as two weeks post-injection. Mice were injected with 200 ug of rabbit anti-Cnx or control antibody three days post-injection and every three days until collection at day 15 (FIG. 6A). Liver tissues were processed and stained with an anti-rabbit IgG. Remarkably, tumor cells exposed to Cnx antibody revealed a clear intracellular signal, suggesting internalisation of the antibody, whereas the IgG injection control was completely negative and healthy hepatocytes did not uptake the Cnx antibody (FIG. 6B). These results indicate that liver tumor cells surface Cnx at early stages and had internalised the Cnx-antibody complex.

Figure 6C:
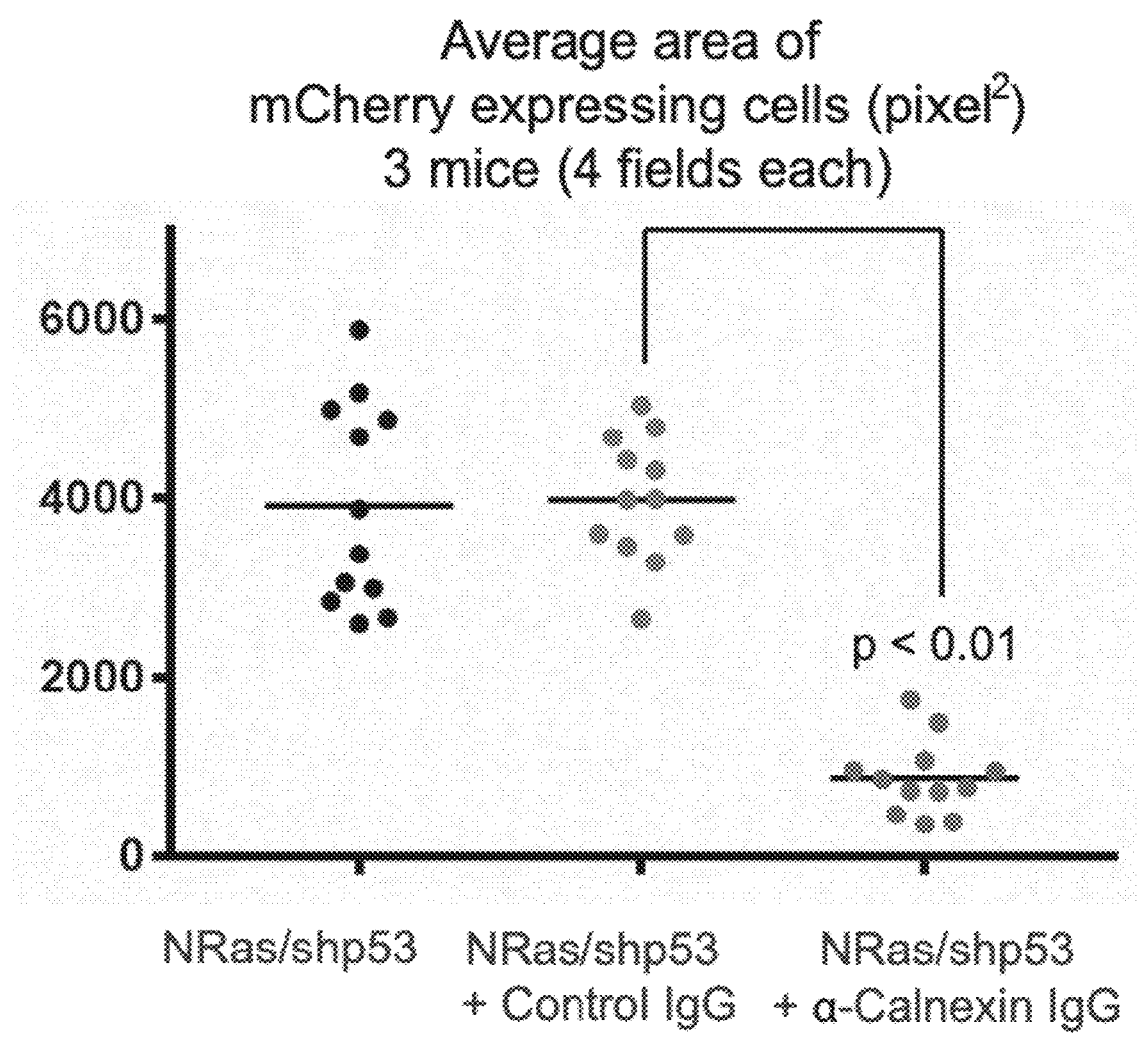
Figure 6D:
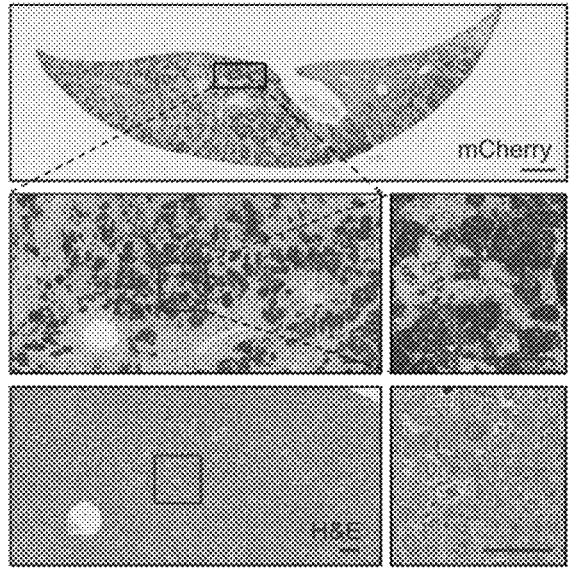
Figure 6D:
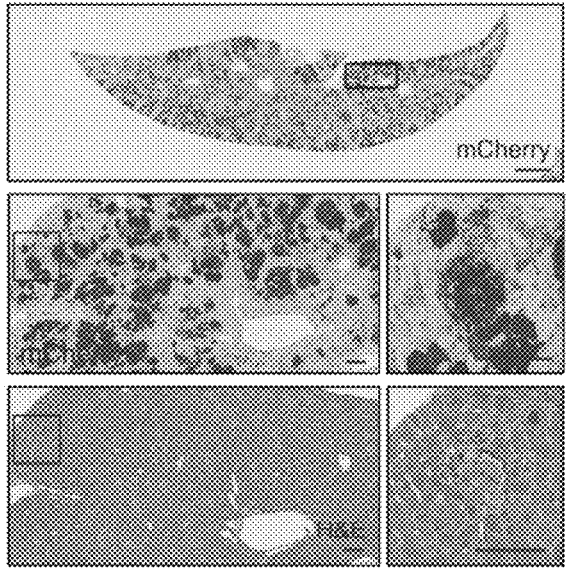
Figure 6D:
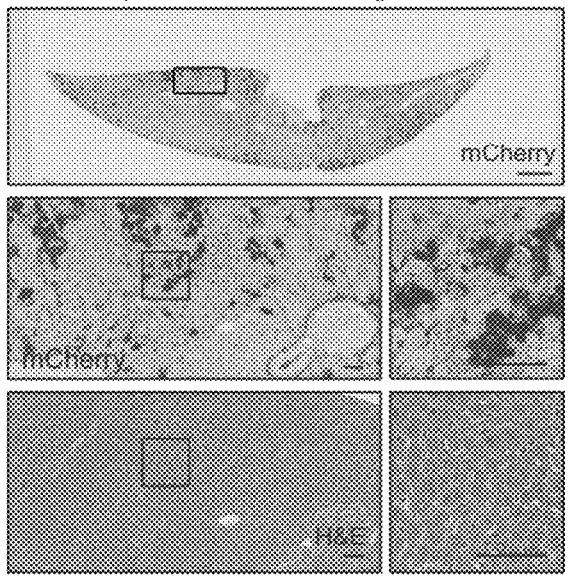

We noted again that nodules of tumors exposed to anti-Cnx antibody were fewer and contained significantly more dying tumor cells than in control conditions (FIG. 6B). Quantification of nodules area in histological slices using mCherry signal revealed a reduction of about 4 fold in anti-Cnx treated mice (FIG. 6C, FIG. 6D). Collectively these results demonstrate that Cnx is exposed at the surface of cancer cells at early tumor stages and establish this ER resident protein as a potentially specific surface cancer target.

Example 9. Discussion

ECM degradation is a fundamental requirement for solid cancers as growth within a tissue requires the destruction then remodelling of tissular structural elements. How this degradation is achieved by cells is therefore of fundamental importance. Our data indicate that, in addition to proteases, a disulfide bond reductase activity is required for efficient ECM degradation.

What are these disulfide bridges connecting? Multiple proteins of the ECM, including several collagens, fibronectin, and many others are known to contain intramolecular disulfide bonds that are essential for their function. The ECM is a complex meshwork of fibrillar molecules that interact and are cross-linked together. For instance, Lysyl oxidase (LOX)-initiated covalent intermolecular cross-linking stabilises collagen fibers[22]. While less is known about intermolecular disulfide bridges, the QSOX enzyme catalyses disulfide bridges that allow incorporation of laminin into the ECM secreted by fibroblasts[29].

Overall, our data using NEM and OX-133 antibody to reveal disulfide bridges indicate these bonds are abundant in all the ECM preparations that we tested. In liver ECM, OX-133 staining colocalizes with collagen type IV, but also collagen type III and fibronectin, all molecules known to contain disulfide bridges[26,42,43]. While collagen type I present in abundance in the mixture derived from rat tail does not contain disulfide bridges, this ECM preparation contains many other molecules, such as collagen XII and fibronectin as we have observed (data not shown). Interestingly, chemical reduction of disulfide bridges in the ECM preparations we used repeatedly resulted in changes in the morphology of fibers, with a looser appearance that suggests these disulfide bridges play essential structural roles; obviously, these bonds remain to be mapped and characterised more precisely.

The chemical reduction of these ECM disulfide bonds stimulated the destructive activity of cells. In addition, cells that degrade efficiently are endowed with an oxidoreductase complex concentrated in the subcellular structures involved in matrix degradation. This complex is composed of the transmembrane protein Cnx and its binding partner ERp57. Genetic depletion or antibody-mediated interference with one of these two proteins strongly impaired ECM degradation and this effect could be reversed by prior ECM reduction. Altogether, the evidence assembled here indicates that cleaving these cysteine bridges is essential for the ECM degradative ability of cells.

Cnx is an abundant transmembrane protein with multiple roles[44-46]. In the tumor cells we tested, a modest fraction of the ER pool of Cnx translocates to the cell surface, suggesting its ER functions may not be very impacted. In the ER, Cnx has been shown to interact with nascent polypeptides, promoting folding and preventing aggregation[44]. The Cnx-paralog calreticulin (Crt), in complex with ERp57, regulates collagen fibers assembly intracellularly, illustrating the ability of this complex to interact with collagen[47]. More recently, Cnx and ERp57 have been shown to target ER-located collagen aggregates to the endolysosomal system 48. In the ER, ERp57 functions primarily in complex with Cnx or Crt and acts in vitro as a thiol oxidase, reductase or isomerase[44]. For the substrate influenza hemagglutinin (HA), loss of Cnx induces disulfide-linked aggregates, further supporting Cnx/ERp57 complex as a reductase of disulfide bonds in vivo[49].

What is the source of electrons for the reduction of disulfide bonds in the ECM? GSH has been proposed to promote the reduction of key cysteines residues in ERp57[35, 50,51]. While GSH is formed intracellularly, the tripeptide is known to be present in the extracellular medium and transmembrane exporters have been identified[52]. Consistent with its role in catalytically mediated ECM reduction, GSH supplemented extracellularly stimulated ECM degradation, while the addition of an enzyme oxidizing GSH reduced ECM degradation. If this interpretation is correct, it will be interesting to explore how cells regulate the secretion of GSH and coordinate it with the cell surface exposure of the Cnx-ERp57 complex.

The export of the complex appears to be driven by the O-glycosylation of Cnx. We found that this glycosylation occurs in cells where GALA, or ER O-glycosylation, is activated. As demonstrated by the MDA-MD231 derived cell lines, the ER-localised enzyme GALNT2 is sufficient to glycosylate Cnx and induce its cell surface export. GALNT2 is a ubiquitously expressed enzyme, so on first approximation, any tumor cells with elevated levels of GALA are likely to glycosylate Cnx and activate export. The mechanism controlling this export remains unknown but are likely to interrupt ER retention mechanisms. Cnx ER retention is mediated by its cytosolic domain, with an important pair of arginines, and is dependent on the adaptor protein PACS2[53,54]. Exposure of Cnx at the cell surface has been reported before and it was proposed to depend on its glycoprotein binding domain[55]. Interestingly, the glycosylated residues are localised on this domain and close to the membrane. Similarly, the cell surface exposure of ERp57 has been reported previously; interestingly in conditions associated with ECM remodelling, such as in activated platelets, in fibrotic conditions and in cancer cells[56-58]. So, the surfacing of this ER resident complex appears to be a relatively frequent phenomenon; in fact, given the high prevalence of GALA in malignant tumors, this induction of a high cell surface reductive activity could be as common as high metalloprotease activity[59].

Interestingly, targeting tumors in vivo using antibody injections resulted in tumor growth prevention and metastasis blockade. While some anti-tumoral effects of the antibody may be due to antibody dependent cellular toxicity, the marked reduction of metastases formation suggest that the antibody also prevents ECM degradation by the cancer cells. To degrade a highly cross-linked ECM, cells must activate several processes, including the formation of invadosomes, the expression and activation of MMPs, the targeting of MMP14 and Cnx/ERp57 to invadosomes and the secretion of GSH. Interestingly, both invadosomes formation and GALA are induced by the Src tyrosine kinase[60 12]. GALA in turn coordinates proteolysis and disulfide reduction through glycosylation of MMP14 and Cnx[3]. Thus ECM degradation by cells emerges as a highly coordinated process involving the hitherto underappreciated surfacing of ER-resident protein complexes.

REFERENCES

1. Hotary, K., Allen, E., Punturieri, A., Yana, I. & Weiss, S. J. Regulation of cell invasion and morphogenesis in a 1. three-dimensional type I collagen matrix by membrane-type matrix metalloproteinases 1, 2, and 3. *J. Cell Biol.* 149, 1309-1323 (2000).
2. Hotary, K. B. et al. Membrane type I matrix metalloproteinase usurps tumor growth control imposed by the three-dimensional extracellular matrix. *Cell* 114, 33-45 (2003).
3. Nguyen, A. T. et al. Organelle Specific O-Glycosylation Drives MMP14 Activation, Tumor Growth, and Metastasis. *Cancer Cell* 32, 639-653.e6 (2017).
4. Nissen, R., Cardinale, G. J. & Udenfriend, S. Increased turnover of arterial collagen in hypertensive rats. *Proc. Natl. Acad. Sci. U.S.A* 75, 451-453 (1978).
5. Jabłońska-Trypuć, A., Matejczyk, M. & Rosochacki, S. Matrix metalloproteinases (MMPs), the main extracellular matrix (ECM) enzymes in collagen degradation, as a target for anticancer drugs. *J. Enzyme Inhib. Med. Chem.* 31, 177-183 (2016).
6. Lu, P., Takai, K., Weaver, V. M. & Werb, Z. Extracellular matrix degradation and remodeling in development and disease. *Cold Spring Harb. Perspect. Biol.* 3, (2011).
7. Bonnans, C., Chou, J. & Werb, Z. Remodelling the extracellular matrix in development and disease. *Nat. Rev. Mol. Cell Biol.* 15, 786-801 (2014).
8. Poincloux, R., Lizárraga, F. & Chavrier, P. Matrix invasion by tumour cells: a focus on MT1-MMP trafficking to invadopodia. *J. Cell Sci.* 122, 3015-3024 (2009).
9. Linder, S., Wiesner, C. & Himmel, M. Degrading devices: invadosomes in proteolytic cell invasion. *Annu. Rev. Cell Dev. Biol.* 27, 185-211 (2011).
10. Paterson, E. K. & Courtneidge, S. A. Invadosomes are coming: new insights into function and disease relevance. *FEBS J.* 285, 8-27 (2018).
11. Murphy, D. A. & Courtneidge, S. A. The 'ins' and 'outs' of podosomes and invadopodia: characteristics, formation and function. *Nat. Rev. Mol. Cell Biol.* 12, 413-426 (2011).
12. Gill, D. J., Chia, J., Senewiratne, J. & Bard, F. Regulation of O-glycosylation through Golgi-to-ER relocation of initiation enzymes. *J. Cell Biol.* 189, 843-858 (2010).
13. Gill, D. J. et al. Initiation of GalNAc-type O-glycosylation in the endoplasmic reticulum promotes cancer cell invasiveness. *Proc. Natl. Acad. Sci. U.S.A* 110, E3152-61 (2013).
14. Bard, F. & Chia, J. Cracking the Glycome Encoder: Signaling, Trafficking, and Glycosylation. *Trends Cell Biol.* 26, 379-388 (2016).
15. Chia, J., Tay, F. & Bard, F. The GalNAc-T Activation (GALA) Pathway: Drivers and markers. *PLoS One* 14, e0214118 (2019).
16. Springer, G. F. T and Tn, general carcinoma autoantigens. *Science* 224, 1198-1206 (1984).
17. Ju, T., Otto, V. I. & Cummings, R. D. The Tn Antigen-Structural Simplicity and Biological Complexity. *Angewandte Chemie International Edition* vol. 50 1770-1791 (2011).
18. Ju, T. et al. Tn and sialyl-Tn antigens, aberrant 0-glycomics as human disease markers. *Proteomics Clin. Appl.* 7, 618-631 (2013).
19. Chia, J., Goh, G. & Bard, F. Short 0-GalNAc glycans: regulation and role in tumor development and clinical perspectives. *Biochim. Biophys. Acta* 1860, 1623-1639 (2016).
20. Chia, J., Tham, K. M., Gill, D. J., Bard-Chapeau, E. A. & Bard, F. A. ERK8 is a negative regulator of O-GalNAc glycosylation and cell migration. *Elife* 3, e01828 (2014).
21. Naba, A. et al. *The extracellular matrix: Tools and insights for the 'omics' era. Matrix Biol.* 49, 10-24 (2016).
22. Herchenhan, A. et al. Lysyl Oxidase Activity Is Required for Ordered Collagen Fibrillogenesis by Tendon Cells. *J. Biol. Chem.* 290, 16440-16450 (2015).
23. Weadock, K. S., Miller, E. J., Keuffel, E. L. & Dunn, M. G. Effect of physical crosslinking methods on collagen-fiber durability in proteolytic solutions. *J. Biomed. Mater. Res.* 32, 221-226 (1996).
24. Boudko, S. P. & Bachinger, H. P. The von Willebrand Factor A3 domain binding region of type III collagen stabilized by the cysteine knot. (2012) doi:10.2210/pdb4gyx/pdb.
25. Barth, D. et al. The role of cystine knots in collagen folding and stability, part I. Conformational properties of (Pro-Hyp-Gly)5 and (Pro-(4S)-FPro-Gly)5 model trimers with an artificial cystine knot. *Chemistry* 9, 3692-3702 (2003).
26. Khoshnoodi, J., Pedchenko, V. & Hudson, B. G. Mammalian collagen IV. *Microsc. Res. Tech.* 71, 357-370 (2008).
27. Engel, J. et al. Structure and macromolecular organization of type VI collagen. *Ann. N. E Acad. Sci.* 460, 25-37 (1985).
28. Birk, D. E. Type V collagen: heterotypic type I/V collagen interactions in the regulation of fibril assembly. *Micron* 32, 223-237 (2001).
29. Ilani, T. et al. A secreted disulfide catalyst controls extracellular matrix composition and function. *Science* 341, 74-76 (2013).
30. Feige, M. J. & Hendershot, L. M. Disulfide bonds in ER protein folding and homeostasis. *Curr. Opin. Cell Biol.* 23, 167-175 (2011).
31. Bulleid, N. J. Disulfide bond formation in the mammalian endoplasmic reticulum. *Cold Spring Harb. Perspect. Biol.* 4, (2012).
32. Oka, O. B. V. & Bulleid, N. J. Forming disulfides in the endoplasmic reticulum. *Biochim. Biophys. Acta* 1833, 2425-2429 (2013).
33. Oliver, J. D., Roderick, H. L., Llewellyn, D. H. & High, S. ERp57 functions as a subunit of specific complexes formed with the ER lectins calreticulin and calnexin. *Mol. Biol. Cell* 10, 2573-2582 (1999).
34. Frickel, E.-M. et al. ERp57 is a multifunctional thiol-disulfide oxidoreductase. *J. Biol. Chem.* 279, 18277-18287 (2004).
35. Jessop, C. E. & Bulleid, N. J. Glutathione directly reduces oxidoreductases in the endoplasmic reticulum of mammalian cells. *J. Biol. Chem.* (2004).
36. Sefried, S., Häring, H.-U., Weigert, C. & Eckstein, S. S. Suitability of hepatocyte cell lines HepG2, AML12 and THLE-2 for investigation of insulin signalling and hepatokine gene expression. *Open Biol.* 8, (2018).
37. Nakabayashi, H., Taketa, K., Miyano, K., Yamane, T. & Sato, J. Growth of human hepatoma cells lines with differentiated functions in chemically defined medium. *Cancer Res.* 42, 3858-3863 (1982).
38. Juin, A. et al. Discoidin domain receptor 1 controls linear invadosome formation via a Cdc42-Tuba pathway. *J. Cell Biol.* 207, 517-533 (2014).
39. Steentoft, C. et al. Precision mapping of the human 0-GalNAc glycoproteome through SimpleCell technology. *EMBO J.* 32, 1478-1488 (2013).
40. Jessop, C. E. et al. ERp57 is essential for efficient folding of glycoproteins sharing common structural domains. *EMBO J.* 26, 28-40 (2007).

41. Holbrook, L.-M. et al. OX133, a monoclonal antibody recognizing protein-bound N-ethylmaleimide for the identification of reduced disulfide bonds in proteins. *MAbs* 8, 672-677 (2016).
42. Barth, D., Kyrieleis, O., Frank, S., Renner, C. & Moroder, L. The role of cystine knots in collagen folding and stability, part II. Conformational properties of (Pro-Hyp-Gly)n model trimers with N- and C-terminal collagen type III cystine knots. *Chemistry* 9, 3703-3714 (2003).
43. Pankov, R. & Yamada, K. M. Fibronectin at a glance. *J. Cell Sci.* 115, 3861-3863 (2002).
44. Williams, D. B. Beyond lectins: the calnexin/calreticulin chaperone system of the endoplasmic reticulum. *J. Cell Sci.* 119, 615-623 (2006).
45. Fregno, I. & Molinari, M. Proteasomal and lysosomal clearance of faulty secretory proteins: ER-associated degradation (ERAD) and ER-to-lysosome-associated degradation (ERLAD) pathways. *Crit. Rev. Biochem. Mol. Biol.* 1-11 (2019).
46. Lakkaraju, A. K. K. & van der Goot, F. G. Calnexin controls the STAT3-mediated transcriptional response to EGF. *Mol. Cell* 51, 386-396 (2013).
47. Van Duyn Graham, L., Sweetwyne, M. T., Pallero, M. A. & Murphy-Ullrich, J. E. Intracellular calreticulin regulates multiple steps in fibrillar collagen expression, trafficking, and processing into the extracellular matrix. *J. Biol. Chem.* 285, 7067-7078 (2010).
48. Fregno, I. et al. ER-to-lysosome-associated degradation of proteasome-resistant ATZ polymers occurs via receptor-mediated vesicular transport. *EMBO J.* 37, (2018).
49. Molinari, M. et al. Contrasting Functions of Calreticulin and Calnexin in Glycoprotein Folding and ER Quality Control. *Molecular Cell* vol. 13 125-135 (2004).
50. Chakravarthi, S., Jessop, C. E. & Bulleid, N. J. The role of glutathione in disulphide bond formation and endoplasmic-reticulum-generated oxidative stress. *EMBO Rep.* (2006).
51. Chakravarthi, S. & Bulleid, N. J. Glutathione is required to regulate the formation of native disulfide bonds within proteins entering the secretory pathway. *J. Biol. Chem.* 279, 39872-39879 (2004).
52. Franco, R., Schoneveld, O. J., Pappa, A. & Panayiotidis, M. I. The central role of glutathione in the pathophysiology of human diseases. *Arch. Physiol. Biochem.* 113, 234-258 (2007).
53. Rajagopalan, S., Xu, Y. & Brenner, M. B. Retention of unassembled components of integral membrane proteins by calnexin. *Science* 263, 387-390 (1994).
54. Myhill, N. et al. The subcellular distribution of calnexin is mediated by PACS-2. *Mol. Biol. Cell* 19, 2777-2788 (2008).
55. Okazaki, Y., Ohno, H., Takase, K., Ochiai, T. & Saito, T. Cell surface expression of calnexin, a molecular chaperone in the endoplasmic reticulum. *J. Biol. Chem.* 275, 35751-35758 (2000).
56. Holbrook, L.-M. et al. The platelet-surface thiol isomerase enzyme ERp57 modulates platelet function. *J. Thromb. Haemost.* 10, 278-288 (2012).
57. Obeid, M. ERP57 membrane translocation dictates the immunogenicity of tumor cell death by controlling the membrane translocation of calreticulin. *J. Immunol.* 181, 2533-2543 (2008).
58. Dihazi, H. et al. Secretion of ERP57 is important for extracellular matrix accumulation and progression of renal fibrosis, and is an early sign of disease onset. *J. Cell Sci.* 126, 3649-3663 (2013).
59. Kessenbrock, K., Plaks, V. & Werb, Z. Matrix metalloproteinases: regulators of the tumor microenvironment. *Cell* 141, 52-67 (2010).
60. Courtneidge, S. A., Azucena, E. F., Pass, I., Seals, D. F. & Tesfay, L. The Src Substrate Tks5, Podosomes (Invadopodia), and Cancer Cell Invasion. *Cold Spring Harbor Symposia on Quantitative Biology* vol. 70 167-171 (2005).

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

Each of the applications and patents mentioned in this document, and each document cited or referenced in each of the above applications and patents, including during the prosecution of each of the applications and patents ("application cited documents") and any manufacturer's instructions or catalogues for any products cited or mentioned in each of the applications and patents and in any of the application cited documents, are hereby incorporated herein by reference. Furthermore, all documents cited in this text, and all documents cited or referenced in documents cited in this text, and any manufacturer's instructions or catalogues for any products cited or mentioned in this text, are hereby incorporated herein by reference.

Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the claims.

The invention claimed is:

1. A method comprising administering an anti-calnexin (Cnx) antibody to a subject having cancer, wherein the cancer is characterized by a presence of a Cnx/ERp57 complex on the surface of a cancer cell, wherein the Cnx/Erp57 complex present on the surface of the cancer cell promotes extracellular matrix (ECM) degradation.

2. The method according to claim 1, wherein the Cnx/Erp57 complex promotes extracellular matrix (ECM) degradation by mediating a reduction of disulphide bonds in ECM fibers.

3. The method according to claim 1, wherein the cancer cell is further characterised by O-glycosylation of Cnx.

4. The method according to claim 1, wherein the cancer cell is further characterised by elevated levels of Cnx expression compared to a normal cell.

5. The method according to claim 1, wherein the cancer cell is an invasive or metastatic cancer cell.

6. The method according to claim 1, wherein the cancer cell is selected from the group consisting of: liver, breast, sarcoma, lung, prostate, bladder, kidney, melanoma, pancreatic, endometrial, colorectal and thyroid cancer cell.

7. The method according to claim 1, wherein the antibody is monoclonal.

8. The method according to claim 1, wherein the antibody is humanised.

* * * * *